(12) United States Patent
Osaka et al.

(10) Patent No.: US 7,993,761 B2
(45) Date of Patent: Aug. 9, 2011

(54) QUINOXALINE DERIVATIVE, AND LIGHT-EMITTING ELEMENT, LIGHT-EMITTING DEVICE, AND ELECTRONIC DEVICE USING THE SAME

(75) Inventors: Harue Osaka, Kanagawa (JP);
Nobuharu Ohsawa, Kanagawa (JP);
Sachiko Kawakami, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 323 days.

(21) Appl. No.: 12/326,342

(22) Filed: Dec. 2, 2008

(65) Prior Publication Data
US 2009/0140644 A1 Jun. 4, 2009

(30) Foreign Application Priority Data
Dec. 3, 2007 (JP) .................. 2007-312190

(51) Int. Cl.
*H01L 51/54* (2006.01)
*H01J 1/62* (2006.01)
*C07D 241/36* (2006.01)

(52) U.S. Cl. ........ 428/690; 428/917; 313/504; 313/506; 544/353; 257/40

(58) Field of Classification Search .................. None
See application file for complete search history.

(56) References Cited

U.S. PATENT DOCUMENTS

| | | |
|---|---|---|
| 4,760,006 A | 7/1988 | Pawlowski |
| 5,366,811 A | 11/1994 | Higashi et al. |
| 5,466,392 A | 11/1995 | Hironaka et al. |
| 6,097,147 A | 8/2000 | Baldo et al. |
| 6,303,238 B1 | 10/2001 | Thompson et al. |
| 6,541,129 B1 | 4/2003 | Kawamura et al. |
| 6,830,828 B2 | 12/2004 | Thompson et al. |
| 6,902,830 B2 | 6/2005 | Thompson et al. |
| 7,001,536 B2 | 2/2006 | Thompson et al. |
| 7,034,026 B2 | 4/2006 | Barnett et al. |
| 7,074,534 B2 | 7/2006 | Herron et al. |
| 7,245,073 B2 | 7/2007 | Shitagaki et al. |
| 7,291,406 B2 | 11/2007 | Thompson et al. |
| 2003/0143430 A1 | 7/2003 | Kawamura et al. |

(Continued)

FOREIGN PATENT DOCUMENTS

EP 0 502 202 A1 9/1992

(Continued)

OTHER PUBLICATIONS

Delvigs, P., "Effects of Multifunctional Crosslinking Agents on the Thermomechanical Properties of Polyimide Films," Polymer Engineering and Science, vol. 16, No. 5, May 1976, pp. 323-326.

(Continued)

*Primary Examiner* — Dawn Garrett
(74) *Attorney, Agent, or Firm* — Husch Blackwell LLP

(57) ABSTRACT

The present invention provides a quinoxaline derivative represented by a general formula (G1). In the formula, $\alpha^1$ and $\alpha^2$ each independently represent an arylene group which has 13 or less carbon atoms forming a ring; Ar represents an aryl group which has 13 or less carbon atoms forming a ring; $R^1$ and $R^6$ each independently represent any of a hydrogen atom, an alkyl group having 1 to 6 carbon atoms, or an aryl group which has 13 or less carbon atoms forming a ring; and $R^2$ to $R^5$ and $R^7$ to $R^{10}$ each independently represent any of a hydrogen atom, an alkyl group having 1 to 6 carbon atoms, a substituted or unsubstituted phenyl group, or a substituted or unsubstituted biphenyl group.

23 Claims, 20 Drawing Sheets

U.S. PATENT DOCUMENTS

| | | |
|---|---|---|
| 2005/0186446 A1 | 8/2005 | Shitagaki et al. |
| 2005/0191527 A1 | 9/2005 | Fujii et al. |
| 2006/0082294 A1 | 4/2006 | Kawamura et al. |
| 2006/0263637 A1 | 11/2006 | Ohsawa et al. |
| 2007/0059553 A1 | 3/2007 | Egawa et al. |
| 2007/0222374 A1 | 9/2007 | Egawa et al. |
| 2007/0241667 A1 | 10/2007 | Ohsawa et al. |

FOREIGN PATENT DOCUMENTS

| | | |
|---|---|---|
| EP | 1 616 864 A1 | 1/2006 |
| JP | 64-57261 | 3/1989 |
| JP | 7-48385 | 2/1995 |
| JP | 7-53954 | 2/1995 |
| JP | 7-150137 | 6/1995 |
| JP | 8-73443 | 3/1996 |
| JP | 10-25473 | 1/1998 |
| JP | 2000-309566 | 11/2000 |
| JP | 2003-40873 | 2/2003 |
| JP | 2006-16384 | 1/2006 |
| WO | WO 92/05131 A1 | 4/1992 |
| WO | WO 01/41512 A1 | 6/2001 |
| WO | WO 2004/094389 A1 | 11/2004 |
| WO | WO 2005/115061 A1 | 12/2005 |
| WO | WO 2006/049334 A1 | 5/2006 |

OTHER PUBLICATIONS

Parker, S.P. et al, editors, *McGraw-Hill Dictionary of Chemical Terms*, 3$^{rd}$ edition, McGraw-Hill, publisher, 1984, p. 200.

Tang, C.W. et al, "Organic Electroluminescent Diodes," Applied Physics Letters, vol. 51, No. 12, Sep. 21, 1987, pp. 913-915.

Adachi, C. et al, "Electroluminescence in Organic Films with Three-Layer Structure," Japanese Journal of Applied Physics, vol. 27, No. 2, Feb. 1988, pp. L-269-L-271.

Jakubke, H-D et al, editors, *Concise Encyclopedia Chemistry*, Walter de Gruyter, publisher, 1993, p. 490.

Lewis, R.J., Sr., editor, *Hawley's Condensed Chemical Dictionary*, 12$^{th}$ edition, Van Nostrand Reinhold, publisher, 1993, p. 594.

Brock, T. et al, "Synthesis and Characterisation of Porous Particulate Polyimides," J. Mater. Chem., vol. 4, No. 2, 1994, pp. 229-236.

Thomas, K.R.J. et al, "Quinoxalines Incorporating Triarylamines: Potential Electroluminescent Materials with Tunable Emission Characteristics," Chem. Mater., vol. 14, No. 6, 2002, pp. 2796-2802.

Burrows, H.D. et al, "Fluorescence Study of Dehydroabietic Acid-Based Bipolar Arylamine-Quinoxalines," Journal of Fluorescence, vol. 16, No. 2, Mar. 2006, pp. 227-231.

Huang, T-H et al, "Quinoxalines Incorporating Triarylamines: Dipolar Electroluminescent Materials with Tunable Emission Characteristics," Journal of the Chinese Chemical Society, vol. 53, No. 1, 2006, pp. 233-242.

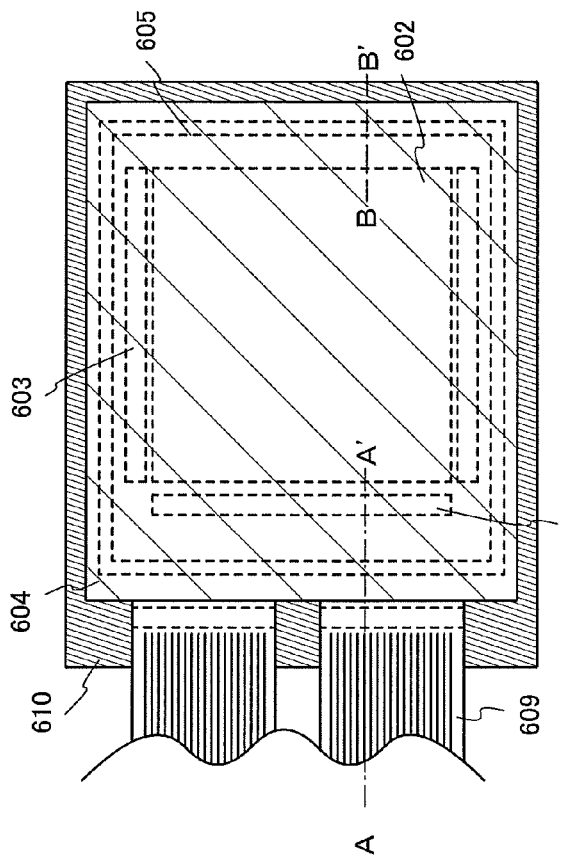
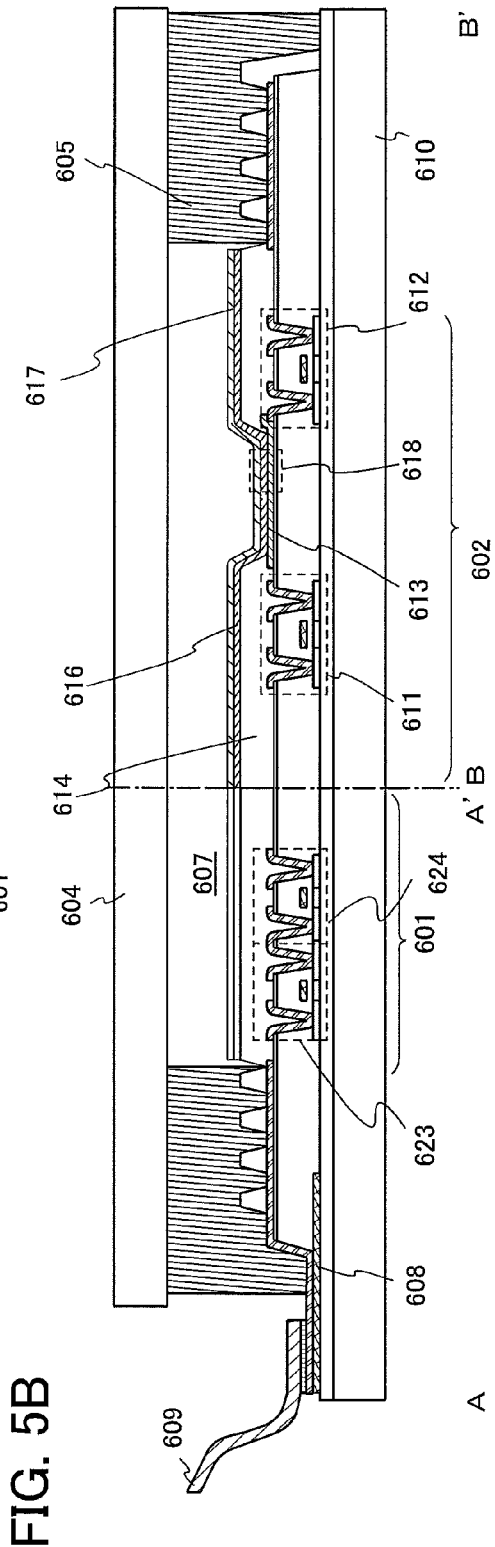
FIG. 5A
FIG. 5B

QUINOXALINE DERIVATIVE, AND LIGHT-EMITTING ELEMENT, LIGHT-EMITTING DEVICE, AND ELECTRONIC DEVICE USING THE SAME

BACKGROUND OF THE INVENTION

1. Field of the Invention

The present invention relates to a quinoxaline derivative, and a light-emitting element, a light-emitting device, and an electronic device each using the quinoxaline derivative.

2. Description of the Related Art

By using organic compounds, compared with inorganic compounds, a wider variety of structures can be taken and materials having a variety of functions depending on the molecular design can be synthesized. Because of these advantages, photo electronics and electronics each using functional organic materials have been attracting attention in recent years.

As examples of electronic devices using organic compounds as functional organic materials, there are solar cells, light-emitting elements, organic transistors, and the like. These examples are devices using electric properties and optical properties of such organic compounds. In particular, light-emitting elements have been developing remarkably.

A light emission mechanism is said to be as follows: by applying a voltage to a pair of electrodes with a light-emitting layer interposed therebetween, an electron injected from a cathode and a hole injected from an anode recombine with each other in an emission center of the light-emitting layer to form a molecular exciton, and the molecular exciton releases energy in returning to a ground state; accordingly, light is emitted. As excited states, a singlet excited state and a triplet excited state are known. It is thought that light emission can be obtained through either a singlet excited state or a triplet excited state.

Such light-emitting elements have a lot of material-dependant problems for improvement of element characteristics. In order to solve the problems, improvement of element structures, development of materials, and the like have been carried out.

As the most basic structure of a light-emitting element, the following structure is known: a hole-transporting layer made of an organic compound having a hole-transporting property and an electron-transporting light-emitting layer made of an organic compound having an electron-transporting property are stacked to form a thin film of approximately 100 nm thickness in total, and this thin film is interposed between electrodes (see Non-Patent Document 1: C. W. Tang et al., Applied Physics Letters, vol. 51, No. 12, pp. 913-915 (1987)).

By applying a voltage to the light-emitting element described in Non-Patent Document 1, light emission can be obtained from the organic compound having a light-emitting property and an electron-transporting property.

Further, in the light-emitting element described in Non-Patent Document 1, functions are separated so that the hole-transporting layer transports holes whereas the electron-transporting layer transports electrons and emits light. However, a variety of interactions (e.g., exciplex formation) frequently occur at an interface of stacked layers. As a result, a change in emission spectrum or a decrease in emission efficiency may occur.

In order to suppress a change in emission spectrum or a decrease in emission efficiency due to interactions at an interface, a light-emitting element having further functional separation has been developed. For example, a light-emitting element in which a light-emitting layer is interposed between a hole-transporting layer and an electron-transporting layer has been proposed (Non-Patent Document 2: Chihaya Adachi et al., Japanese Journal of Applied Physics, vol. 27, No. 2, L269-L271 (1988)).

For a light-emitting element as described in Non-Patent Document 2, in order to more effectively suppress interactions occurring at an interface, a light-emitting layer is preferably made of a bipolar organic compound having both an electron-transporting property and a hole-transporting property.

However, most organic compounds are monopolar materials having either a hole-transporting property or an electron-transporting property.

Therefore, development of bipolar organic compounds having both an electron-transporting property and a hole-transporting property has been required.

In Patent Document 1 (PCT International Publication No. 2004/094389), a bipolar quinoxaline derivative is disclosed. However, its characteristics are not yet satisfactory, and development of a wider variety of bipolar organic compounds has been required.

SUMMARY OF THE INVENTION

In view of the aforementioned problems, the present invention provides a new bipolar organic compound.

Further, by using the bipolar organic compound of the present invention, the present invention provides a light-emitting element having excellent carrier balance. Furthermore, by using the bipolar organic compound of the present invention, the present invention provides a light-emitting element which emits light having high color purity. Moreover, by using the bipolar organic compound of the present invention, the present invention provides a light-emitting element and a light-emitting device having low driving voltage and low power consumption.

Further, by using the bipolar organic comound of the present invention, the present invention provides an electronic device having low power consumption. Furthermore, by using the bipolar organic comound of the present invention, the present invention provides an electronic device having high display quality.

As a result of intense study, the present inventors have succeeded in synthesizing a quinoxaline derivative rerpesented by a general formula (G1) below as a bipolar organic comound having both an electron-transporting property and a hole-transporting property.

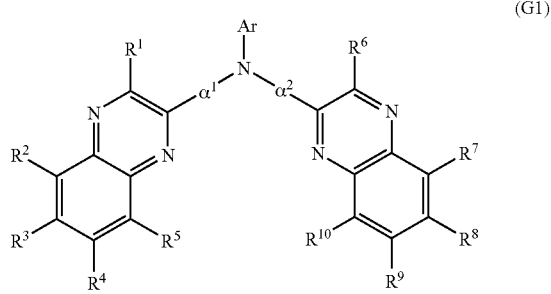

(G1)

In the formula, $\alpha^1$ and $\alpha^2$ each independently represent an arylene group which has 13 or less carbon atoms forming a ring; Ar represents an aryl group which has 13 or less carbon atoms forming a ring; $R^1$ and $R^6$ each independently represent any of a hydrogen atom, an alkyl group having 1 to 6 carbon atoms, or an aryl group which has 13 or less carbon atoms forming a ring; and $R$ to $R^5$ and $R^7$ to $R^{10}$ each independently represent any of a hydrogen atom, an alkyl group having 1 to 6 carbon atoms, a substituted or unsubstituted phenyl group, or a substituted or unsubstituted biphenyl group.

Further, the quinoxaline derivative of the present invention is a quinoxaline derivative in which $\alpha^1$ and $\alpha^2$ in the above general formula (G1) are each independently any of general formulae (2-1) to (2-7) below.

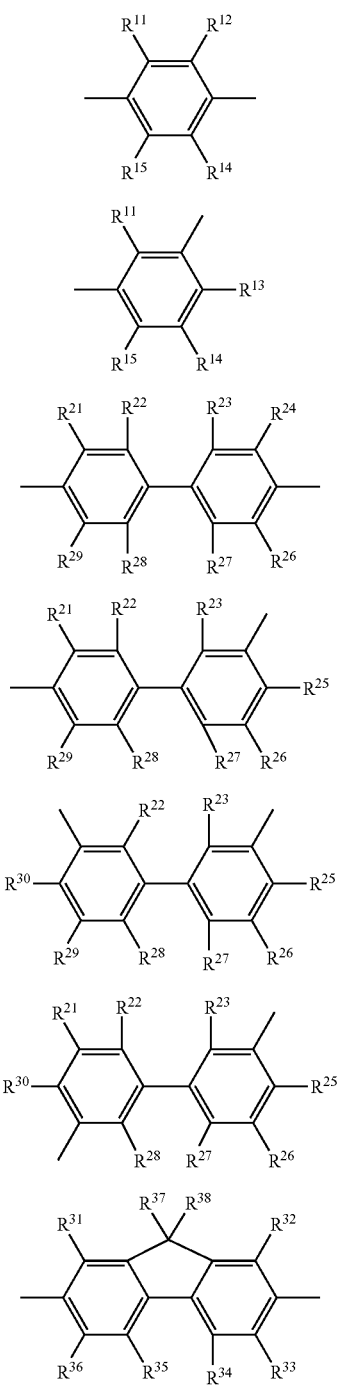

Further, the quinoxaline derivative of the present invention is a quinoxaline derivative in which Ar in the above general formula (G1) is any of general formulae (3-1) to (3-7) below.

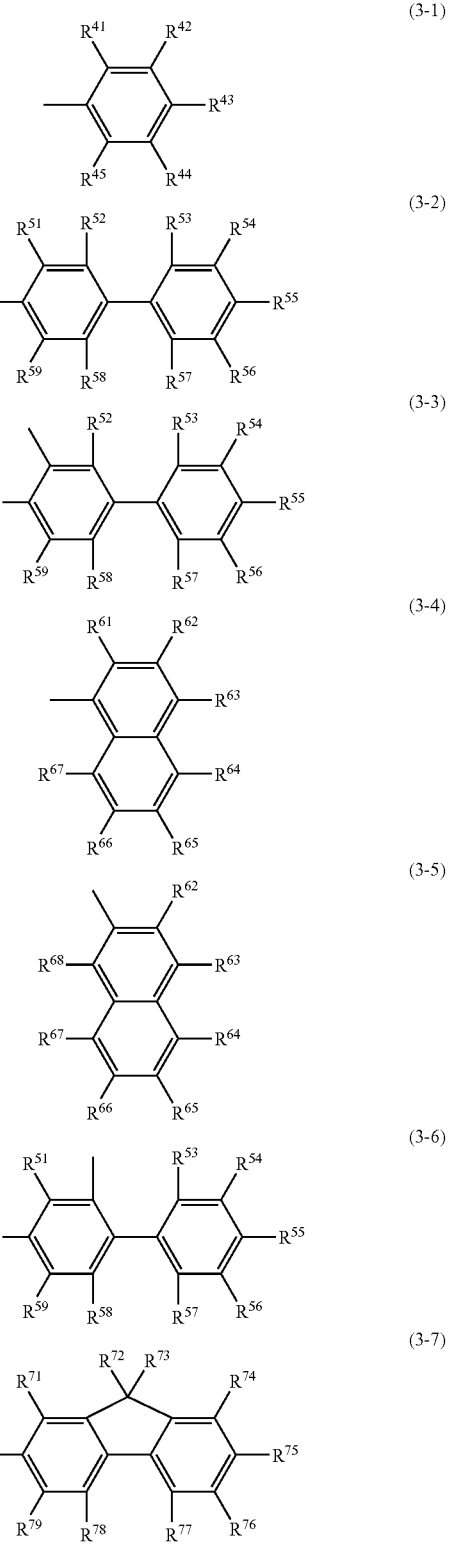

In the formula, $R^{11}$ to $R^{15}$ and $R^{21}$ to $R^{36}$ each independently represent any of a hydrogen atom, an alkyl group having 1 to 6 carbon atoms, or a phenyl group; and $R^{37}$ and $R^{38}$ each independently represent a hydrogen atom or an alkyl group having 1 to 6 carbon atoms.

In the formula, $R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group. Note that $R^{72}$ and $R^{73}$ may be bonded to each other to form a ring.

Further, the quinoxaline derivative of the present invention is a quinoxaline derivative in which $R^1$ and $R^6$ in the above general formula (G1) are each independently any of structural formulae (4-1) to (4-6) below or general formulae (4-7) to (4-12) below.

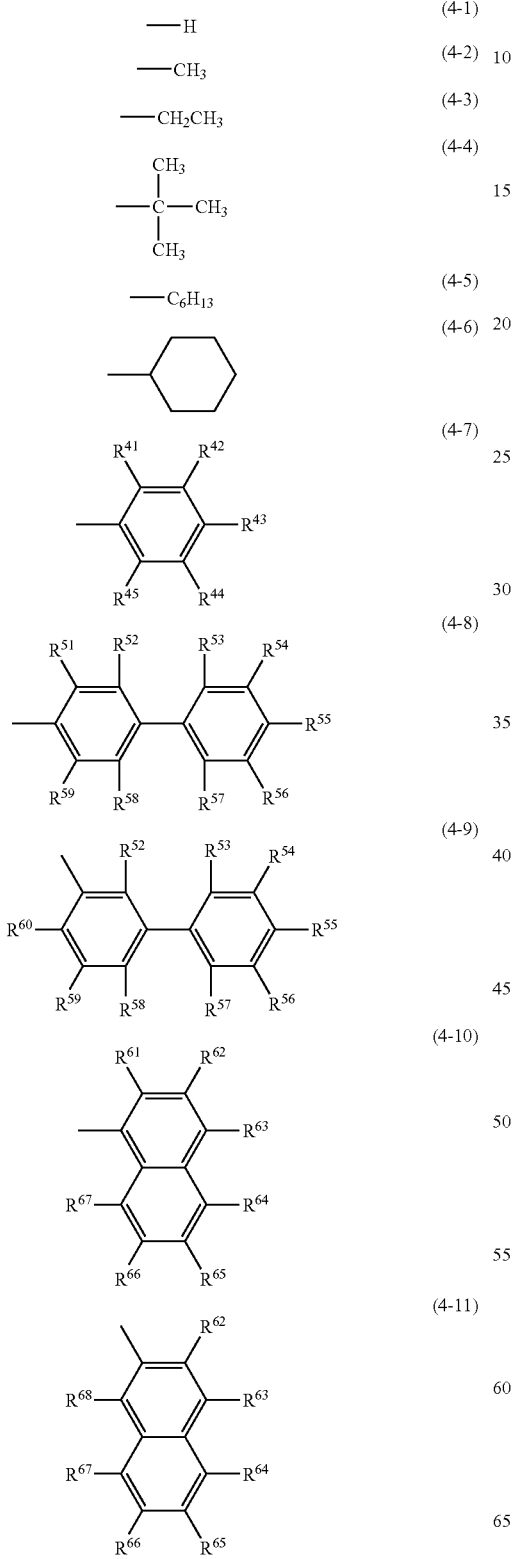

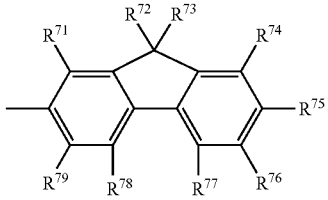

In the formula, $R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group. Note that $R^{72}$ and $R^{73}$ may be bonded to each other to form a ring.

Further, the quinoxaline derivative of the present invention is a quinoxaline derivative in which $R^2$ to R5 and $R^7$ to $R^{10}$ in the above general formula (G1) are each independently any of structural formulae (5-1) to (5-6) below or general formulae (5-7) to (5-10) below.

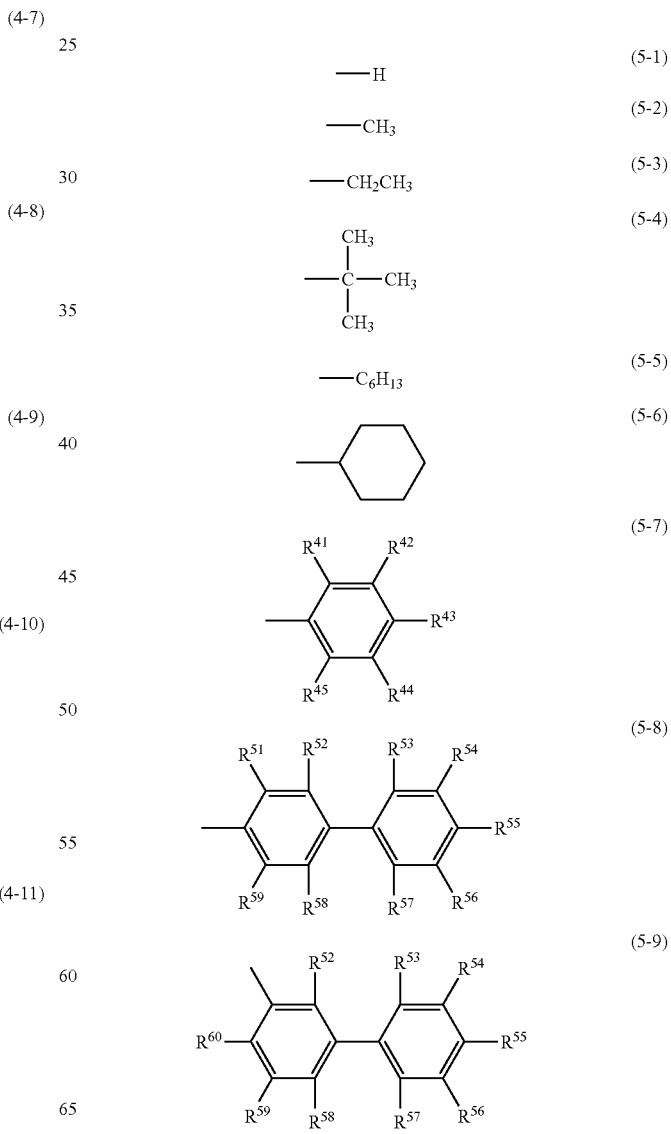

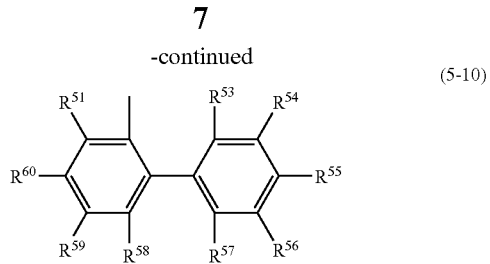

(5-10)

In the formula, $R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

Further, the quinoxaline derivative of the present invention is a quinoxaline derivative represented by a structural formula (1) below.

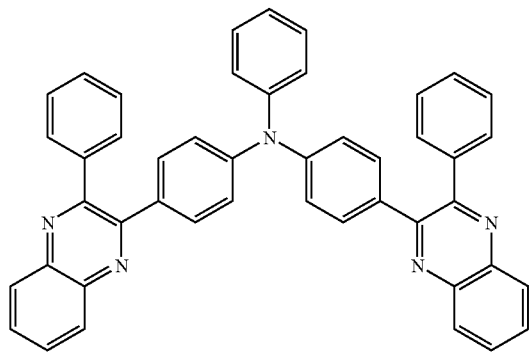

(1)

The quinoxaline derivative of the present invention having the above structure is a bipolar organic compound. Further, by applying this quinoxaline derivative to a light-emitting element, a light-emitting element with low driving voltage can be manufactured. Furthermore, a light-emitting element which emits light having high color purity can be obtained.

Further, an aspect of the present invention is a light-emitting element using the above quinoxaline derivative. Specifically, the light-emitting element includes the above quinoxaline derivative between a pair of electrodes.

Further, another aspect of the present invention is a light-emitting element having a light-emitting layer between a pair of electrodes, and the light-emitting layer includes the above quinoxaline derivative.

Further, another aspect of the present invention is a light-emitting element having a light-emitting layer between a pair of electrodes, and the light-emitting layer includes the above quinoxaline derivative and a fluorescent substance.

Further, another aspect of the present invention is a light-emitting element having a light-emitting layer between a pair of electrodes, and the light-emitting layer includes the above quinoxaline derivative and a phosphorescent substance.

A light-emitting element including the above quinoxaline derivative can be a light-emitting element with low driving voltage since this quinoxaline derivative is bipolar. Further, since this quinoxaline derivative is bipolar, a light-emitting element including this quinoxaline derivative in a light-emitting layer allows a light-emitting substance in the light-emitting layer to efficiently emit light. Further, in a light-emitting element including this quinoxaline derivative in a light-emitting layer, the carrier balance in the light-emitting layer is excellent and localization of a light-emitting region can be suppressed; thus, light emission from a layer other than the light-emitting layer can be suppressed. Accordingly, a light-emitting element which emits light having high color purity can be obtained.

The light-emitting device of the present invention has a light-emitting element which includes a layer containing a light-emitting substance between a pair of electrodes, and a control unit for controlling light emission from the light-emitting element, and the light-emitting element includes the above quinoxaline derivative. Note that the light-emitting device in this specification includes an image display device or a light-emitting device using a light-emitting element. Further, the category of the light-emitting device of the present invention includes a module including a substrate provided with a light-emitting element, to which a connector such as a tape automated bonding (TAB) tape such as an anisotropic conductive film or a tape carrier package (TCP) is attached; a module in which an end of a connector is provided with a printed wiring board; and a module in which an integrated circuit (IC) is directly mounted on a substrate provided with a light-emitting element by a chip on glass (COG) method. Furthermore, the category includes a light-emitting device used for a lightning apparatus and the like.

Further, the electronic device of the present invention has a display portion, and the display portion includes the above light-emitting element and a control unit for controlling light emission from the light-emitting element. The power consumption of such an electronic device can be reduced, and the display quality thereof can be improved.

The quinoxaline derivative of the present invention is bipolar and has both an excellent electron-transporting property and an excellent hole-transporting property. Further, the quinoxaline derivative of the present invention is stable with respect to reduction and oxidation by electrons.

A light-emitting element using the above quinoxaline derivative is a light-emitting element with low driving voltage and low power consumption since this quinoxaline derivative is bipolar. Further, the light-emitting element using the above quinoxaline derivative is a light-emitting element which emits light having high color purity.

Further, by using the quinoxaline derivative of the present invention, a display device and an electronic device with low power consumption can be obtained.

BRIEF DESCRIPTION OF THE DRAWINGS

FIGS. 5A and 5B illustrate a light-emitting device according to an aspect of the present invention.

DETAILED DESCRIPTION OF THE INVENTION

Figure 1A:
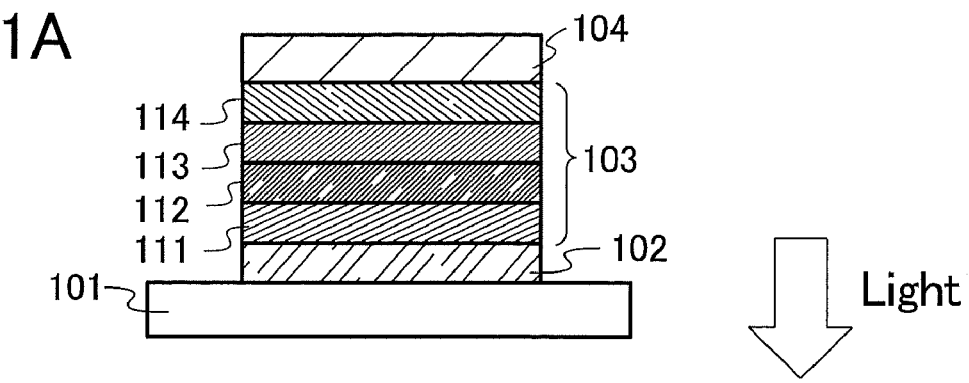
FIGS. 1A to 1C each illustrate a light-emitting element according to an aspect of the present invention.

Hereinafter, embodiment modes of the present invention are described in detail using the accompanying drawings. However, it is easily understood by those skilled in the art that the present invention is not limited to description below and that a variety of changes may be made in modes and details without departing from the spirit and the scope of the present invention. Therefore, the present invention should not be construed as being limited to the description of the embodiment modes given below.

Embodiment Mode 1

Hereinafter, a quinoxaline derivative of the present invention is described. The quinoxaline derivative of the present invention is a quinoxaline derivative represented by the general formula (G1) below.

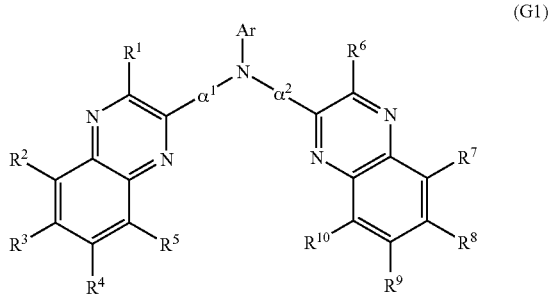

(G1)

In the formula, $\alpha^1$ and $\alpha^2$ each independently represent an arylene group which has 13 or less carbon atoms forming a ring, for example, a divalent group derived from benzene, naphthalene, fluorene, or the like. Such a group may, but not necessarily, have a substituent. If the group has a substituent, an alkyl group having 1 to 6 carbon atoms, a phenyl group, or the like can be used.

Further, in the formula, Ar represents an aryl group which has 13 or less carbon atoms forming a ring. Specifically, a phenyl group, a biphenyl group, a naphthyl group, a fluorenyl group, and the like can be given. Such a group may have a substituent. If the group has a substituent, the group has an alkyl group having 1 to 6 carbon atoms, a phenyl group, a biphenyl group, or the like. These substituents may form a ring by being bonded to each other or by being bonded to Ar.

In the formula, $R^1$ and $R^6$ each independently represent any of a hydrogen atom, an alkyl group having 1 to 6 carbon atoms, a phenyl group, a biphenyl group, a naphthyl group, or a fluorenyl group. The alkyl group having 1 to 6 carbon atoms may form a ring. Further, $R^1$ and $R^6$ may have a substituent. If $R^1$ and $R^6$ have a substituent, an alkyl group having 1 to 6 carbon atoms, a phenyl group, a biphenyl group, and the like can be given as the substituent. If $R^1$ and $R^6$ have these substituents, a substituent of $R^1$ may form a ring by being bonded to $R^1$ or another substituent of $R^1$, and a substituent of $R^6$ may form a ring by being bonded to $R^6$ or another substituent of $R^6$.

Further, in the formula, $R^2$ to $R^5$ and $R^7$ to $R^{10}$ each independently represent any of a hydrogen atom, an alkyl group having 1 to 6 carbon atoms, a phenyl group, or a biphenyl group. The alkyl group having 1 to 6 carbon atoms may form a ring. Further, $R^2$ to $R^5$ and $R^7$ to $R^{10}$ may have a substituent. If $R^2$ to $R^5$ and $R^7$ to $R^{10}$ have a substituent, an alkyl group having 1 to 6 carbon atoms, a phenyl group, a biphenyl group, and the like can be given as the substituent.

Specifically, $\alpha^1$ and $\alpha^2$ in the above general formula (G1) are groups represented by the general formulae (2-1) to (2-7) given below. Note that in the formulae, $R^{11}$ to $R^{15}$ and $R^{21}$ to $R^{36}$ each independently represent any of a hydrogen atom, an alkyl group having 1 to 6 carbon atoms, or a phenyl group; and $R^{37}$ and $R^{38}$ each independently represent a hydrogen atom or an alkyl group having 1 to 6 carbon atoms.

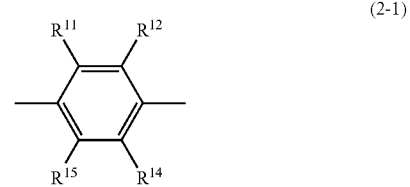

(2-1)

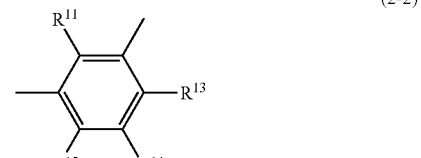

(2-2)

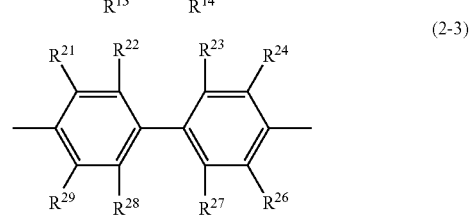

(2-3)

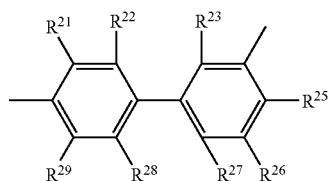

(2-4)

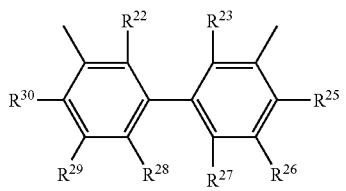

(2-5)

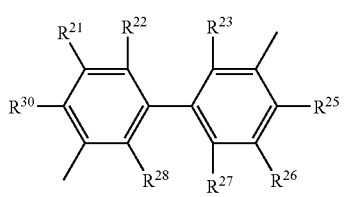

(2-6)

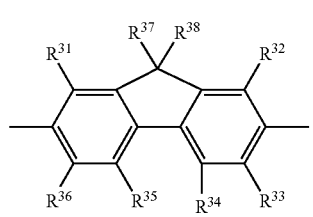

(2-7)

A structure in which $\alpha^1$ and $\alpha^2$ are each independently any of groups represented by the general formulae (2-1) to (2-7) is preferable because a level of phosphorescence becomes higher than that in the case of using a polycyclic condensed ring group such as naphthylene.

Further, Ar in the above general formula (G1) is specifically a group represented by any of the general formulae (3-1) to (3-7) given below. In the formulae, $R^{41}$ to $R^{45}$, $R^{51}$ to $R^{68}$, and $R^{71}$ to $R^{79}$ are substituents for Ar, and each independently represent any of an alkyl group having 1 to 6 carbon atoms, a phenyl group, or a biphenyl group. Further, these substituents may form a ring by being bonded to each other or by being bonded to Ar. For example, when $R^{52}$ and $R^{53}$ in the general formula (3-3) below are bonded to each other to form a ring, Ar becomes a group as represented by a general formula (3-3-1) below. When $R^{72}$ and $R^{73}$ in the general formula (3-7) below are phenyl groups and form a ring, Ar becomes a group as represented by a general formula (3-7-1) below. Note that $R^{41}$ to $R^{45}$, $R^{51}$ to $R^{68}$, and $R^{71}$ to $R^{79}$ may be hydrogen atoms.

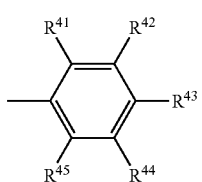

(3-1)

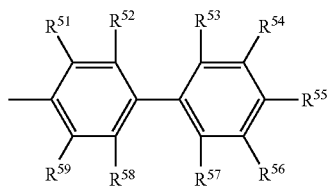

(3-2)

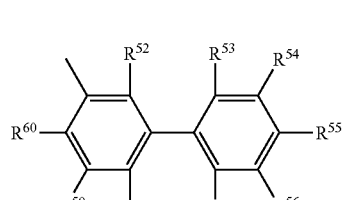

(3-3)

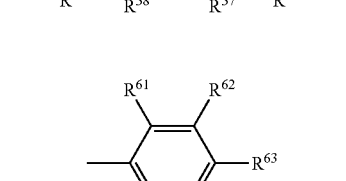

(3-4)

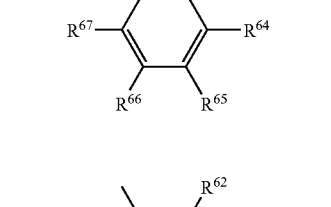

(3-5)

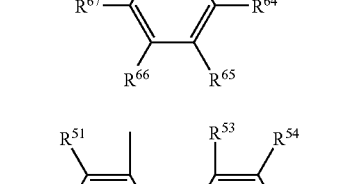

(3-6)

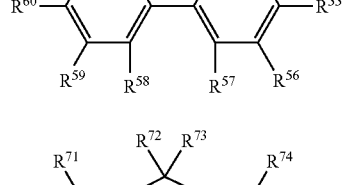

(3-7)

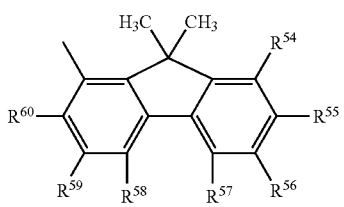

(3-3-1)

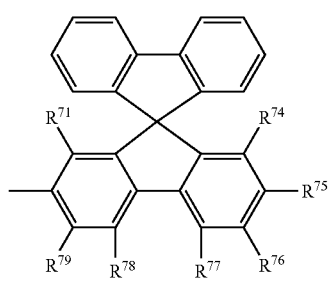
(3-7-1)

A structure in which Ar is any of groups represented by the general formulae (3-1) to (3-7) is preferable because a level of phosphorescence becomes higher than that in the case of using a polycyclic condensed ring group such as naphthylene.

Further, specifically, $R^1$ and $R^6$ in the above general formula (G1) are each independently any of groups represented by the structural formulae (4-1) to (4-6) or general formulae (4-7) to (4-12) given below. Note that in the formulae, $R^{41}$ to $R^{45}$, $R^{51}$ to $R^{68}$, and $R^{71}$ to $R^{79}$ are substituents for $R^1$ and $R^6$, and each independently represent any of an alkyl group having 1 to 6 carbon atoms, a phenyl group, or a biphenyl group. If $R^1$ and $R^6$ have these substituents, a substituent of $R^1$ may form a ring by being bonded to $R^1$ or another substituent of $R^1$, and a substituent of $R^6$ may form a ring by being bonded to $R^6$ or another substituent of $R^6$. Note that $R^{41}$ to $R^{45}$, $R^{51}$ to $R^{68}$, and $R^{71}$ to $R^{79}$ may be hydrogen atoms.

 (4-1)
 (4-2)
 (4-3)
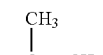 (4-4)
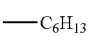 (4-5)
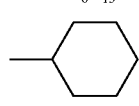 (4-6)
 (4-7)
 (4-8)
 (4-9)

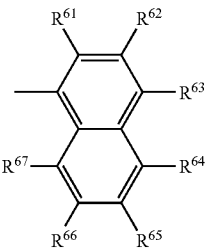 (4-10)

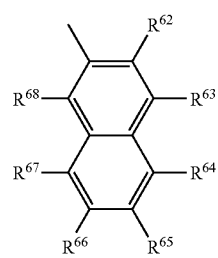 (4-11)

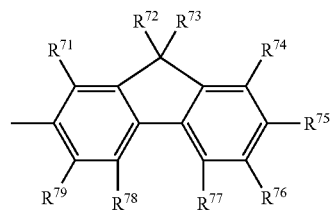 (4-12)

Further, specifically, $R^2$ to $R^5$ and $R^7$ to $R^{10}$ in the above general formula (G1) are each independently represented by any of the structural formulae (5-1) to (5-6) or general formulae (5-7) to (5-10) given below. Note that in the formulae, $R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

 (5-1)
 (5-2)
 (5-3)
 (5-4)
 (5-5)
 (5-6)
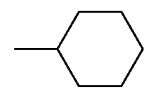
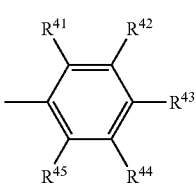 (5-7)

-continued (5-8)
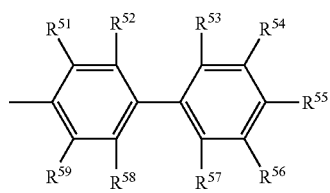

(5-9)
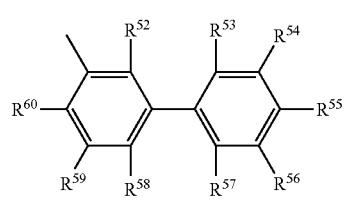

-continued (5-10)
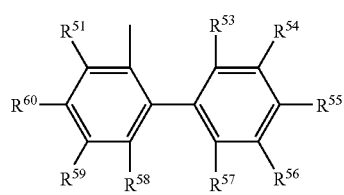

Note that $R^{11}$ to $R^{15}$, $R^{21}$ to $R^{36}$, $R^{41}$ to $R^{45}$, $R^5$ to $R^{68}$, and $R^{71}$ to $R^{79}$ may each independently have a substituent. In this case, $R^{11}$ to $R^{15}$, $R^{21}$ to $R^{36}$, $R^{41}$ to $R^{45}$, $R^{51}$ to $R^{68}$, and $R^{71}$ to $R^{79}$ each independently have an alkyl group having 1 to 6 carbon atoms or a phenyl group.

As specific examples of the quinoxaline derivative represented by the general formula (G1), there are quinoxaline derivatives represented by structural formulae (1) to (124) given below. However, the present invention is not limited to these examples.

(1)
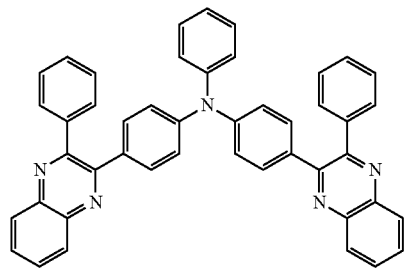

(2)
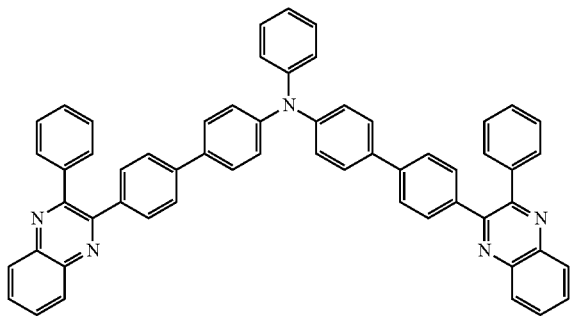

(3)
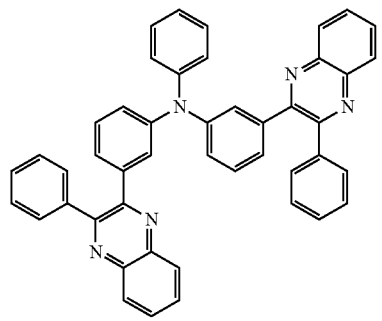

(4)
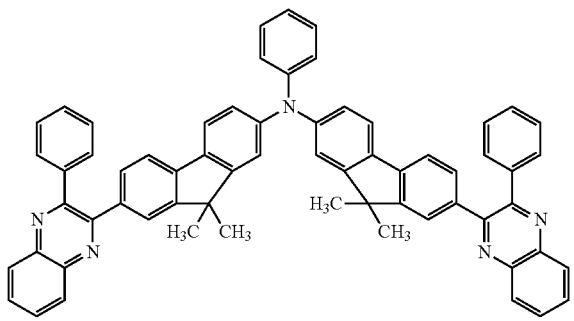

(5)
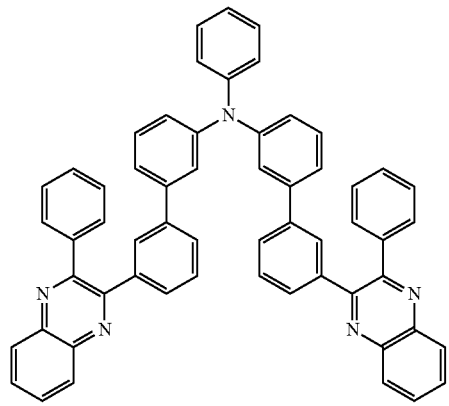

(6)
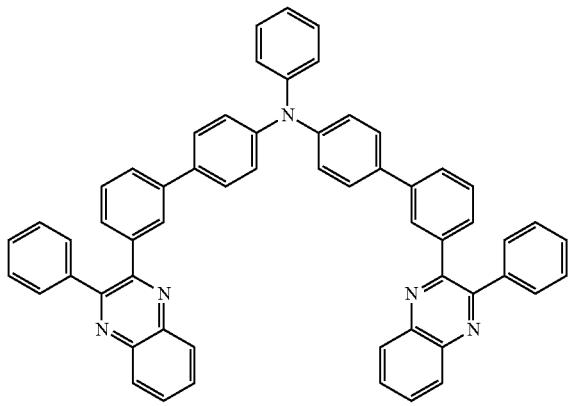

(7)
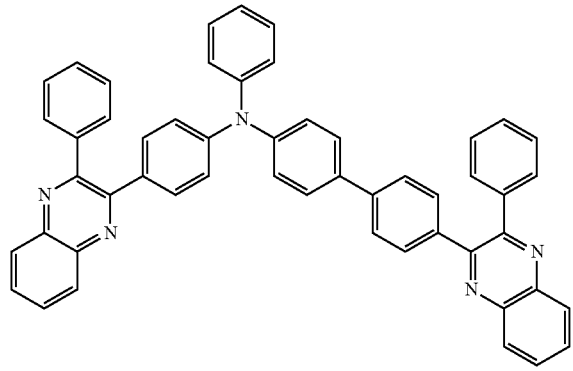
(8)
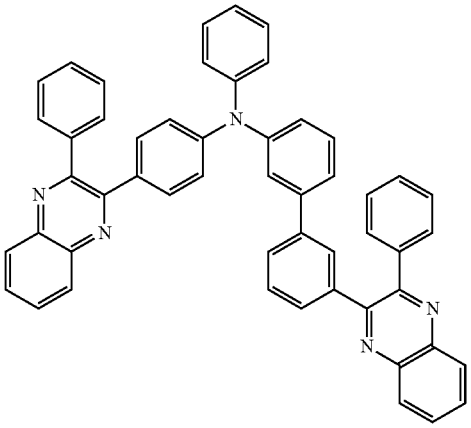
(9)
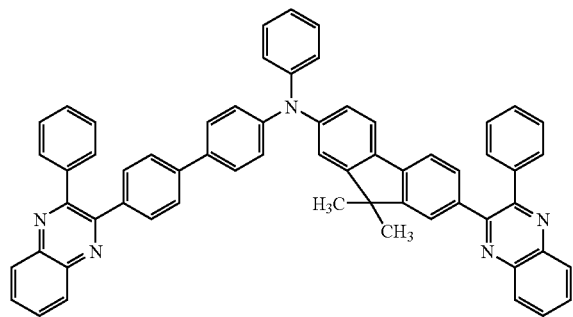
(10)
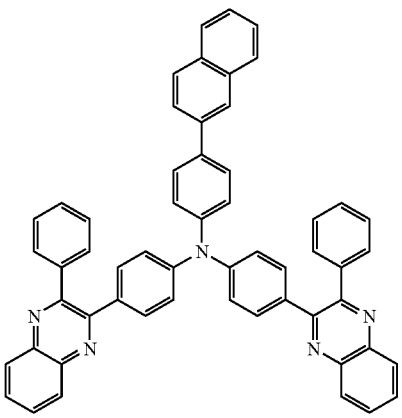
(11)
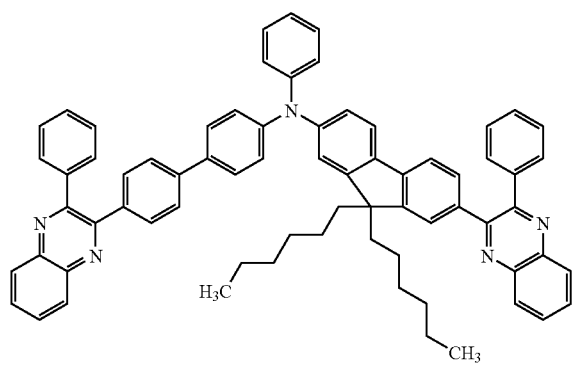
(12)
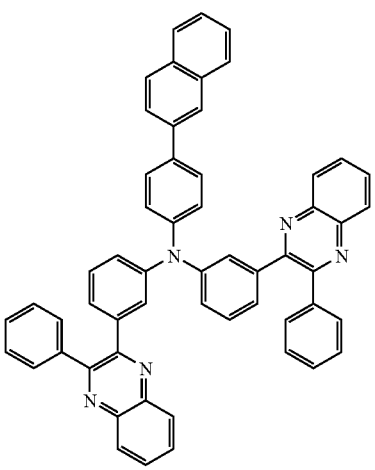

-continued
(13)
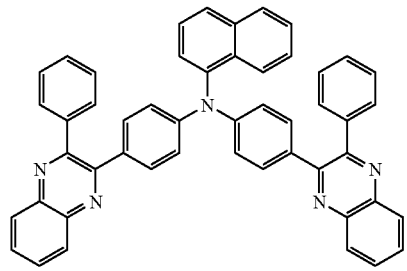
(14)
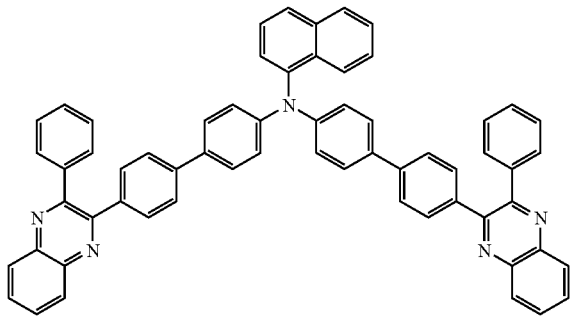
(15)
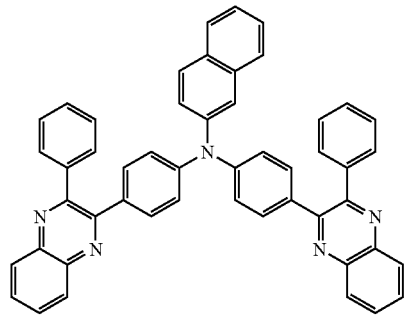
(16)
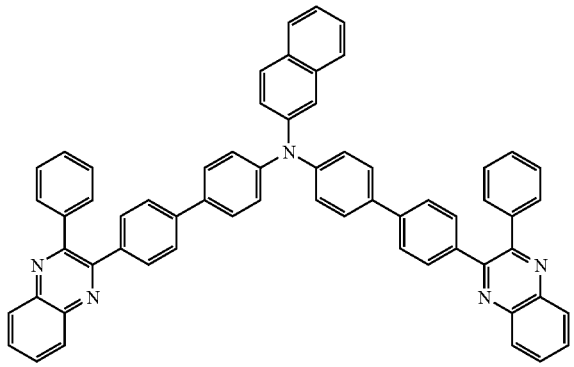
(17)
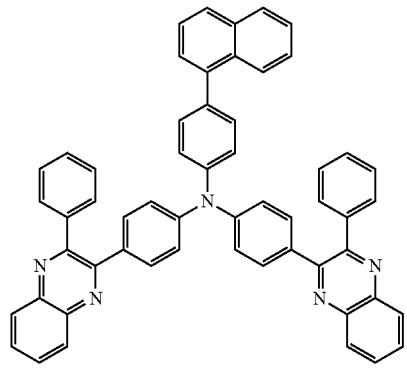
(18)
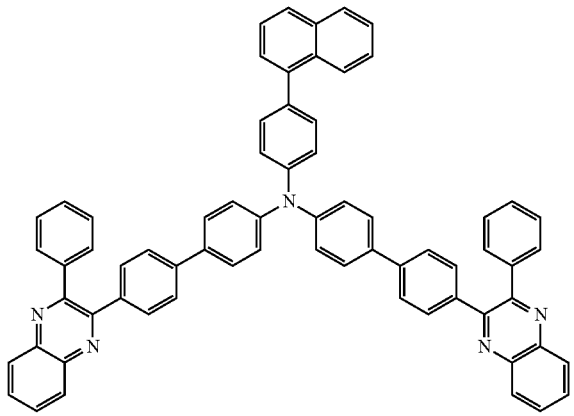
(19)
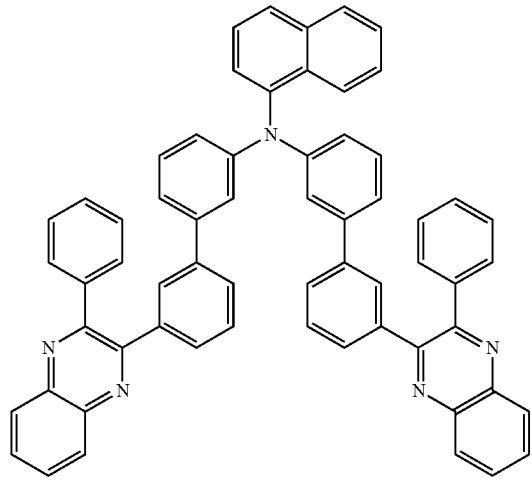
(20)
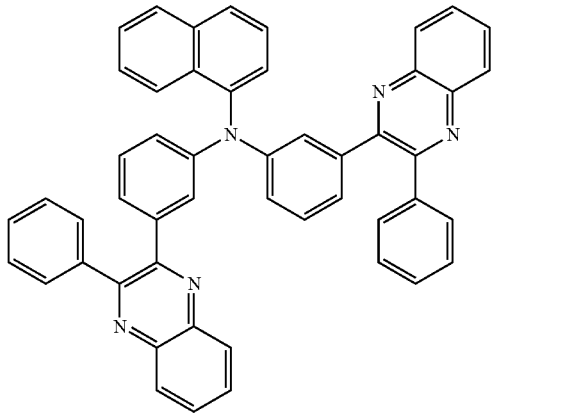

-continued
(21)
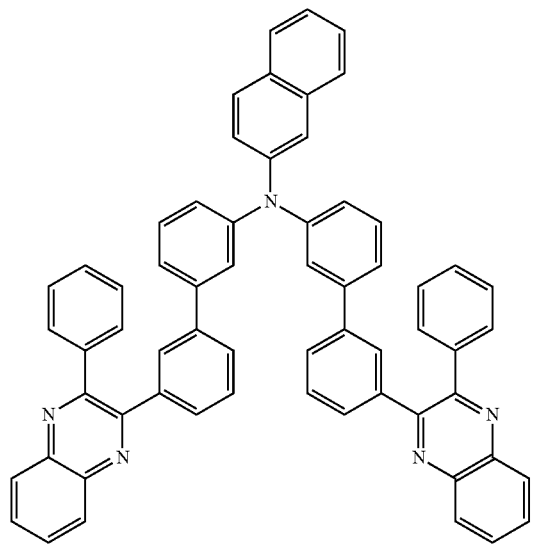
(22)
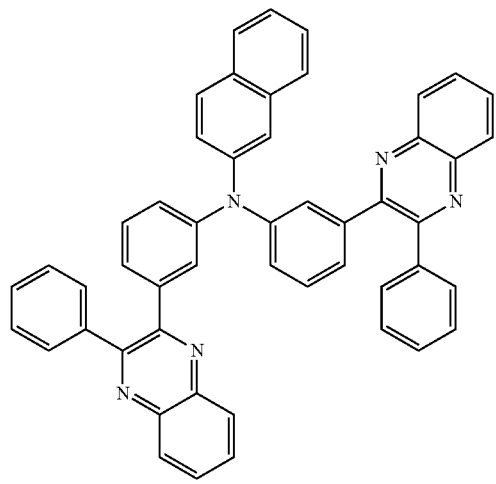
(23)
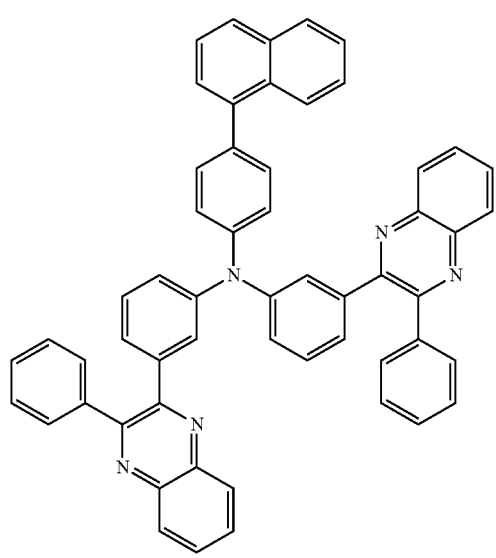
(24)
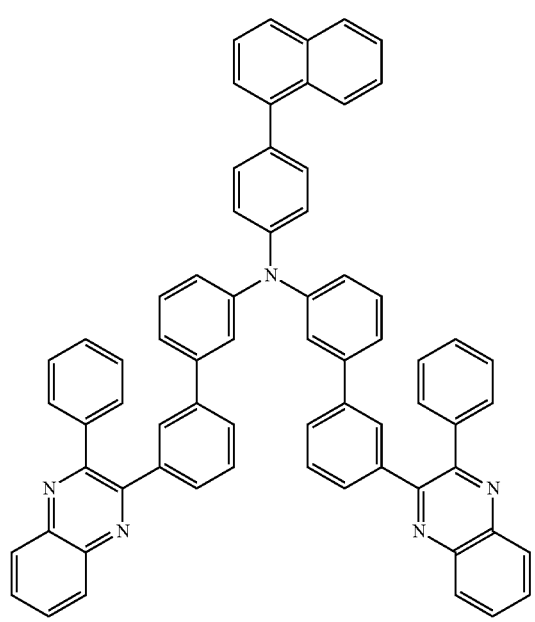
(25)
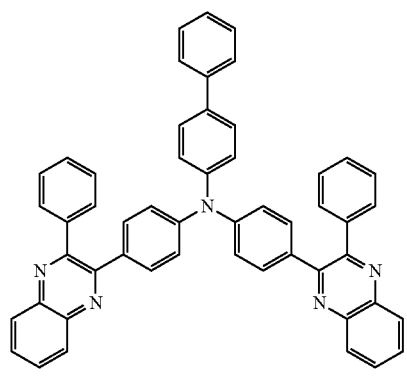
(26)
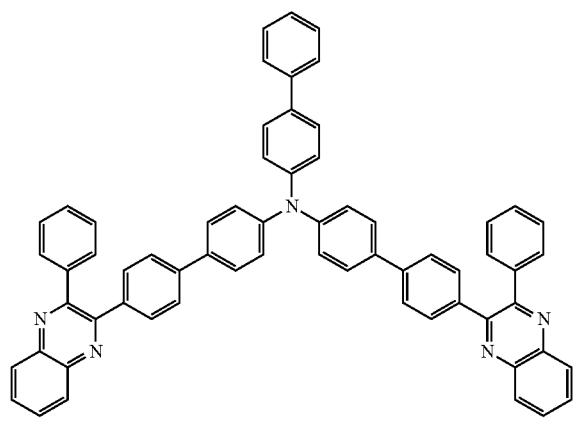

(27)
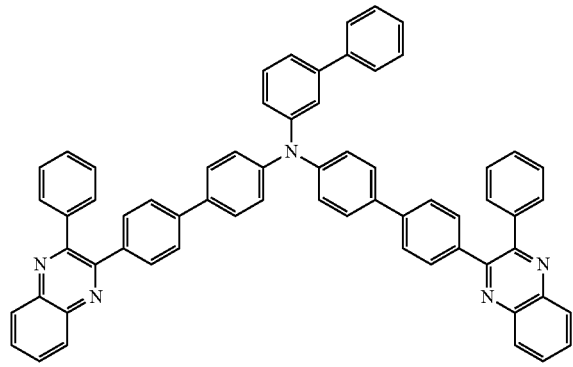
(28)
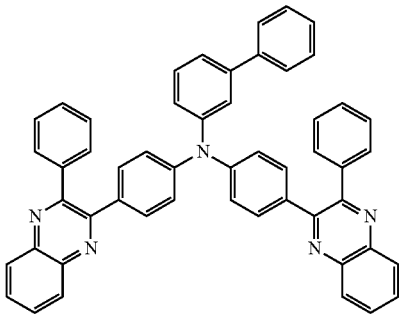
(29)
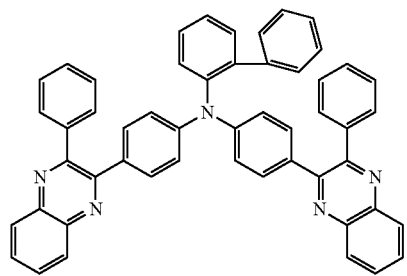
(30)
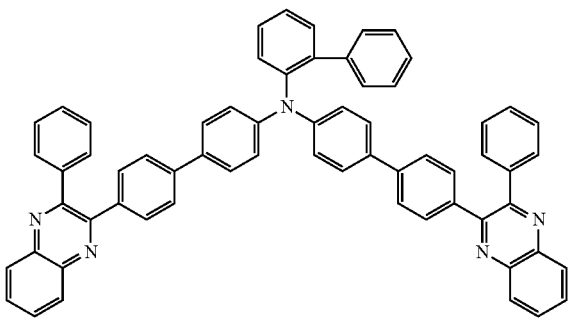
(31)
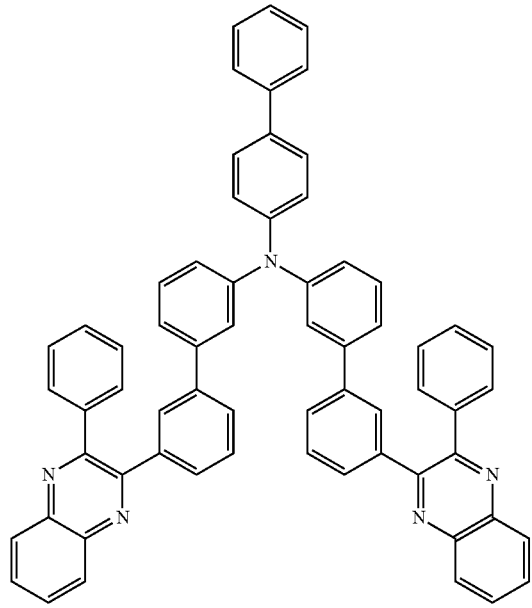
(32)
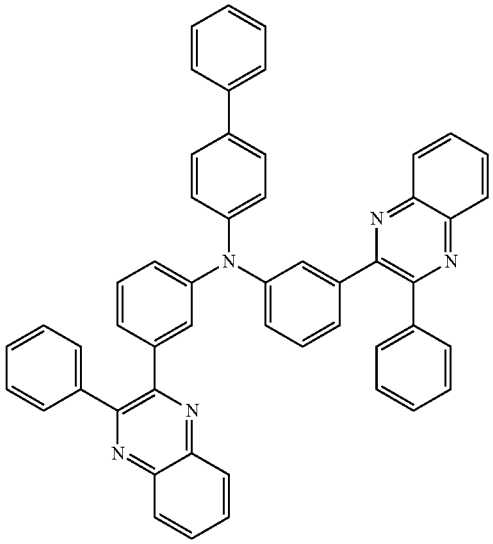

(33)
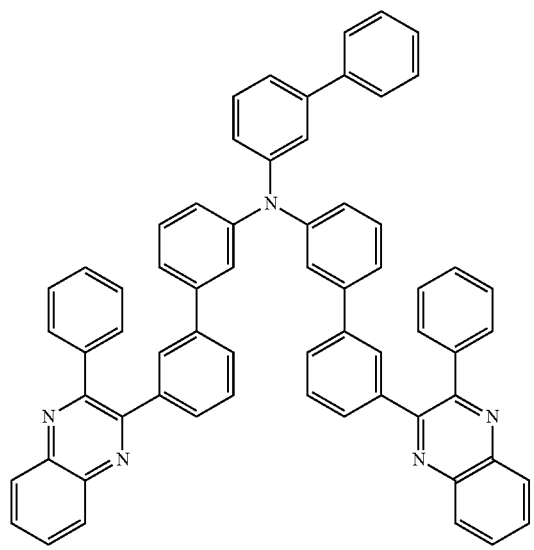
(34)
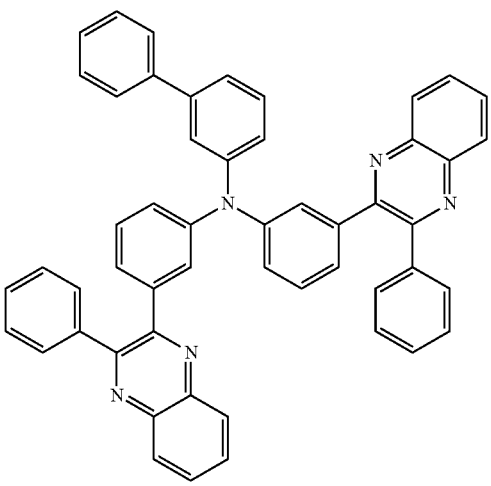
(35)
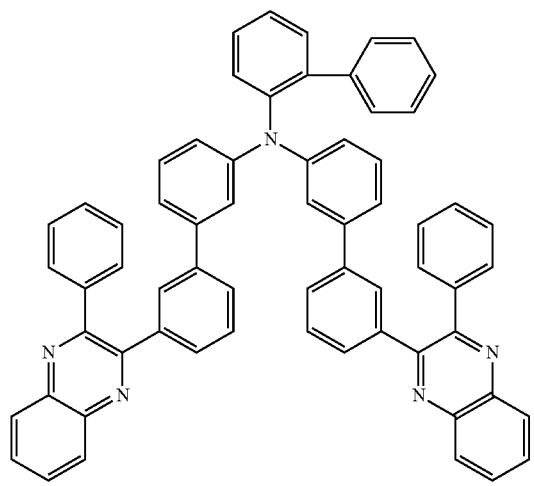
(36)
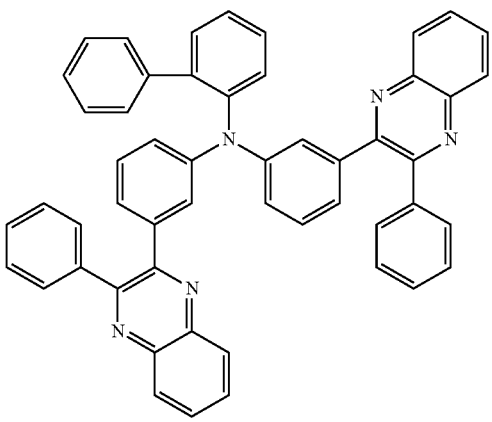
(37)
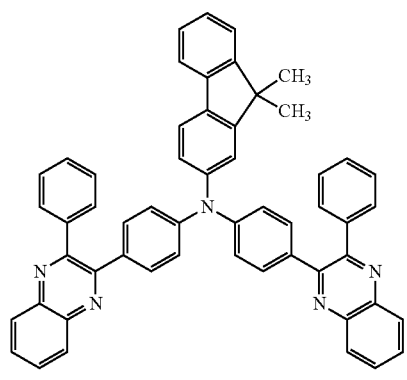
(38)
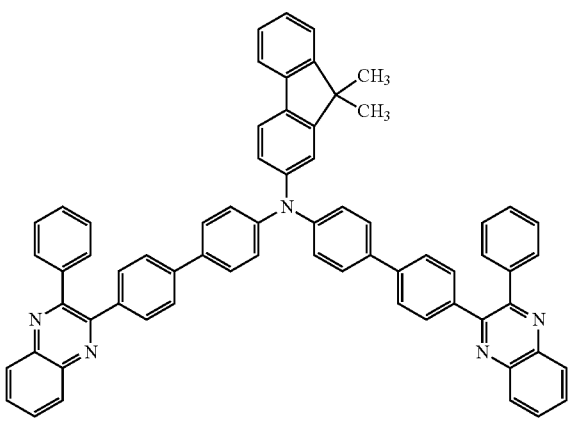

(39)
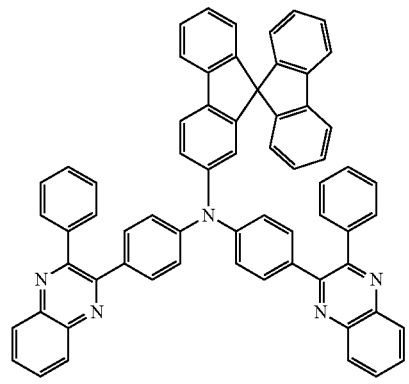
(40)
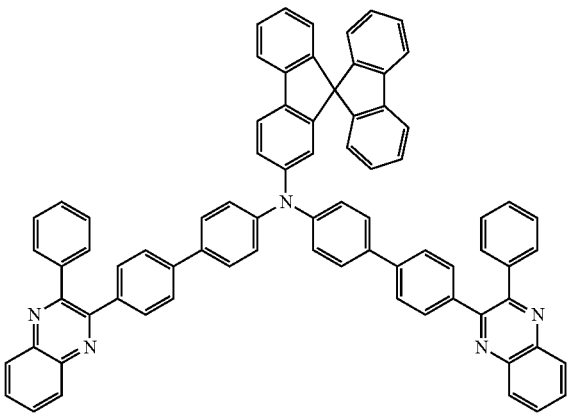
(41)
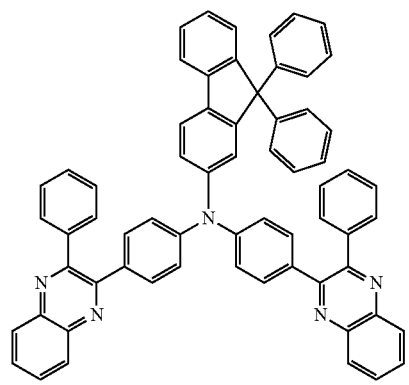
(42)
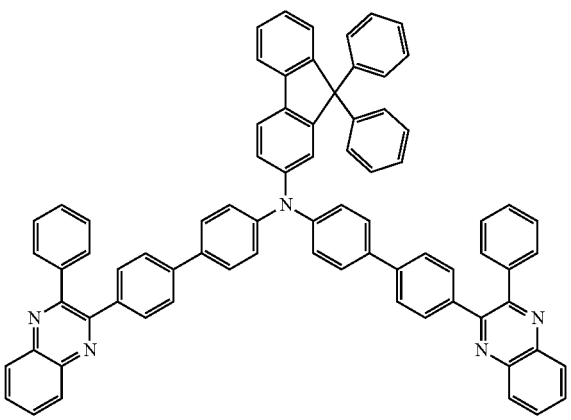
(43)
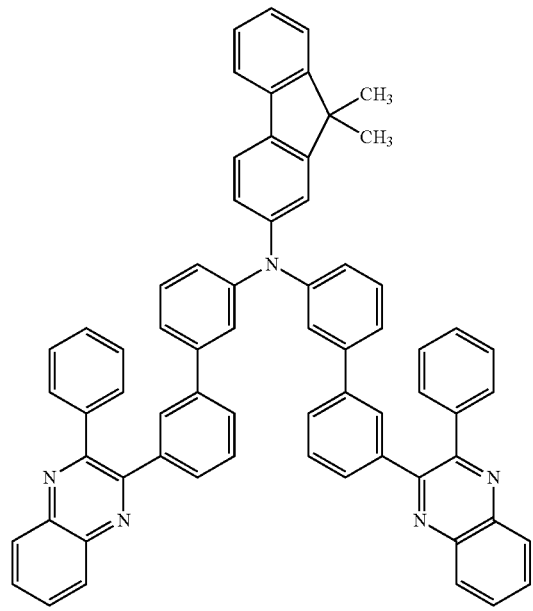
(44)
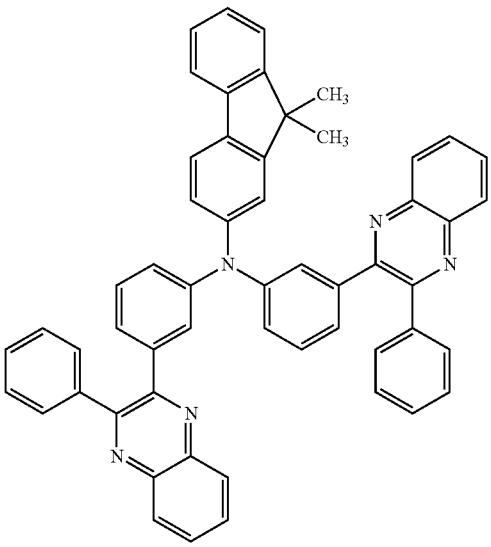

-continued
(45)
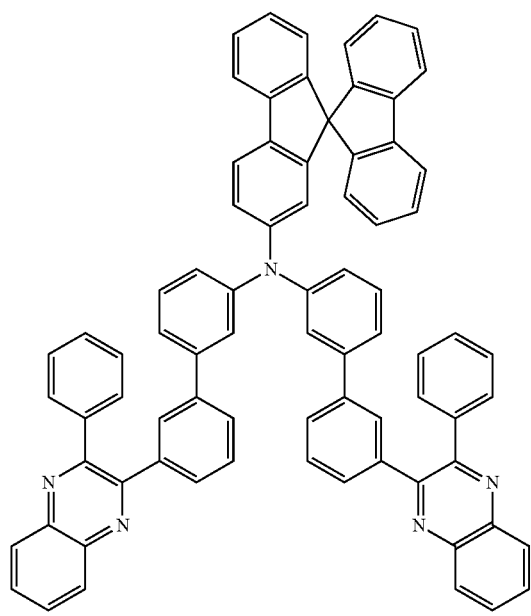
(46)
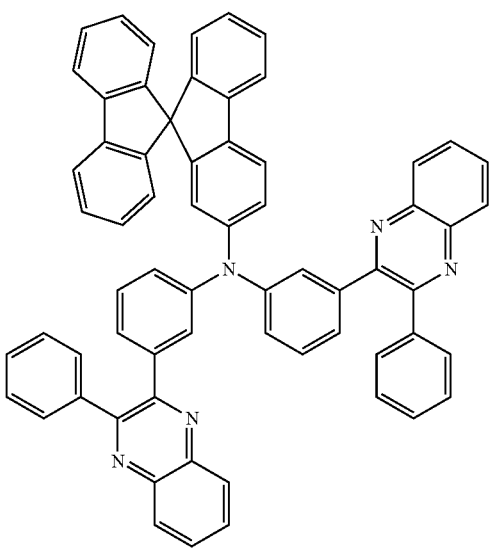
(47)
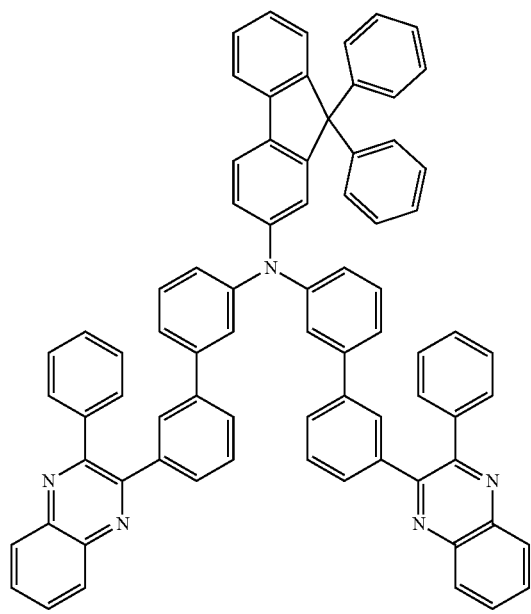
(48)
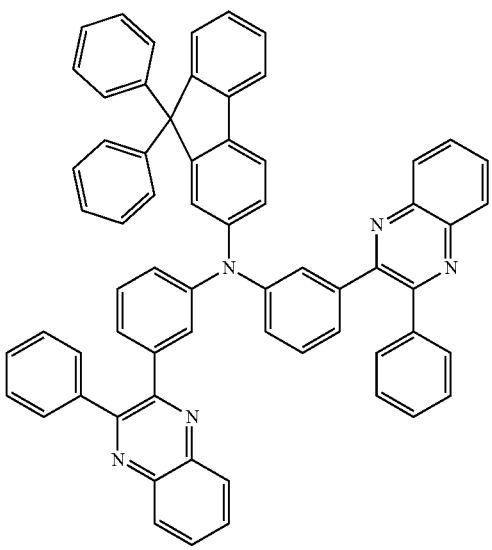
(49)
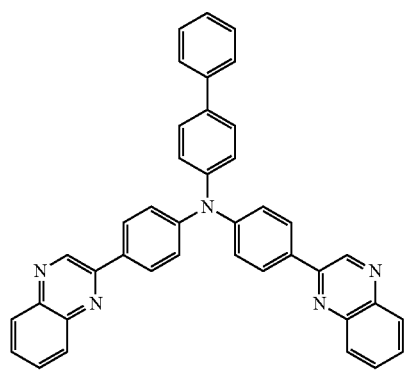
(50)
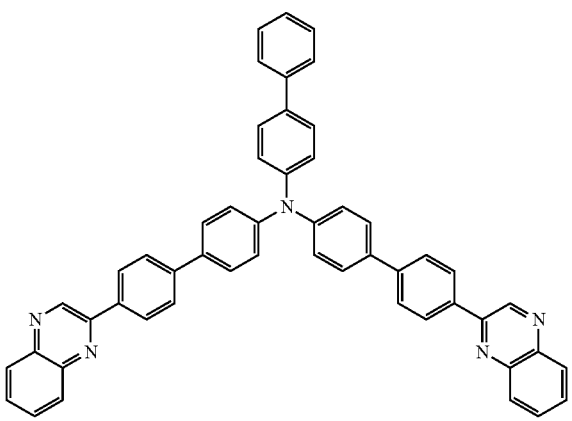

(51)
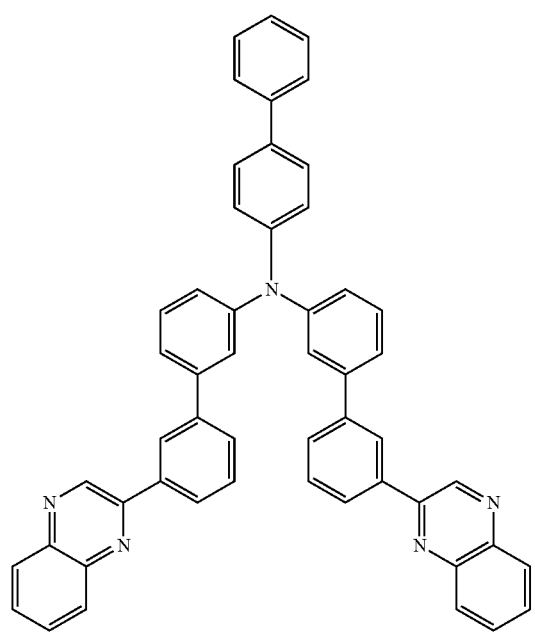
(52)
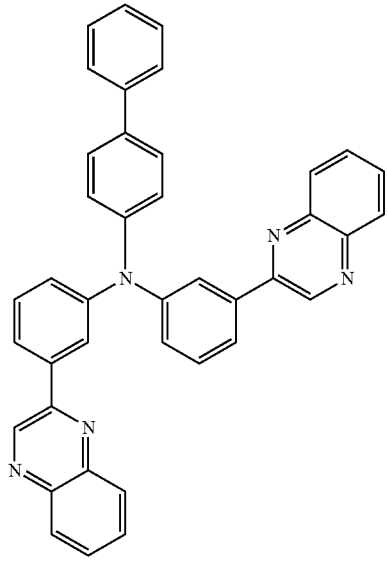
(53)
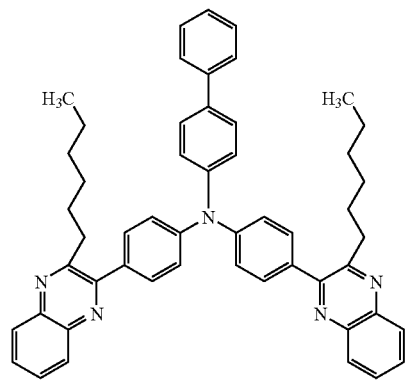
(54)
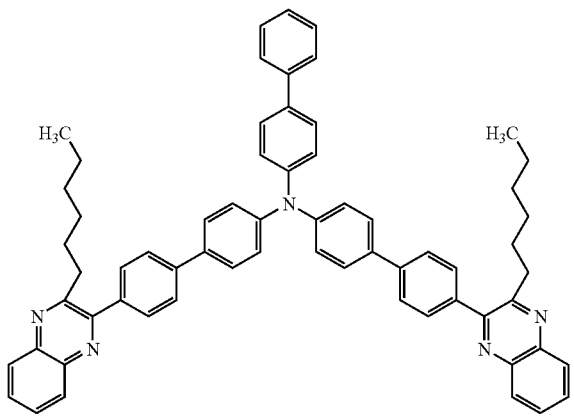
(55)
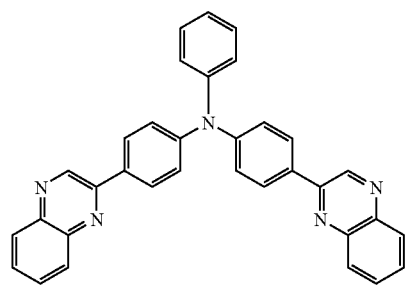
(56)
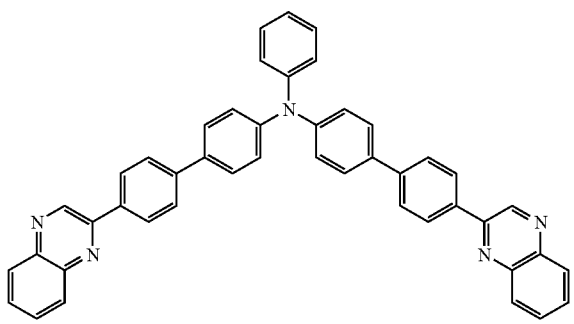

(57)
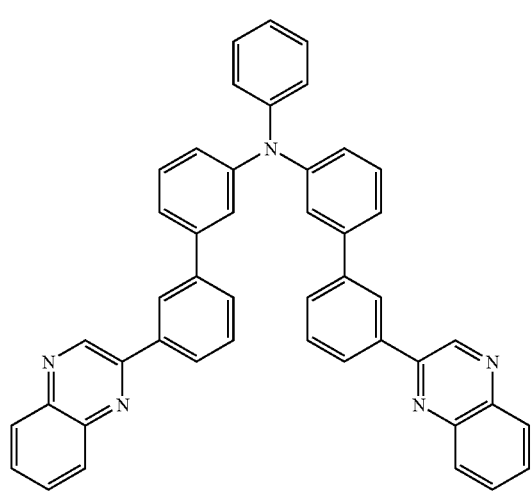
(58)
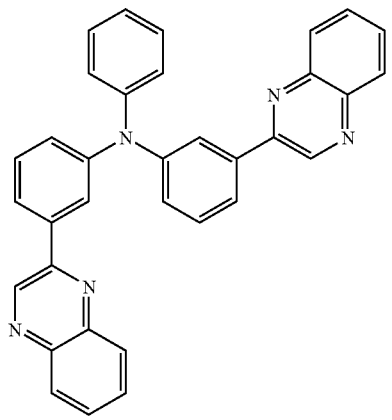
(59)
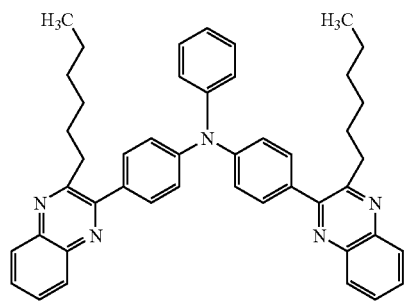
(60)
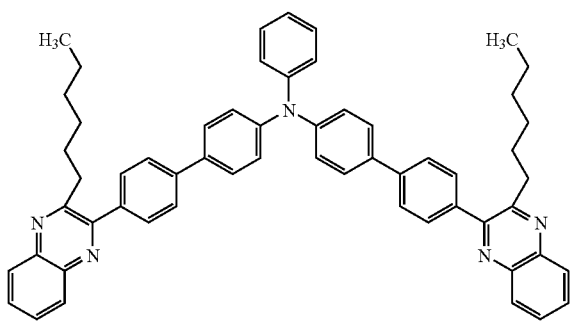
(61)
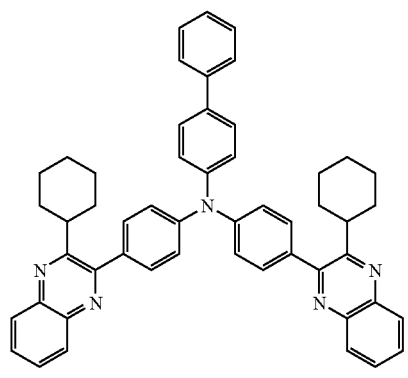
(62)
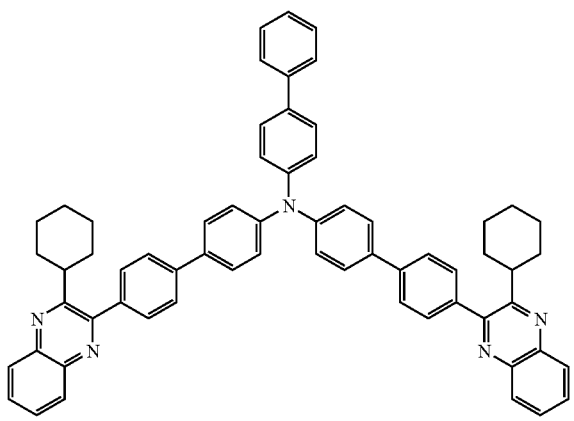

-continued
(63)
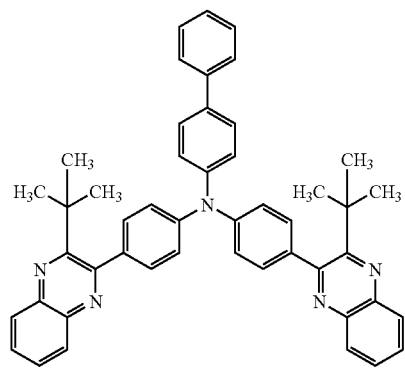
(64)
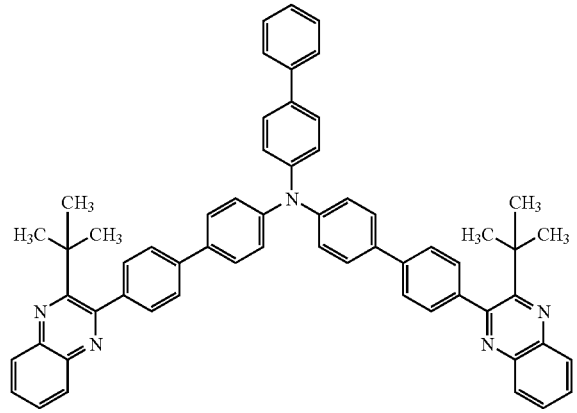
(65)
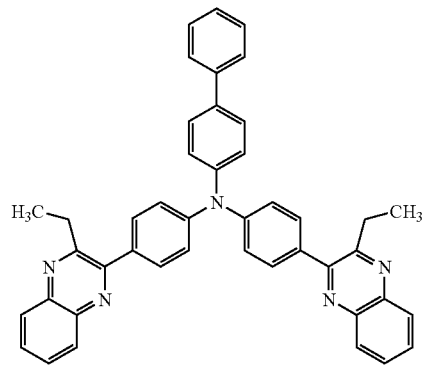
(66)
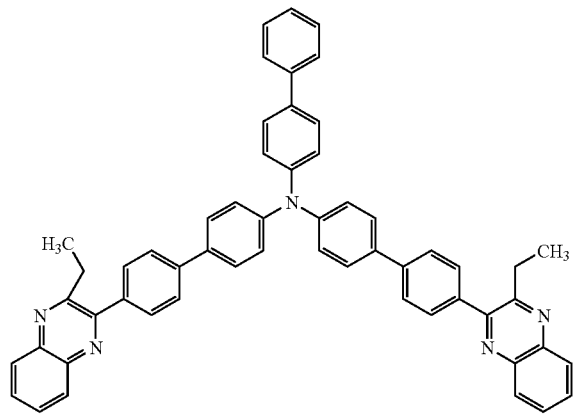
(67)
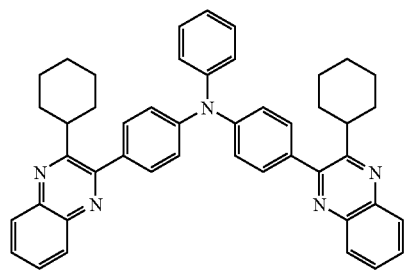
(68)
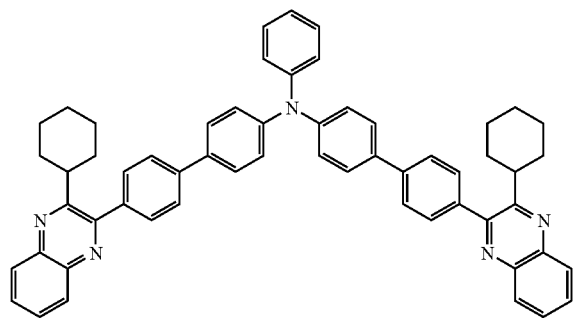
(69)
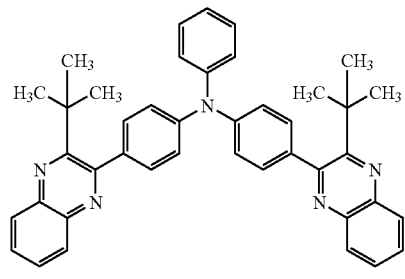
(70)
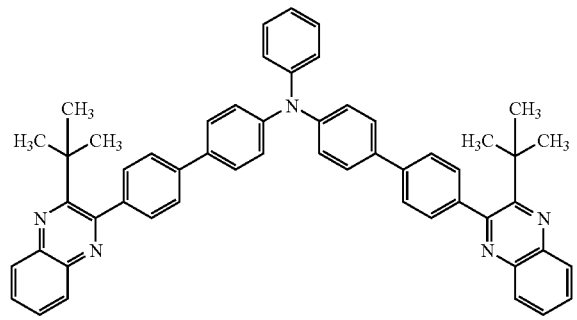

-continued
(71)
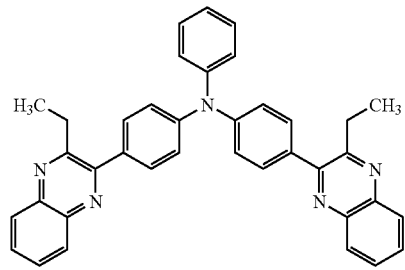
(72)
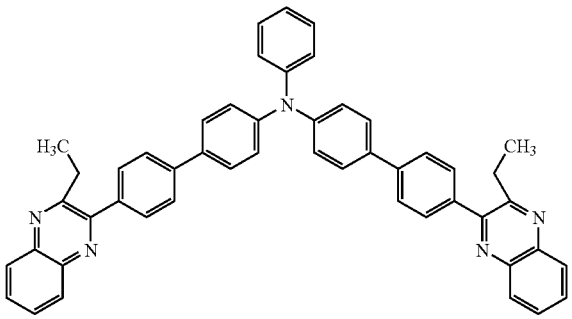
(73)
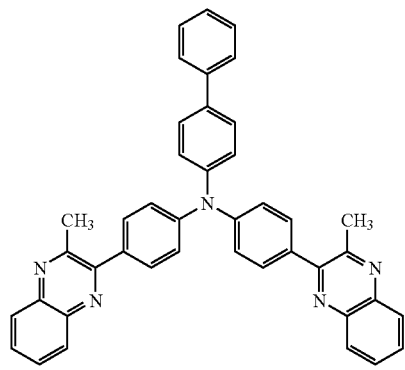
(74)
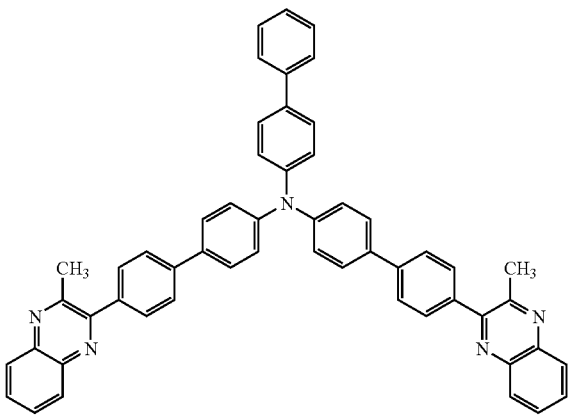
(75)
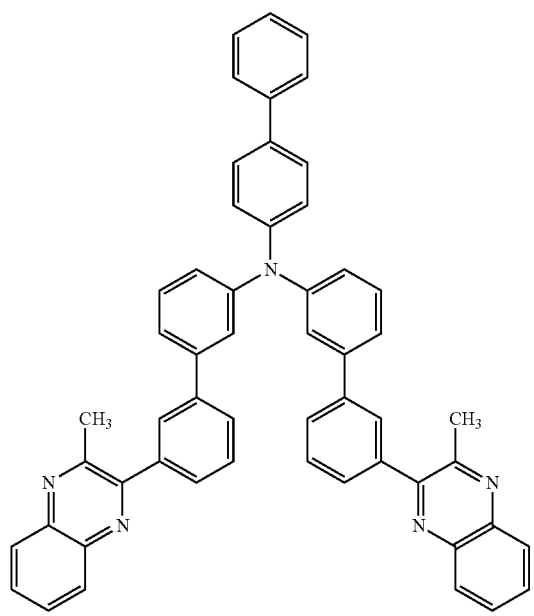
(76)
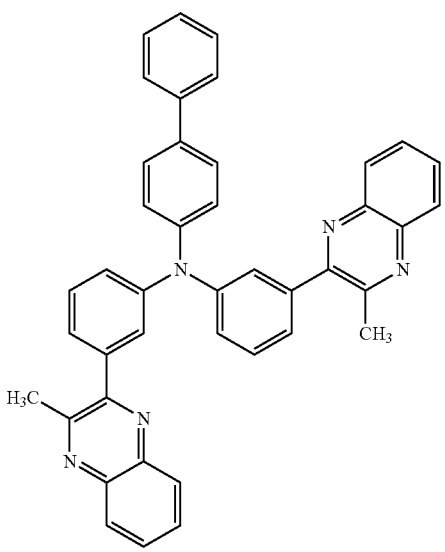

-continued
(77)
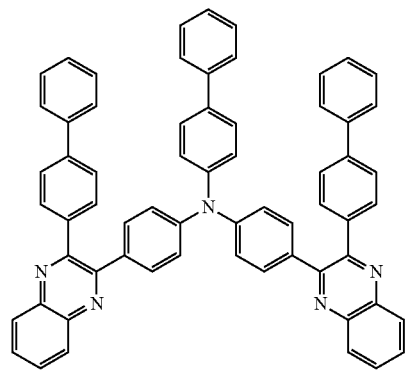
(78)
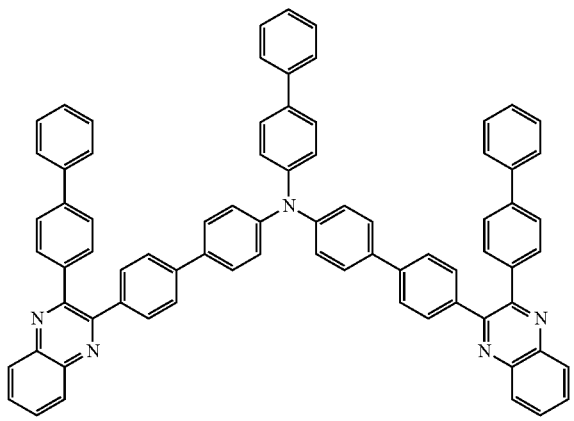
(79)
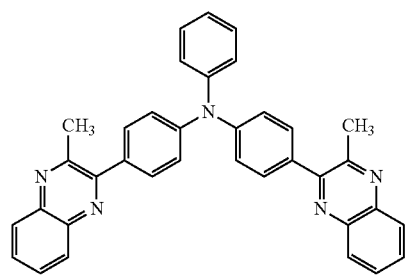
(80)
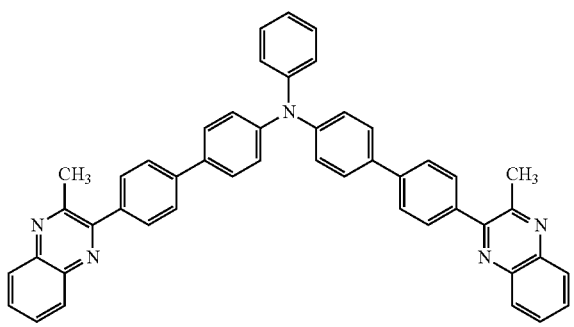
(81)
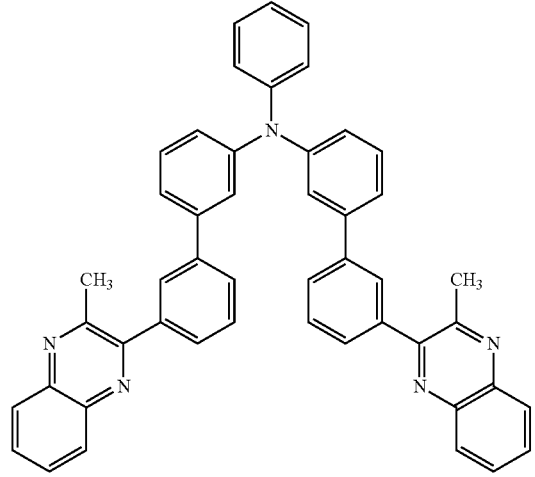
(82)
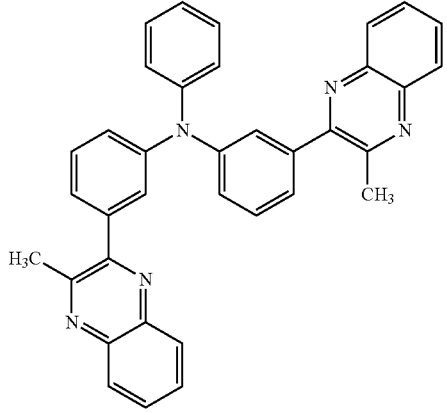
(83)
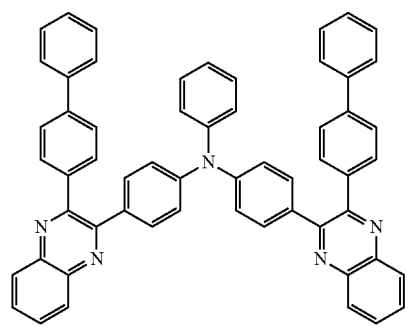
(84)
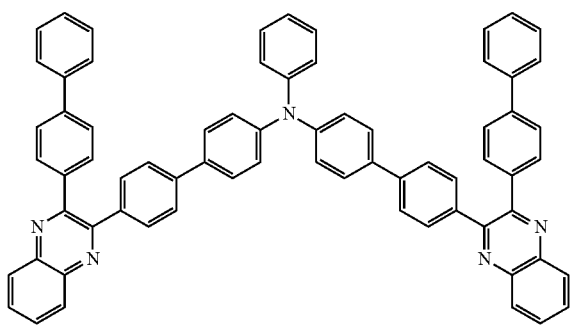

-continued
(85)
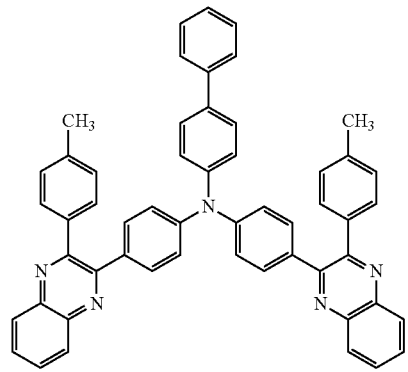
(86)
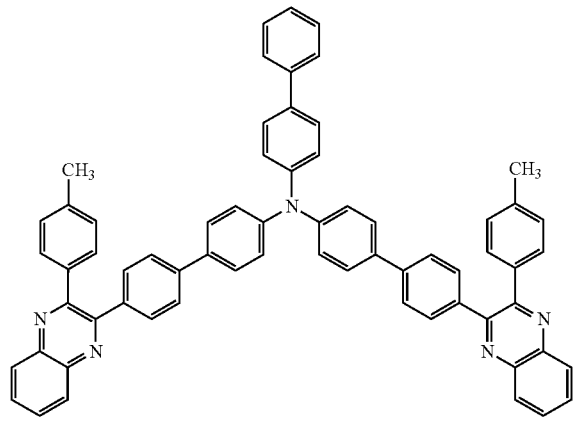
(87)
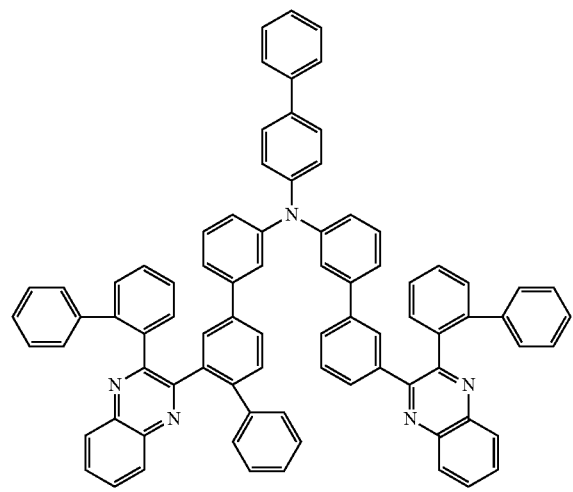
(88)
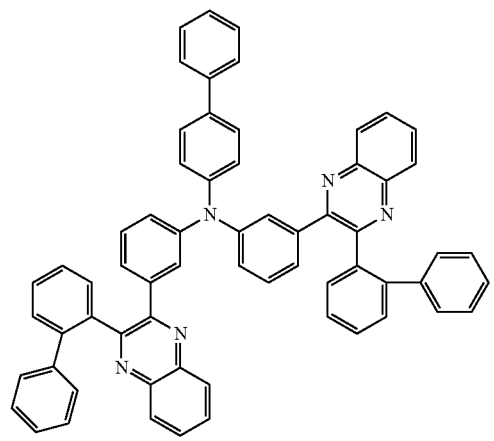
(89)
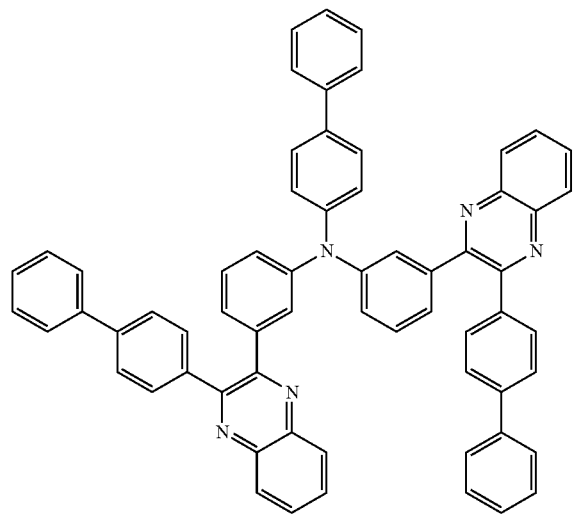
(90)
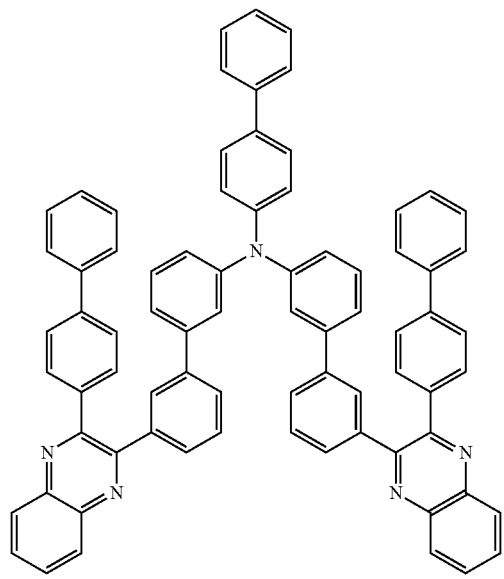

-continued
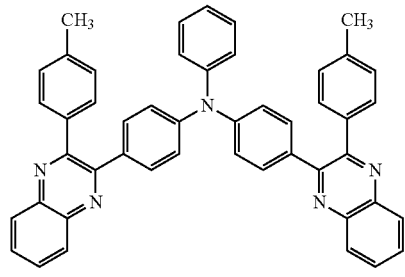
(91)
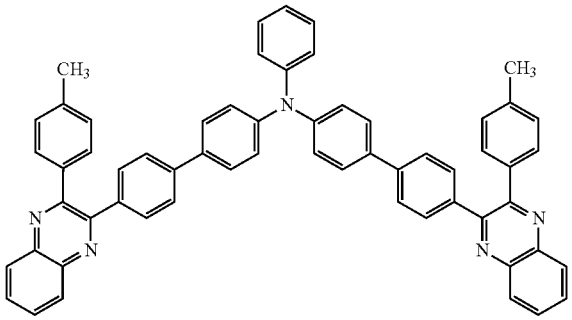
(92)
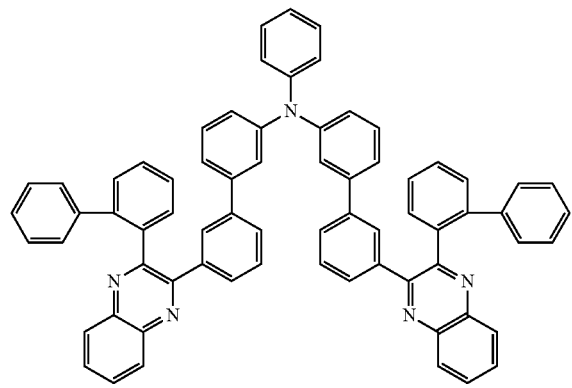
(93)
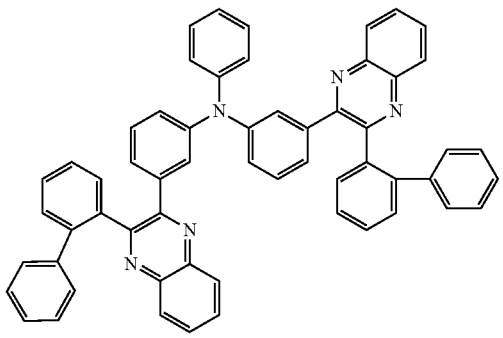
(94)
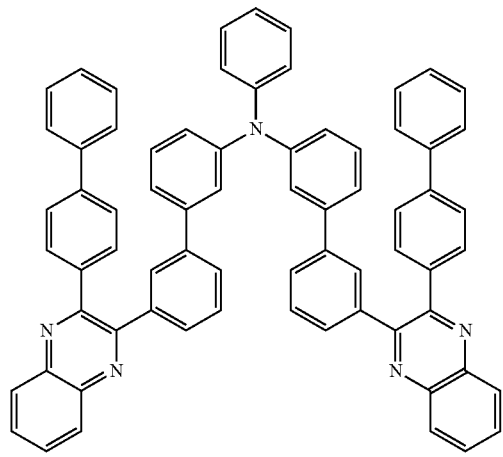
(95)
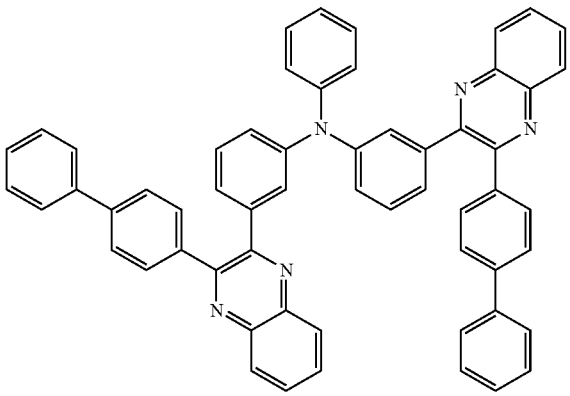
(96)

(97)
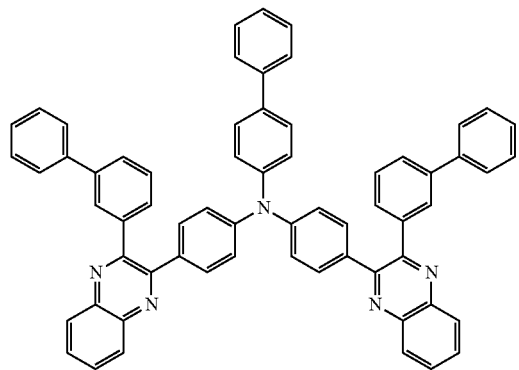
(98)
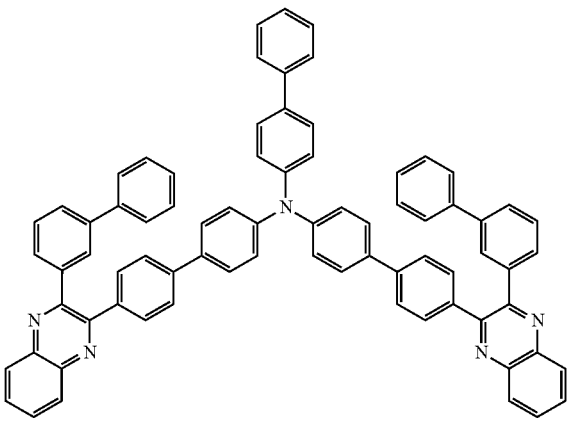
(99)
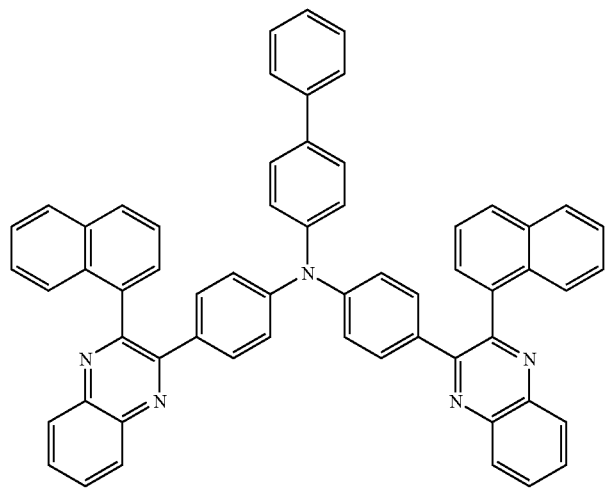
(100)
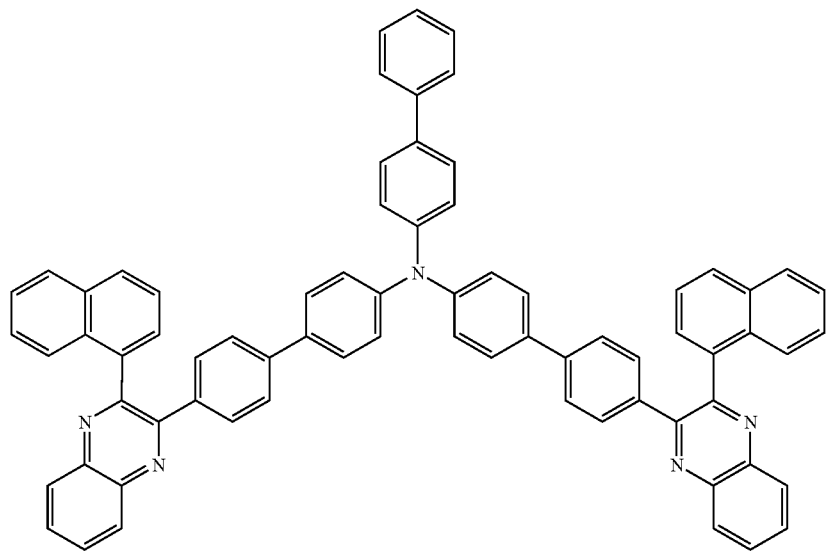

-continued
(101)
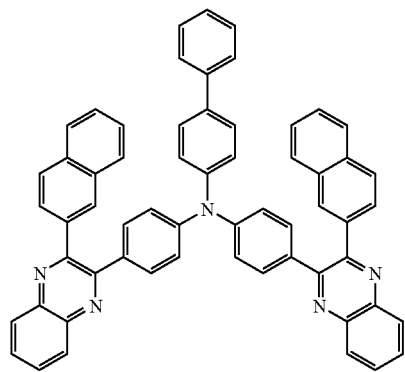
(102)
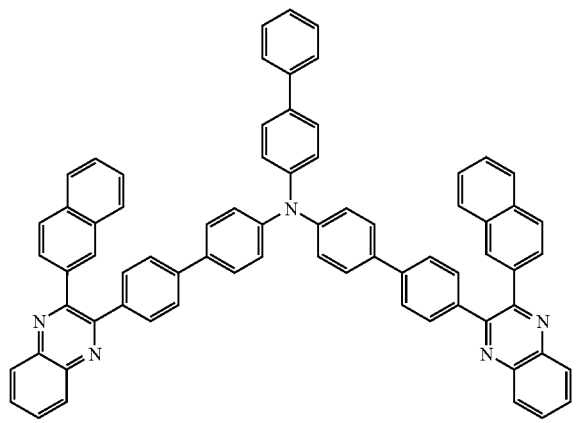
(103)
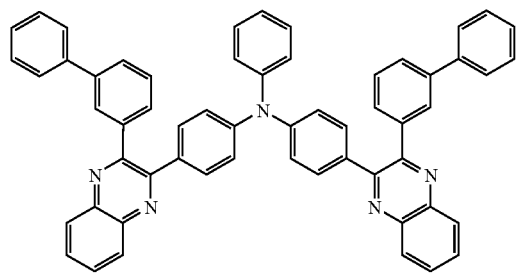
(104)
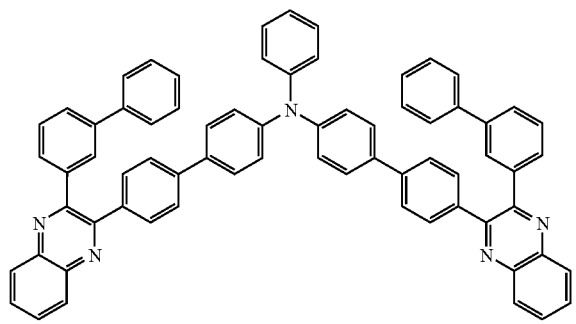
(105)
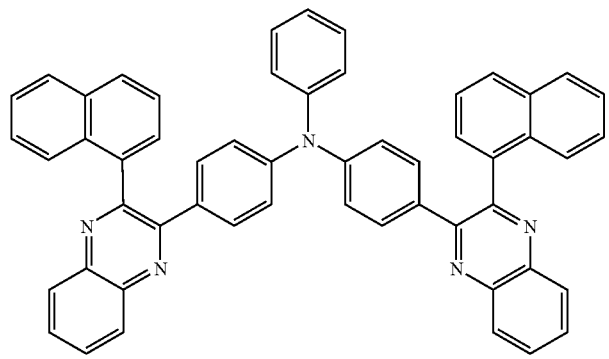
(106)
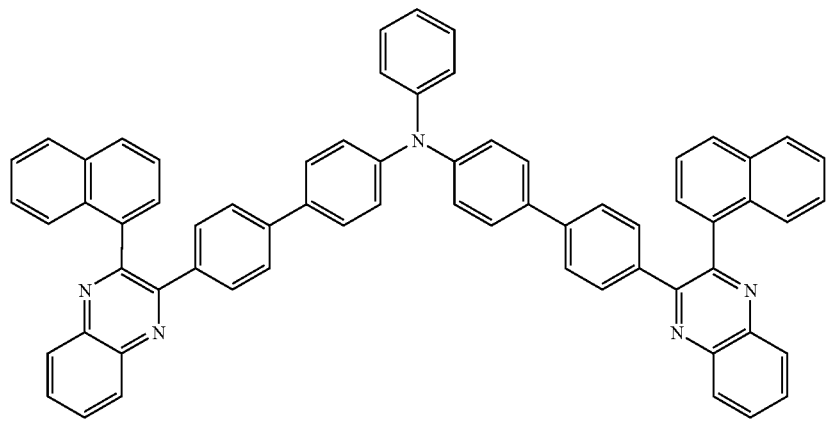

(107)
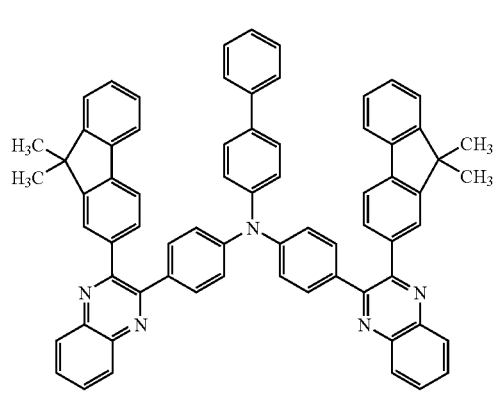
(108)
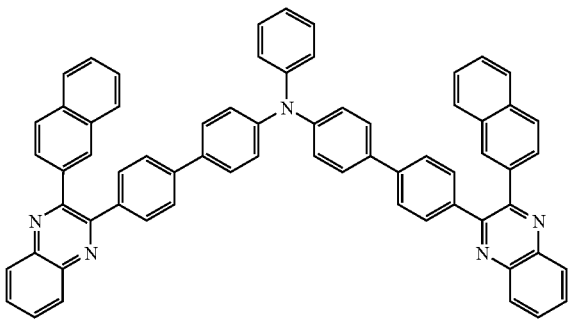
(109)
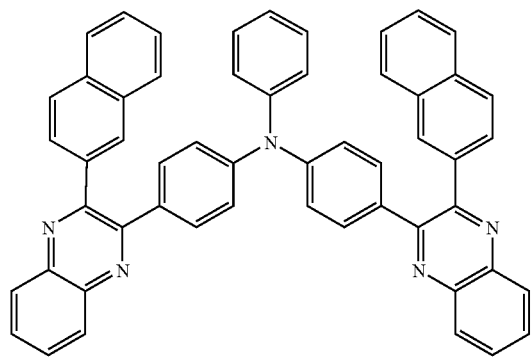
(110)
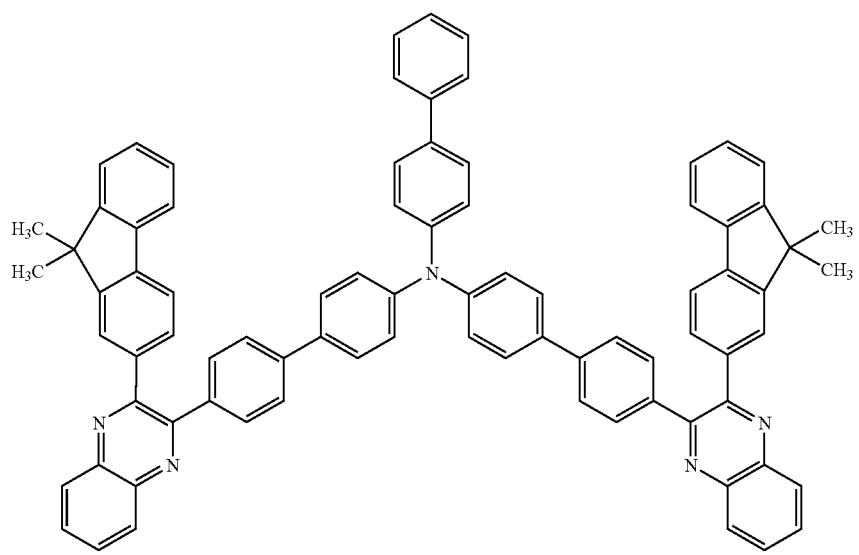

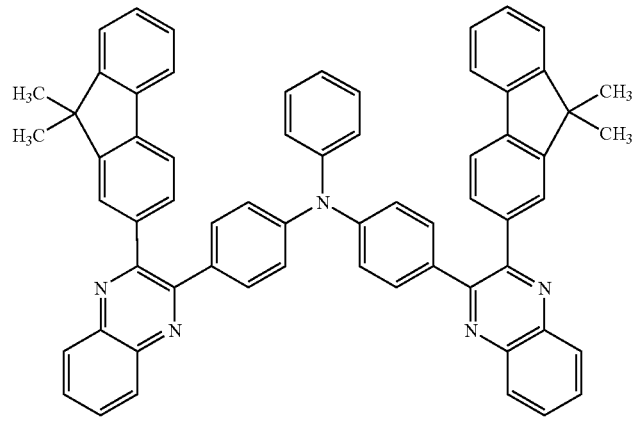
(111)
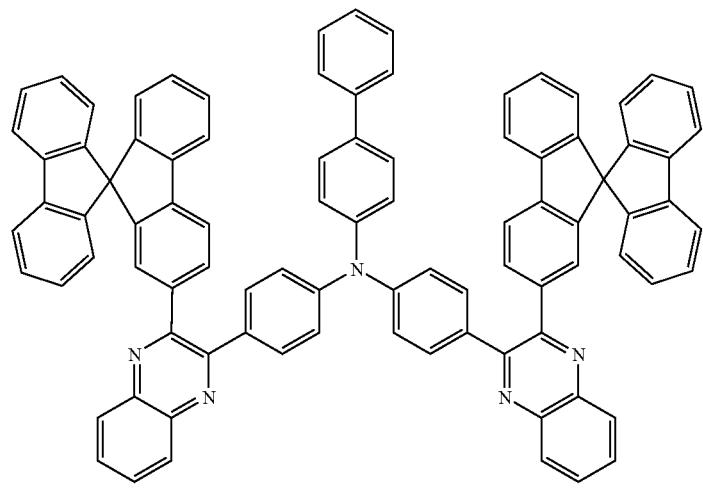
(112)
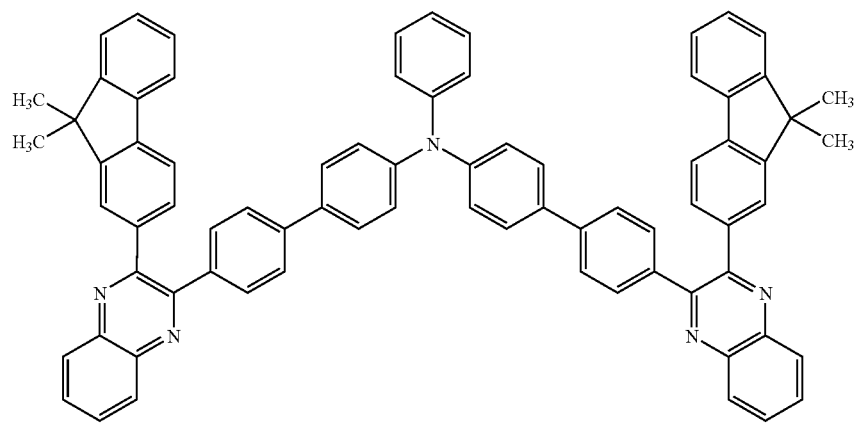
(113)

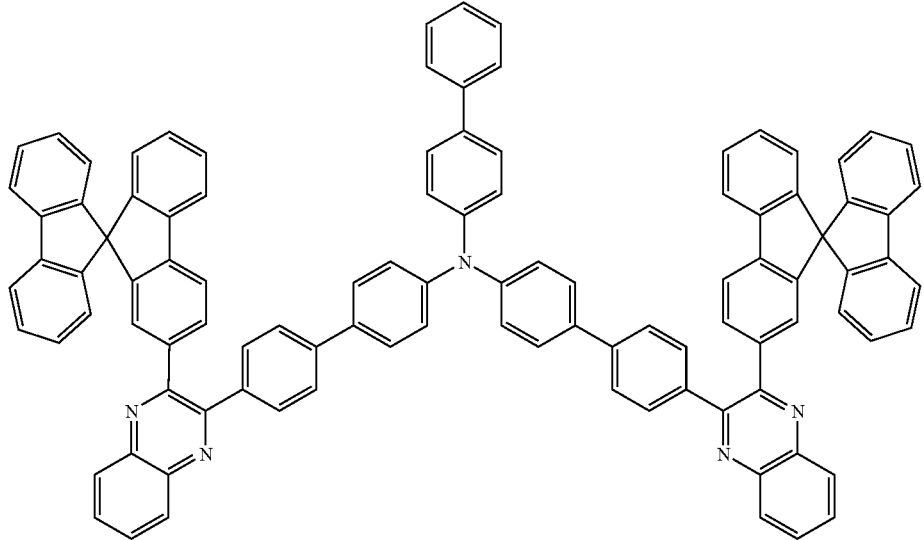
(114)
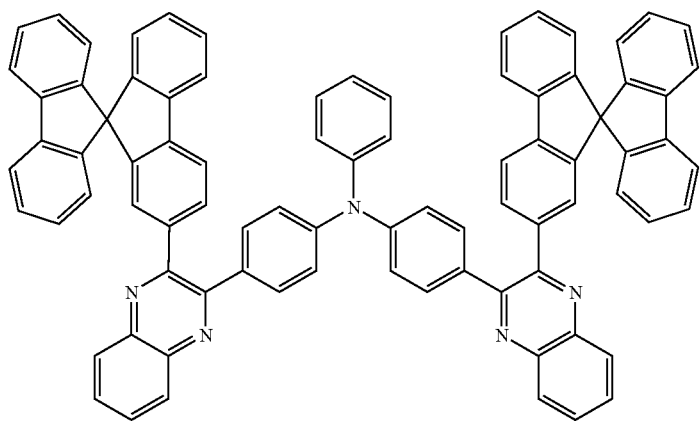
(115)
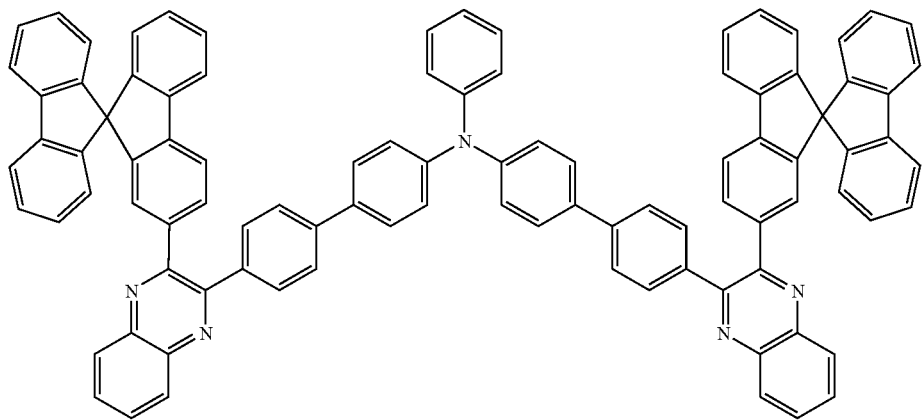
(116)

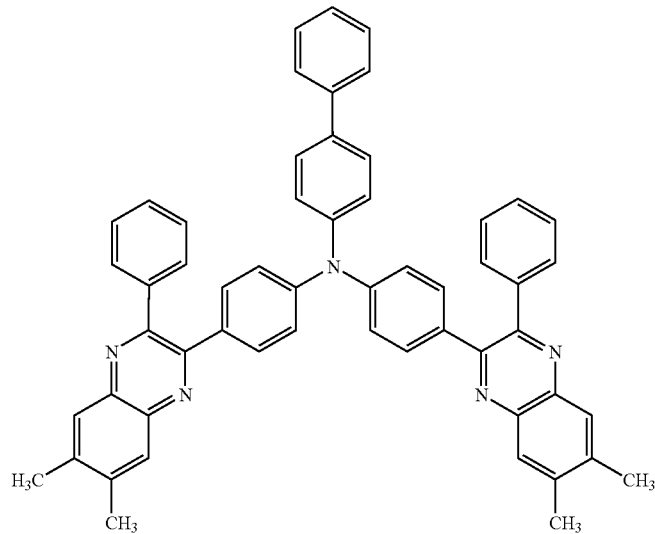
(117)
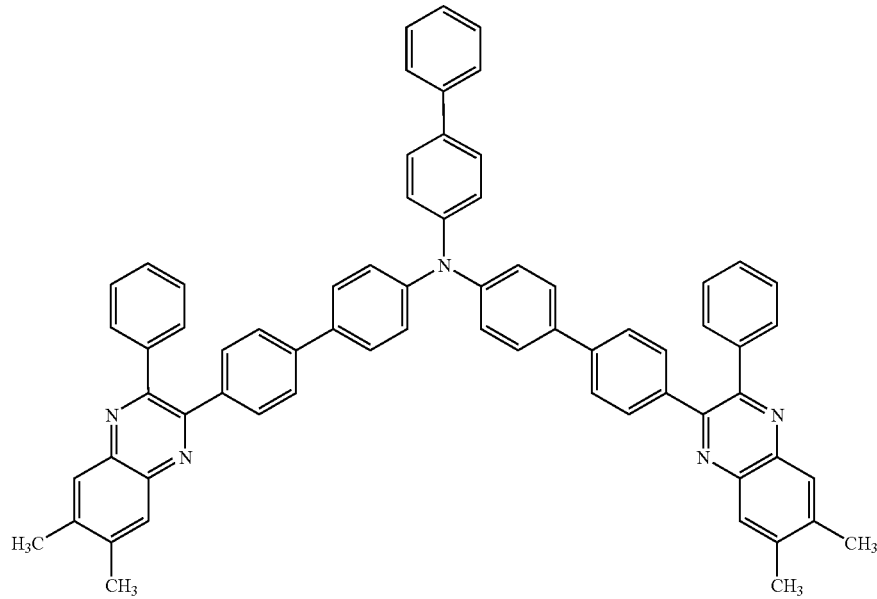
(118)

(119)
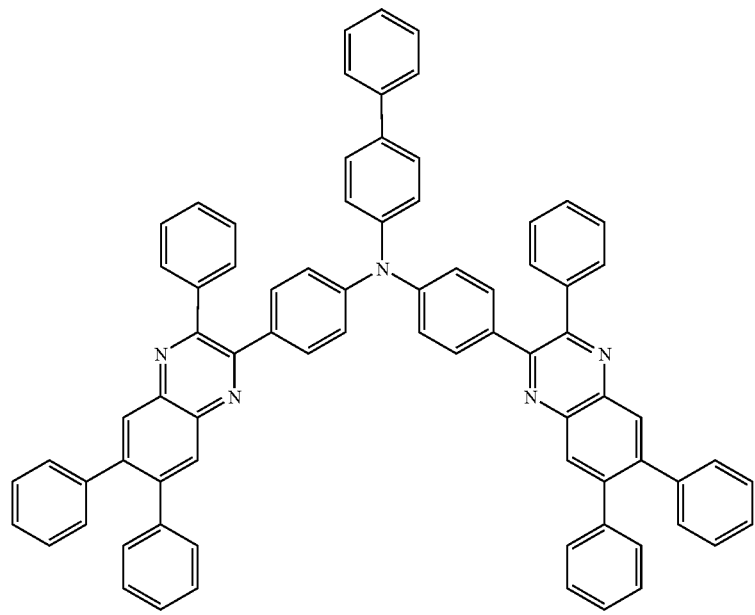
(120)
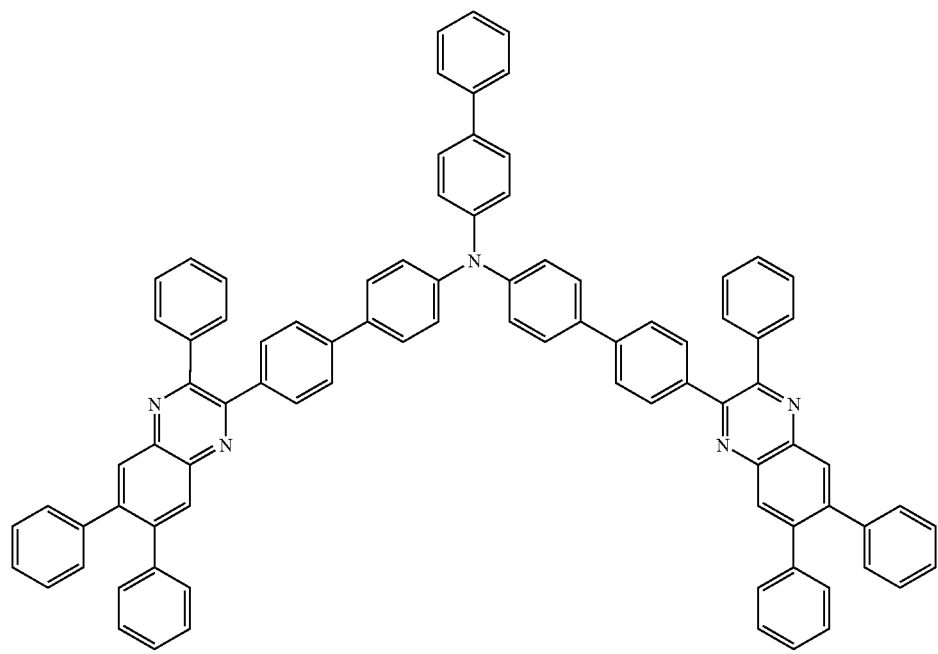
(121)
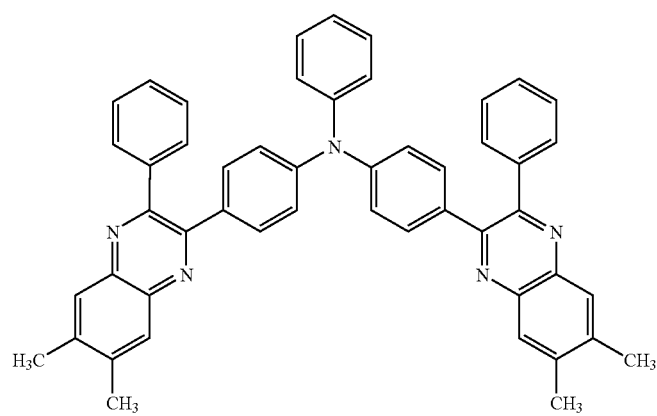

(122)
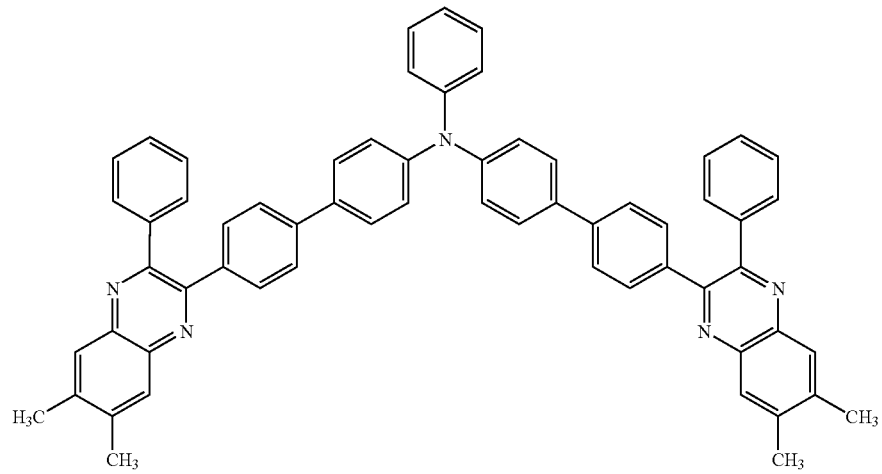
(123)
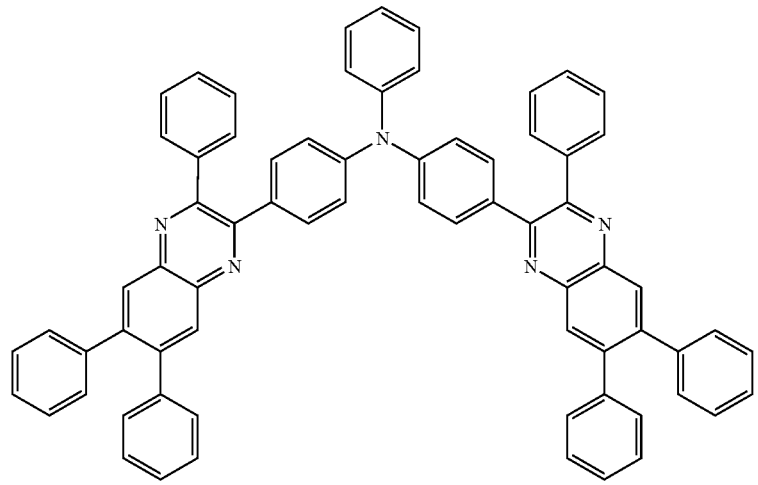
(124)
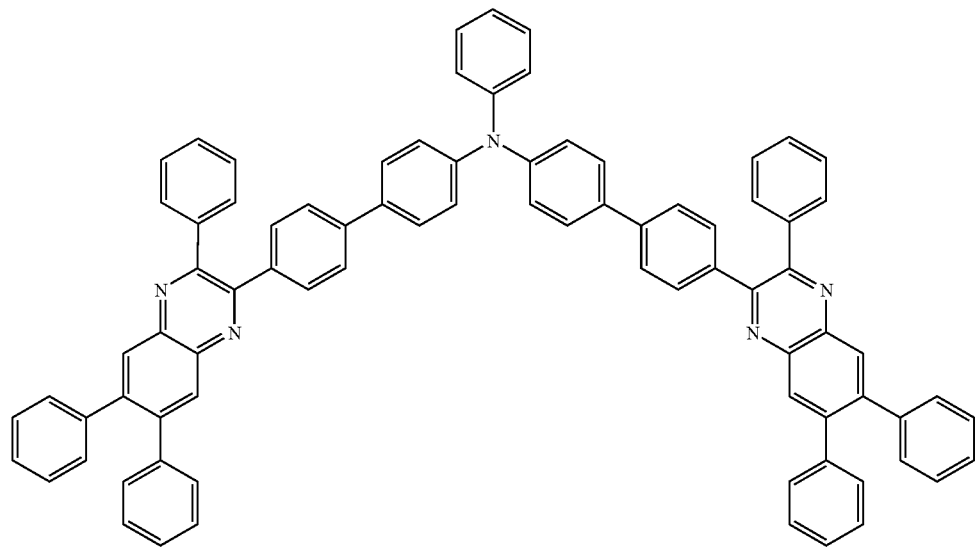

A synthesis method of the quinoxaline derivative of the present invention is described. The quinoxaline derivative of the present invention can be produced by synthesis reactions shown in (A-1) to (A-3) below.

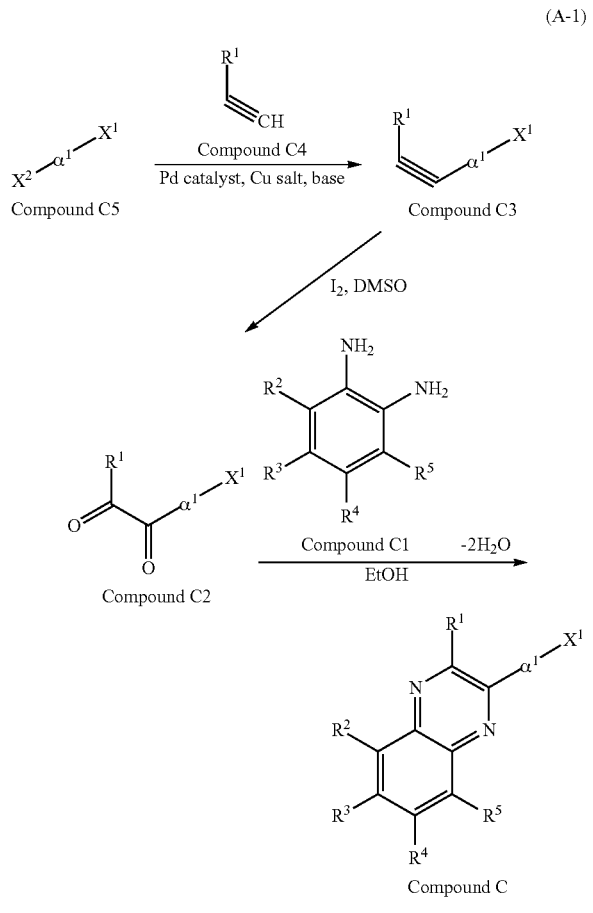

(A-1)

For the alkynyl aryl compound (compound C3) thus obtained, by making iodine act in dimethyl sulfoxide (DMSO) solvent, a halogenated aryl substituted diketone compound (compound C2) can be obtained.

Then, by a condensation reaction of the diketone compound (compound C2) and a compound (compound C1) containing 1-2-diaminobenzene as a skeleton, a halogenated aryl substituted quinoxaline compound (compound C) can be synthesized.

Next, by coupling of the halogenated aryl substituted quinoxaline derivative (compound C) obtained by the reaction scheme (A-1) with arylamine (compound A1) in the presence of a base, using a metal catalyst, a quinoxaline derivative (compound A) in which a quinoxaline skeleton and amine are bonded to each other via $\alpha^1$ can be obtained (reaction scheme (A-2)).

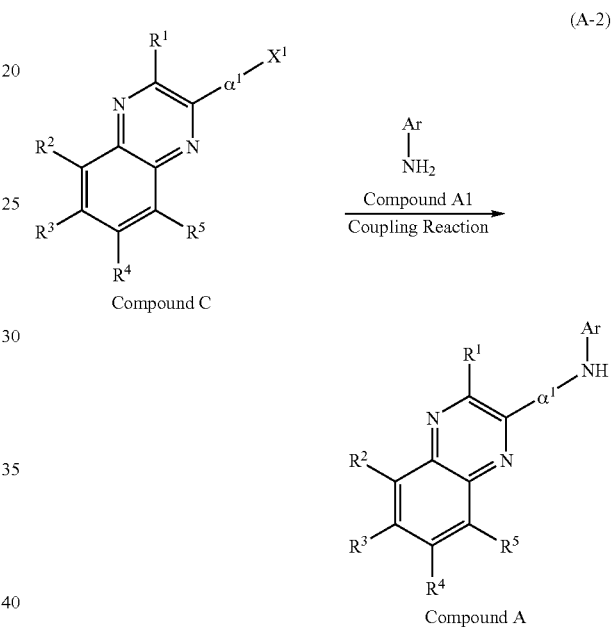

(A-2)

In the above scheme (A-1) of the synthesis method, $X^1$ and $X^2$ each independently represent a halogen, preferably, bromine or iodine from the viewpoint of the reaction rate. In this manner, substances corresponding to $X^1$ and $X^2$ are reacted at a higher rate. Further, in a reaction of a dihalogen compound C5 and an acetylenic compound C4, when a substance corresponding to $X^2$ of the above dihalogen compound C5 is preferentially reacted (e.g., when $\alpha^1$ is unsymmetrical with respect to $X^1$ and $X^2$), it is preferable that $X^1$ be bromine and that $X^2$ be iodine.

A reaction in which the dihalogen compound (compound C5) is reacted with a terminal alkyne compound (compound C4) to give an alkynyl aryl compound (compound C3) is described. This reaction is performed by a Sonogashira coupling, for example. In a Sonogashira coupling reaction, amine is used as a solvent, and copper salt and a palladium complex act together, whereby the reaction progresses. As the palladium catalyst, tetrakis triphenylphosphine palladium(0) or the like can be used. As the copper salt, copper iodide or the like can be used. As a solvent, diethylamine, triethylamine, or the like, which also serves as a base, can be used. Further, when the solubility of a substrate is low, tetrahydrofuran (THF), diethyl ether, or the like may be added as a cosolvent. Further, possibly, triarylphosphine may be used as a ligand of the palladium catalyst. However, the catalyst, the ligand thereof, the base, and the solvent which can be used are not limited to these examples.

In the above scheme (A-2) of the synthesis method, $X^1$ represents a halogen, preferably, bromine or iodine in particular from the viewpoint of the reaction rate. In this manner, a substance corresponding to $X^1$ is reacted at a higher rate.

When the above synthesis method (A-2) is performed by using a Hartwig-Buchwald reaction, a palladium catalyst can be used. As this palladium catalyst, bis(dibenzylideneacetone)palladium(0) or palladium(II) acetate can be used. Further, as a ligand of the above palladium catalyst, tri(tert-butyl)phosphine, tri(n-hexyl)phosphine, or tricyclohexylphosphine can be used. Furthermore, as a base, an organic base such as sodium-tert-butoxide (abbreviation: tert-BuONa) or an inorganic base such as potassium carbonate can be used. As the solvent, toluene, xylene, or benzene can be used. However, the catalyst, the ligand thereof, the base, and the solvent which can be used are not limited to these examples.

After that, by coupling of the quinoxaline derivative (compound A) in which a quinoxaline skeleton and amine are bonded to each other via $\alpha^1$, which is obtained by the reaction scheme (A-2), with a compound B (an halogenated aryl substituted quinoxaline compound) synthesized in a similar manner to the compound C in the presence of a base, using a metal catalyst, a compound M which is a quinoxaline derivative of the present invention can be obtained (reaction scheme (A-3)).

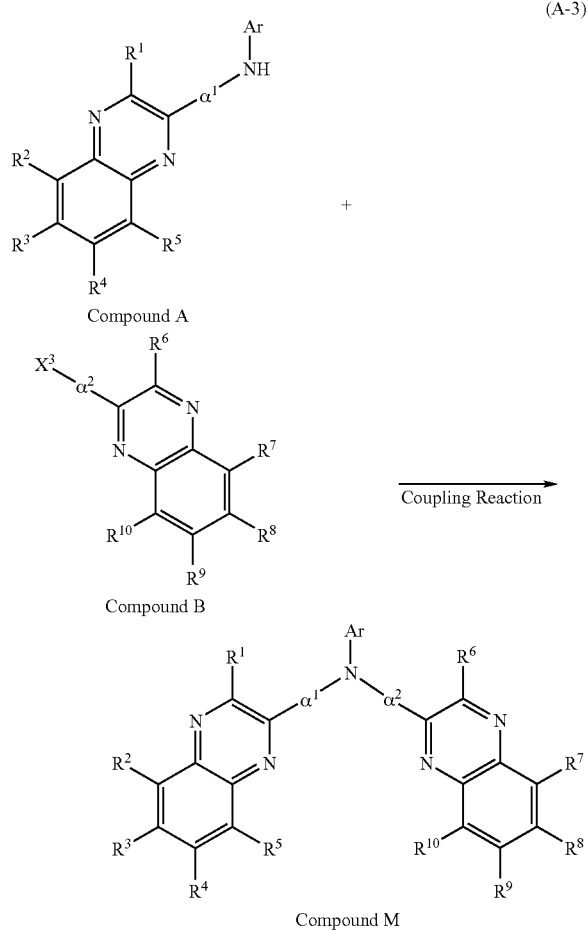

In the above scheme (A-3) of the synthesis method, $X^3$ represents a halogen, preferably, bromine or iodine in particular from the viewpoint of the reaction rate. In this manner, a substance corresponding to $X^3$ is reacted at a higher rate.

When the above synthesis method (A-3) is performed by using a Hartwig-Buchwald reaction, a palladium catalyst can be used. As this palladium catalyst, bis(dibenzylideneacetone)palladium(0) or palladium(II) acetate can be used. As a ligand of the above palladium catalyst, tri(tert-butyl)phosphine, tri(n-hexyl)phosphine, or tricyclohexylphosphine can be used. Further, as a base, an organic base such as sodium-tert-butoxide (abbreviation: tert-BuONa) or an inorganic base such as potassium carbonate can be used. As the solvent, toluene, xylene, or benzene can be used. However, the catalyst, the ligand thereof, the base, and the solvent which can be used are not limited to these examples.

The quinoxaline derivative of the present invention is bipolar and has both an excellent electron-transporting property and an excellent hole-transporting property. Therefore, by using the quinoxaline derivative of the present invention for an electronics device, lower driving voltage can be achieved. Further, since the quinoxaline derivative of the present invention is bipolar, by using the quinoxaline derivative of the present invention as a host material for a light-emitting layer, the carrier balance in the light-emitting layer is improved; accordingly, an emission center substance can be made to emit light efficiently in the light-emitting layer. Further, due to excellent carrier balance, light emission from a layer other than the light-emitting layer by carriers passing through the light-emitting layer or by localization of a light-emitting region can be suppressed, and accordingly a light-emitting element which emits light having high color purity can be manufactured.

Embodiment Mode 2

Hereinafter, a mode of a light-emitting element using the quinoxaline derivative of the present invention is described using FIG. 1A.

A light-emitting element of the present invention has a plurality of layers between a pair of electrodes. In this embodiment mode, the light-emitting element includes a first electrode 102, a second electrode 104, and an EL layer 103 provided between the first electrode 102 and the second electrode 104. Note that in this embodiment mode, the first electrode 102 serves as an anode and that the second electrode 104 serves as a cathode. In other words, hereinafter, it is assumed that when a voltage is applied to the first electrode 102 and the second electrode 104 so that the potential of the first electrode 102 is higher than that of the second electrode 104, light emission can be obtained.

A substrate 101 is used as a support of the light-emitting element. For example, glass, plastic, or the like can be used for the substrate 101. Any material other than these materials may be used as long as it functions as the support of the light-emitting element.

As the first electrode 102, a metal, an alloy, an electroconductive compound, a mixture thereof, or the like having a high work function (specifically, 4.0 eV or more) is preferably used. Specifically, for example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like are given. Films of such conductive metal oxides are typically formed by sputtering, but may also be formed by applying a sol-gel method or the like. For example, a layer of indium oxide-zinc oxide (IZO) can be formed by a sputtering method using a target in which 1 wt % to 20 wt % of zinc oxide is added to indium oxide. Further, indium oxide containing tungsten oxide and zinc oxide (IWZO) can be formed by a sputtering method using a target in which 0.5 wt % to 5 wt % of tungsten oxide and 0.1 wt % to 1 wt % of zinc oxide are added to indium oxide. Alternatively, there are gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), and the like.

There is no particular limitation on a stack structure of the EL layer 103. It is acceptable as long as the EL layer 103 is formed by any combination of a layer containing the quinoxaline derivative of the present invention, which is described in Embodiment Mode 1, with a layer which contains a substance such as a substance having a high electron-transporting property, a substance having a high hole-transporting property, a substance having a high electron-injecting property, a substance having a high hole-injecting property, a bipolar substance (a substance having a high electron-transporting property and a high hole-transporting property), or the like. For example, the EL layer 103 can be formed of, as appropriate, by any combination of a hole-injecting layer, a hole-transporting layer, a light-emitting layer, an electron-transporting layer, an electron-injecting layer, etc. In this embodiment mode, the EL layer 103 has a structure in which a hole-injecting layer 111, a hole-transporting layer 112, a light-emitting layer 113, and an electron-transporting layer 114 are stacked in that order over the first electrode 102. Materials for forming the layers are specifically given below.

The hole-injecting layer 111 is a layer containing a substance with a high hole-injecting property. Molybdenum oxide, vanadium oxide, ruthenium oxide, tungsten oxide, manganese oxide, or the like can be used. Alternatively, the hole-injecting layer 111 can be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or 4,4'-bis(N-{4-[N-(3-methylphenyl)-N-phenylamino]phenyl}-N-phenylamino)biphenyl (abbreviation: DNTPD); a high molecule such as poly(3,4-ethylenedioxythiophene)/poly(styrenesulfonic acid) (PEDOT/PSS), or the like.

Alternatively, the hole-injecting layer 111 can be formed using a composite material in which an acceptor substance is mixed into a substance having a high hole-transporting property. Note that by using the material having a high hole-transporting property which contains an acceptor material, a material for forming an electrode may be selected regardless of its work function. That is, instead of a material having a high work function, a material having a low work function can be used for the first electrode 102. As the acceptor material, 7,7,8,8-tetracyano-2,3,5,6-tetrafluoroquinodimethane (abbreviation: $F_4$-TCNQ), chloranil, and the like can be given. Further, transition metal oxides can be given. Further, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of having a high electron accepting property. Among these, molybdenum oxide is especially preferable because of its stability in the atmosphere, a low hygroscopic property, and easiness of handling.

As a substance having a high transporting property, which is used for the composite material, any of a variety of compounds such as aromatic amine compounds, carbazole derivatives, aromatic hydrocarbons, and high molecular compounds (such as oligomers, dendrimers, or polymers) can be used. The organic compound used for the composite material is preferably an organic compound having a high hole-transporting property. Specifically, a substance having a hole mobility of $10^{-6}$ cm$^2$/Vs or more is preferably used. Note that any substance other than the above substances may also be used as long as it is a substance in which the hole-transporting property is higher than the electron-transporting property. Hereinafter, organic compounds that can be used for the composite material are specifically given.

As aromatic amine compounds, for example, there are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), and the like.

As carbazole derivatives which can be used for the composite material, specifically, there are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

As other examples of carbazole derivatives which can be used for the composite material, there are 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), 1,4-bis[4-(N-carbazolyl)phenyl]-2,3,5,6-tetraphenylbenzene, and the like.

Further, as aromatic hydrocarbons which can be used for the composite material, for example, there are 2-tert-butyl-9,10-di(2-naphthyl)anthracene (abbreviation: t-BuDNA); 2-tert-butyl-9,10-di(1-naphthyl)anthracene, 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Alternatively, pentacene, coronene, or the like can also be used. As described above, an aromatic hydrocarbon having a hole mobility of $1\times10^{-6}$ cm$^2$/Vs or more and 14 to 42 carbon atoms is preferably used.

Note that an aromatic hydrocarbon which can be used for the composite material may have a vinyl skeleton. As an aromatic hydrocarbon having a vinyl group, for example, there are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Alternatively, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl -N'-phenylamino}phenyl) methacrylamide] (abbreviation: PTPDMA), or poly[N,N'-bis(4-butylphenyl)-N,N'-bis(phenyl)benzidine (abbreviation: poly-TPD) can be used.

The hole-transporting layer 112 is a layer containing a material having a high hole-transporting property. As a substance having a high hole-transporting property, an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), or 4,4'-bis[N-(spiro-9,9'-bifluoren-2-yl)-N-phenylamino]biphenyl (abbreviation: BSPB) or the like can be used. The substances mentioned here mainly are substances having a hole mobility of $10^{-6}$ cm$^2$/Vs or more. Note that any substance other than the above substances may be used as long as it is a substance in which the hole-transporting property is higher than the electron-transporting property. Further, the layer containing a substance having a high hole-transporting property may be a stack of two or more layers made of the above substances, instead of a single layer.

Alternatively, for the hole-transporting layer 112, a high molecular compound such as poly(N-vinylcarbazole) (abbreviation: PVK) or poly(4-vinyltriphenylamine) (abbreviation: PVTPA) can also be used.

The light-emitting layer 113 is a layer containing a light-emitting substance. In this embodiment mode, the light-emitting layer 113 contains the quinoxaline derivative of the present invention, which is described in Embodiment Mode 1. The quinoxaline derivative of the present invention exhibits emission of blue to green light, and thus can be preferably used as a light-emitting substance for a light-emitting element.

The electron-transporting layer 114 is a layer containing a high electron-transporting property. For example, the electron-transporting layer 114 is a layer containing a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq3), bis(10-hydroxybenzo[h]-quinolinato)beryllium (abbreviation: BeBq$_2$), or bis(2-methyl-8-quinolinolato)(4-phenylphenolato)aluminum (abbreviation: BAlq), or the like. Alternatively, a metal complex having an oxazole-based or thiazole-based ligand, such as bis[2-(2-hydroxyphenyl)benzoxazolato]zinc (abbreviation: Zn(BOX)$_2$), or bis[2-(2-hydroxyphenyl)-benzothiazolato]zinc (abbreviation: Zn(BTZ)$_2$), or the like can be used. Furthermore, instead of metal complexes, 2-(4-biphenylyl)-5-(4-tert-butylphenyl)-1, 3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here mainly are substances having an electron mobility of 10$^{-6}$ cm$^2$/Vs or more. Note that any substance other than the above substances may be used as long as it is a substance in which the electron-transporting property is higher than the hole-transporting property. Further, the electron-transporting layer may be a stack of two or more layers made of the above substances, instead of a single layer.

Further, an electron-injecting layer may be provided. For the electron-injecting layer, an alkali metal, an alkaline earth metal, or a compound thereof, such as lithium fluoride (LiF), cesium fluoride (CsF), or calcium fluoride (CaF$_2$), can be used. A layer in which an alkali metal, an alkaline earth metal, or a compound thereof is contained in a substance having an electron-transporting property, for example, a layer in which magnesium (Mg) is contained in Alq, or the like can be used. Note that by using a layer in which an alkali metal, an alkaline earth metal, or a compound thereof is contained in a substance having an electron-transporting property, electrons can be injected efficiently from the second electrode 104, which is preferable.

As a substance for forming the second electrode 104, a metal, an alloy, an electroconductive compound, a mixture thereof, or the like having a low work function (specifically, 3.8 eV or less) can be used. As specific examples of such cathode materials, there are elements that belong to Group 1 and Group 2 of the periodic table, that is, alkali metals such a lithium (Li) and cesium (Cs) and alkaline earth metals such as magnesium (Mg), calcium (Ca), and strontium (Sr); alloys thereof (e.g., MgAg, or AlLi); rare earth metals such as europium (Eu) and ytterbium (Yb); alloys thereof; and the like. However, by providing the electron-injecting layer between the second electrode 104 and the electron-transporting layer 114, the second electrode 104 can be formed using any of a variety of conductive materials such as Al, Ag, ITO, indium oxide-tin oxide containing silicon or silicon oxide, or the like regardless of its work function. These conductive materials can be deposited by a sputtering method, an inkjet method, a spin coating method, or the like.

Further, any of a variety of methods can be used for forming the EL layer 103, regardless of a dry method or a wet method. For example, a vacuum evaporation method, an inkjet method, a spin coating method, or the like may be used. Further, the electrodes and the layers may be formed by different deposition methods.

Similarly, the electrodes may be formed by a wet process such as a sol-gel method or by a wet process using a metal paste. Further, a dry method such as a sputtering method or a vacuum evaporation method may be used.

In the light-emitting element of the present invention, which has the structure as described above, the potential difference between the first electrode 102 and the second electrode 104 makes a current flow, whereby a hole and an electron recombine with each other in the light-emitting layer 113 which is a layer containing a high light-emitting property and thus light is emitted. That is, the light-emitting element of the present invention has a structure in which a light-emitting region is formed in the light-emitting layer 113.

Figure 1B:
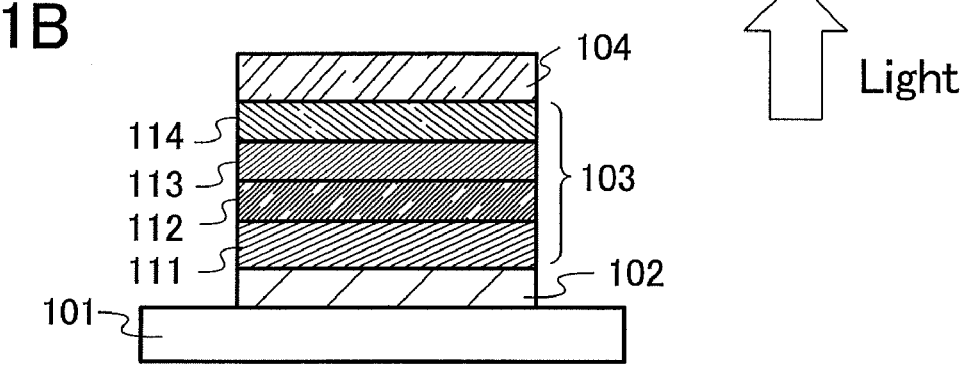
Figure 1C:
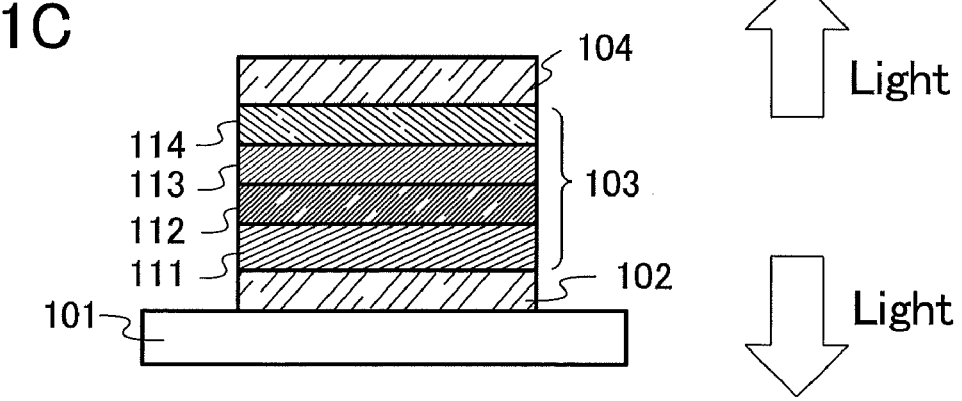

Emitted light is extracted out through one or both of the first electrode 102 and the second electrode 104. Therefore, one or both of the first electrode 102 and the second electrode 104 is/are formed of an electrode having a light transmitting property. When only the first electrode 102 has a light transmitting property, emitted light is extracted from a substrate 101 side through the first electrode 102, as illustrated in FIG. 1A. Alternatively, when only the second electrode 104 is has a light transmitting property, emitted light is extracted from the side opposite to the substrate 101 side through the second electrode 104, as illustrated in FIG. 1B. When the first electrode 102 and the second electrode 104 each have a light-transmitting property, emitted light is extracted from both the substrate 101 side and the side opposite to the substrate 101 side through the first electrode 102 and the second electrode 104, as illustrated in FIG. 1C.

Note that the structure of the layers provided between the first electrode 102 and the second electrode 104 is not limited to the above example. Any other structure may be employed as long as a light-emitting region for recombination of holes and electrons is positioned away from the first electrode 102 and the second electrode 104 so as to prevent quenching due to the proximity of the light-emitting region and a metal.

That is, there is no particular limitation on a stack structure of the layers. The quinoxaline derivative of the present invention may be freely combined with a layer which contains a substance having a high electron-transporting property, a substance having a high hole-transporting property, a substance having a high electron-injecting property, a substance having a high hole-injecting property, a bipolar substance (a substance having a high electron-transporting property and a high hole-transporting property), or the like.

Figure 2:
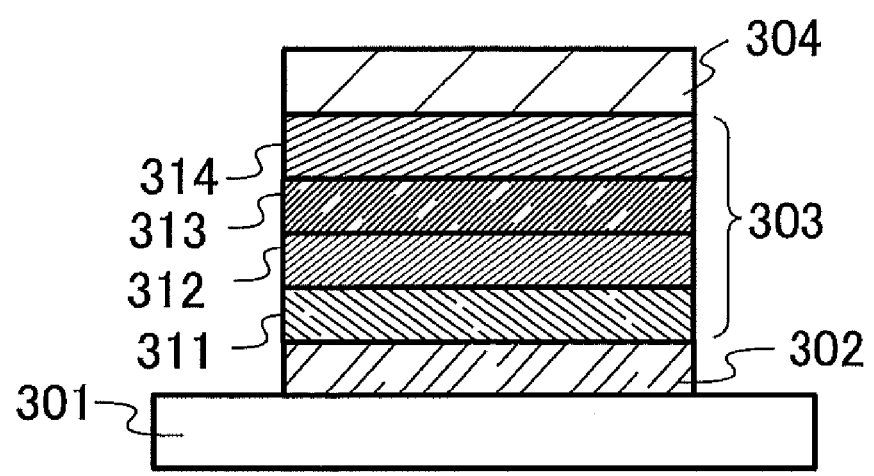
FIG. 2 illustrates a light-emitting element according to an aspect of the present invention.

A light-emitting element illustrated in FIG. 2 has a structure in which a first electrode 302 functioning as a cathode, an electron-transporting layer 311, a light-emitting layer 312, a hole-transporting layer 313, a hole-injecting layer 314, and a second electrode 304 functioning as an anode are stacked in that order over a substrate 301.

In this embodiment mode, the light-emitting element is manufactured over a substrate made of glass, plastic, or the like. By forming a plurality of such light-emitting elements over one substrate, a passive matrix light-emitting device can be manufactured. Alternatively, for example, thin film transistors (TFTs) may be formed over a substrate made of glass, plastic, or the like, and light-emitting elements may be formed over an electrode electrically connected to the TFTs. Thus, an active matrix light-emitting device that controls driving of a light-emitting element by a TFT can be manufactured. Note that there is no particular limitation on the structure of the TFT. Either a staggered TFT or an inverted staggered TFT may be employed. Further, there is no particular limitation on the crystallinity of a semiconductor used for the TFT, and an amorphous semiconductor may be used, or a crystalline semiconductor may be used. Further, a driving circuit formed over a TFT substrate may be formed using an n-type TFT and a p-type TFT, or may be formed using any of an n-type TFT or a p-type TFT.

The quinoxaline derivative of the present invention is a bipolar and light-emitting material, and therefore can be used as a light-emitting layer without containing any other light-emitting substance, as described in this embodiment mode.

Further, since the quinoxaline derivative of the present invention is bipolar, a light-emitting element in which a light-emitting region is rarely located at an interface of stacked films, and which shows favorable characteristics with few changes in light emission spectrum and a small decrease in light emission efficiency due to an interaction such as exciplex can be manufactured. Furthermore, a light-emitting element with high emission efficiency can be obtained.

Further, since microcrystalline components are hardly contained during deposition, an amorphous film which contains few microcrystalline components can be obtained. That is, the film has a favorable quality; therefore, a light-emitting element with few element defects such as a dielectric breakdown due to electric field concentration can be formed.

Further, the quinoxaline derivative of the present invention is bipolar and has an excellent carrier-transporting property (an electron-transporting property and a hole-transporting property); therefore, by using the quinoxaline derivative of the present invention for a light-emitting element, driving voltage of the light-emitting element can be reduced, resulting in a reduction in power consumption.

Embodiment Mode 3

In this embodiment mode, a light-emitting element having a structure different from the structure described in Embodiment Mode 2 is described.

The light-emitting layer 113 described in Embodiment Mode 2 contains the quinoxaline derivative of the present invention, which is dispersed in another substance; accordingly, light emission can be obtained from this quinoxaline derivative of the present invention. Since the quinoxaline derivative of the present invention exhibits emission of blue to green light, a blue to green light-emitting element can be obtained.

Here, as the substance in which the quinoxaline derivative of the present invention is dispersed, instead of the substance having a high hole-transporting property or the substance having a high electron-transporting property, which is described in Embodiment Mode 2, any of a variety of materials such as 4,4'-di(N-carbazolyl)biphenyl (abbreviation: CBP); 2,2',2"-(1,3,5-benzenetriyl)tris(1-phenyl-1H-benzimidazole) (abbreviation: TPBI); 9,10-di(2-naphthyl)anthracene (abbreviation: DNA); or 2-tert-butyl-9,10-di(2-naphthyl)anthracene (abbreviation: t-BuDNA) can be used.

Further, the quinoxaline derivative of the present invention is bipolar and has an excellent carrier-transporting property (an electron-transporting property and a hole-transporting property); therefore, by using the quinoxaline derivative of the present invention for a light-emitting element, driving voltage of the light-emitting element can be reduced, resulting in a reduction in power consumption.

Further, the quinoxaline derivative of the present invention is stable even when oxidation-reduction and reduction-oxidation reactions are repeated. That is, the quinoxaline derivative of the present invention is electrochemically stable. Therefore, by using the quinoxaline derivative of the present invention for a light-emitting element, a light-emitting element having long life can be obtained.

Note that for the layers other than the light-emitting layer 113, the structures described in Embodiment Mode 2 can be used as appropriate.

Embodiment Mode 4

In this embodiment mode, a light-emitting element having a structure different from the structures described in Embodiment Mode 2 and Embodiment Mode 3 is described.

The light-emitting layer 113 described in Embodiment Mode 2 has a structure in which a light-emitting substance is dispersed in the quinoxaline derivative of the present invention, and accordingly light emission can be obtained from the light-emitting substance.

The quinoxaline derivative of the present invention is bipolar. Further, microcrystalline components are hardly contained during deposition of the quinoxaline derivative of the present invention, and thus the film with a high quality can be obtained. Therefore, the quinoxaline derivative of the present invention is preferably used as a material in which another light-emitting substance is dispersed.

When the quinoxaline derivative of the present invention is used as the material in which another light-emitting substance is dispersed, an emission color resulting from the light-emitting substance can be obtained. Further, it is also possible to obtain an emission color which is a mixture of the emission color resulting from the quinoxaline derivative of the present invention and the emission color resulting from the light-emitting substance dispersed in the quinoxaline derivative.

Here, for the light-emitting substance dispersed in the quinoxaline derivative of the present invention, any of a variety of materials can be used. Specifically, a fluorescent compound that emits fluorescence, such as 4-(dicyanomethylene)-2-methyl-6-(p-dimethylaminostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridone (DMQd), 9,10-diphenylanthracene (abbreviation: DPA), 5,12-diphenyltetracene (abbreviation: DPT), coumarin 6, perylene, or rubrene can be used. Alternatively, a phosphorescent substance that emits phosphorescence, such as bis(2-phenylbenzothiazolato-N,$C^{2'}$)iridium (III)acetylacetonate (abbreviation: Ir(bt)$_2$(acac)), tris(2-phenylquinolinato-N,$C^{2'}$)iridium(III) (abbreviation: Ir(pq)3), bis(2-phenylquinolinato-N,$C^{2'}$)iridium(III)acetylacetonate (abbreviation: Ir(pq)$_2$(acac)), bis[2-(2'-benzo[4,5-α]thienyl)pyridinato-N,$C^{3'}$]iridium(III)acetylacetonate (abbreviation: Ir(btp)$_2$(acac)), bis(1-phenylisoquinolinato-N,$C^{2'}$)iridium (III)acetylacetonate (abbreviation: Ir(piq)$_2$(acac)), (acetylacetonato)bis[2,3-bis(4-fluorophenyl)quinoxalinato]iridium (III) (abbreviation: Ir(Fdpq)$_2$(acac)), and (2,3,7,8,12,13,17,18-octaethyl-21H,23H-porphyrinato)platinum(II) (abbreviation: PtOEP) can be used. In the case of using a phosphorescent substance as the light-emitting substance which is to be dispersed, it is preferable that an emission spectrum of the phosphorescent substance have a peak at greater than or equal to 560 nm and less than or equal to 700 nm. In the case of using the fluorescent substance, the peak of an emission spectrum of the fluorescent substance is preferably greater than or equal to 500 nm and less than or equal to 700 nm, and further preferably, greater than or equal to 500 nm and less than or equal to 600 nm.

The quinoxaline derivative of the present invention is bipolar and has an excellent carrier transporting property (an electron-transporting property and a hole-transporting property); therefore, by using the quinoxaline derivative of the present invention, driving voltage of the light-emitting element can be reduced.

Further, since the quinoxaline derivative of the present invention is bipolar, the light-emitting region is not readily localized at an interface of the stacked films. Hence, it is possible to provide a high-performance light-emitting element that exhibits few changes in the emission spectrum and a small decrease in emission efficiency, resulting from an interaction such as exciplex formation.

Further, since the quinoxaline derivative of the present invention is bipolar, a light-emitting region is not readily localized at an interface of the stacked films. Therefore, when the quinoxaline derivative of the present invention is used as a host and a phosphorescent substance that emits phosphorescence is used as a light-emitting substance, T-T annihilation can be prevented. Accordingly, a light-emitting element with high emission efficiency can be obtained.

Note that for the layers other than the light-emitting layer 113, the structures described in Embodiment Mode 2 can be used as appropriate.

Embodiment Mode 5

In this embodiment mode, a mode of a light-emitting element in which a plurality of light-emitting units according to the present invention is stacked (hereinafter, referred to as a stacked-type element) is described with reference to FIG. 3. This light-emitting element has a plurality of light-emitting units between a first electrode and a second electrode. For the light-emitting units, a structure similar to that of the EL layer 103 described in Embodiment Mode 2 can be used. That is, the light-emitting elements described in Embodiment Modes 2 to 4 are each a light-emitting element having a single light-emitting unit. In this embodiment mode, a light-emitting element having a plurality of light-emitting units is described.

Figure 3:
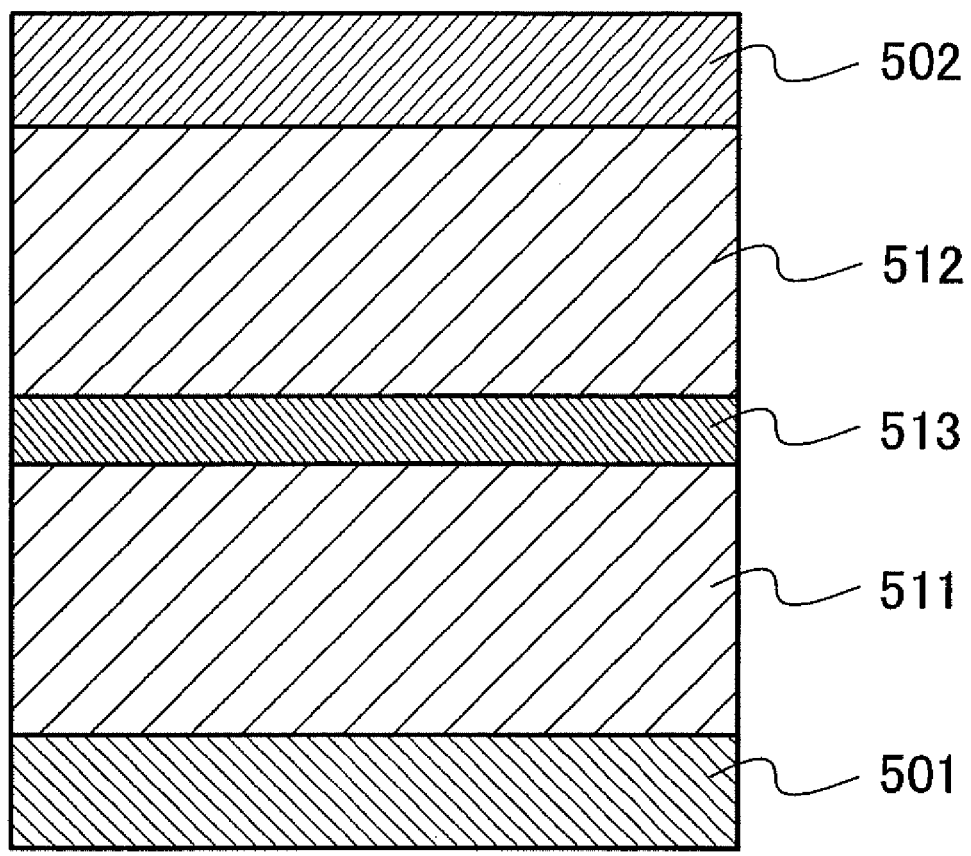
FIG. 3 illustrates a light-emitting element according to an aspect of the present invention.

In FIG. 3, a first light-emitting unit 511 and a second light-emitting unit 512 are stacked between a first electrode 501 and a second electrode 502, and a charge generation layer 513 is provided between the first light-emitting unit 511 and the second light-emitting unit 512. Materials similar to those in Embodiment Mode 2 can be applied to the first electrode 501 and the second electrode 502. Further, the first light-emitting unit 511 and the second light-emitting unit 512 may have the same structure or different structures, and a structure similar to those described in Embodiment Modes 2 to 4 can be applied.

In the charge generation layer 513, a composite material of an organic compound and a metal oxide is contained. This composite material of an organic compound and a metal oxide has been described in Embodiment Mode 2 and contains an organic compound and a metal oxide such as vanadium oxide, molybdenum oxide, or tungsten oxide. As the organic compound, any of a variety of compounds such as aromatic amine compounds, carbazole derivatives, aromatic hydrocarbons, and high molecular compounds (oligomers, dendrimers, polymers, and the like) can be used. Note that as the organic compound, it is preferable to use an organic compound having a hole mobility of $10^{-6}$ cm$^2$/Vs or more, which serves as a hole-transporting organic compound. Further, any substance other than the above substances may also be used as long as it is a substance in which the hole-transporting property is higher than the electron-transporting property. Since the composite of an organic compound and a metal oxide has an excellent carrier injecting property and an excellent carrier transporting property, low-voltage driving and low-current driving can be realized.

Note that the charge generation layer 513 may be formed by combining a layer containing the composite material of the organic compound and the metal oxide with a layer formed of another material. For example, the charge generation layer 513 may be formed by combining a layer containing the composite material of the organic compound and the metal oxide with a layer which contains one compound selected from electron donating substances and a compound having a high electron-transporting property. Alternatively, the charge generation layer 513 may be formed by combining a layer containing the composite material of the organic compound and the metal oxide with a transparent conductive film.

The charge generation layer 513 interposed between the first light-emitting unit 511 and the second light-emitting unit 512 may have any structure as long as electrons can be injected into one of the light-emitting units and holes can be injected into the other light-emitting unit when a voltage is applied between the first electrode 501 and the second electrode 502. For example, in FIG. 3, the structure may be employed in which, when a voltage is applied so that the potential of the first electrode is higher than that of the second electrode, the charge generation layer 513 injects electrons into the first light-emitting unit 511 and injects holes into the second light-emitting unit 512.

Although the light-emitting element having two light-emitting units is described in this embodiment mode, a light-emitting element in which three or more light-emitting units are stacked can be employed in a similar way. With the plurality of light-emitting units partitioned by the charge generation layer between the pair of electrodes, as in the case of the light-emitting element of this embodiment mode, light emission with a high luminance can be obtained -while a low current density is maintained; thus, an element having long life can be realized. Further, when the light-emitting element is applied to a lighting apparatus as an application example, voltage drop due to resistance of an electrode material can be reduced. Accordingly, uniform light emission in a large area can be realized. Moreover, a light-emitting device which can drive at a low voltage and consumes low power can be achieved.

Further, by differeing emission colors of the light-emitting units, light emission of a desired color can be obtained from the whole light-emitting element. For example, in a light-emitting element having two light-emitting units, emission colors of the first light-emitting unit and the second light-emitting unit are made to be complementary, whereby a light-emitting element which emits white light from the whole light-emitting element can be obtained. Note that "complementary color" means a relation between colors which becomes an achromatic color when they are mixed. That is, by mixing light from substances whose emission colors are complementary colors, white light emission can be obtained. This is applied to a light-emitting element having three light-emitting units in a similar manner. For example, when an emission color of the first light-emitting element is red, an emission color of the second light-emitting element is green, and an emission color of the third light-emitting element is blue, white light can be obtained from the whole light-emitting element.

Note that this embodiment mode can be combined with any other embodiment mode as appropriate.

Embodiment Mode 6

In this embodiment mode, a mode in which the quinoxaline derivative of the present invention is used for an active layer of a vertical transistor (SIT) that is one kind of an organic semiconductor element is given as an example.

Figure 4:
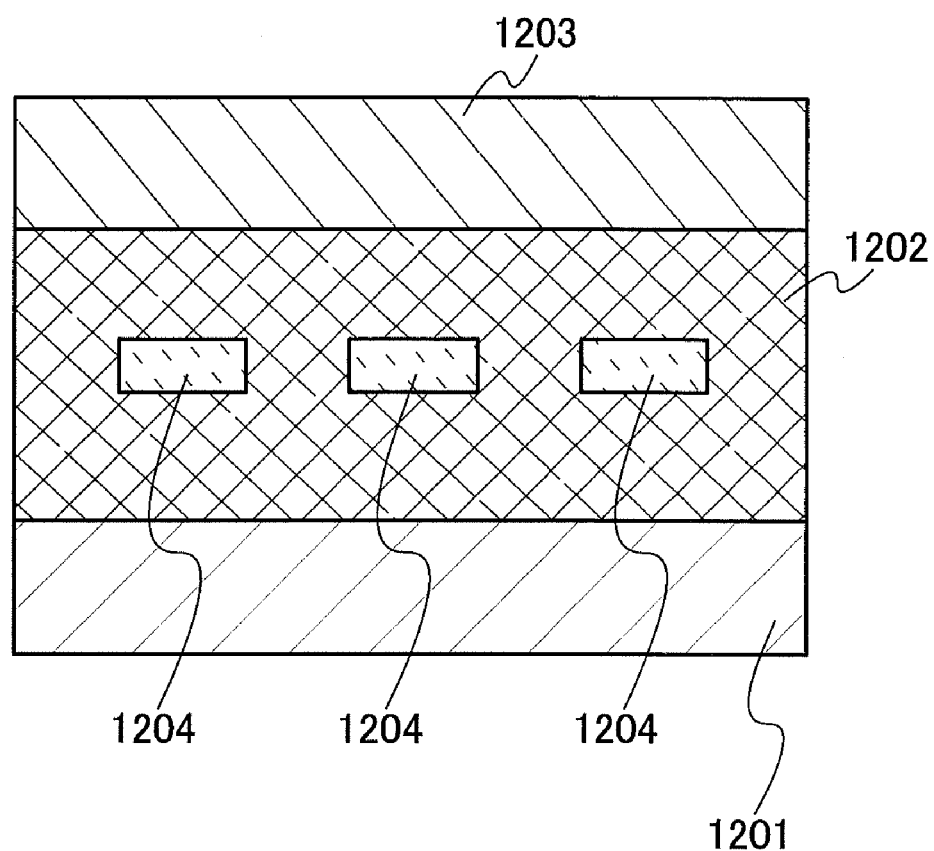
FIG. 4 illustrates an organic semiconductor element according to an aspect of the present invention.

As illustrated in FIG. 4, the element has a structure in which a thin film shaped active layer 1202 containing the quinoxaline derivative of the present invention is interposed between a source electrode 1201 and a drain electrode 1203, and gate electrodes 1204 are embedded in the active layer 1202. The gate electrodes 1204 are electrically connected to a means for applying a gate voltage, and the source electrode 1201 and the drain electrode 1203 are electrically connected to a means for controlling a source-drain voltage.

In such an element structure, when a source-drain voltage is applied under the condition where a gate voltage is not applied, a current flows (the element is placed in an on state). Then, when a gate voltage is applied in this state, a depletion layer is generated on the periphery of the gate electrode 1204, thereby stopping the current flow (the element is placed in an off state). With the above mechanism, the element operates as a transistor.

In a vertical transistor, in a similar manner to a light-emitting element, a material which has both a carrier transporting property and an excellent film quality is required for an active layer. The quinoxaline derivative of the present invention sufficiently meets the requirement and therefore is useful.

Embodiment Mode 7

In this embodiment mode, a light-emitting device manufactured using the quinoxaline derivative of the present invention is described.

In this embodiment mode, a light-emitting device manufactured using the quinoxaline derivative of the present invention is described with reference to FIGS. 5A and 5B. Note that FIG. 5A is a top view illustrating a light-emitting device and FIG. 5B is a cross-sectional view taken along a line A-A' and a line B-B' in FIG. 5A. This light-emitting device includes a driver circuit portion (a source signal line driver circuit) 601, a pixel portion 602, and a driver circuit portion (a gate signal line driver circuit) 603 as units for controlling light emission from the light-emitting element. Further, reference numeral 604 indicates a sealing substrate, and reference numeral 605 indicates a sealing material. There is a space 607 inside a portion surrounded by the sealing material 605.

Note that a leading wiring 608 is a wiring for transmitting signals input to the source signal line driver circuit 601 and to the gate signal line driver circuit 603, and receives a video signal, a clock signal, a start signal, a reset signal, and the like from a flexible printed circuit (FPC) 609 which serves as an external input terminal. Note that although only the FPC is illustrated here, this FPC may be provided with a printed wiring board (PWB). The light-emitting device in this specification includes not only a light-emitting device itself but also the light-emitting device provided with an FPC or a PWB.

Next, a cross-sectional structure is described using FIG. 5B. The driver circuit portions and the pixel portion are provided over an element substrate 610. Here, only the source signal line driver circuit 601, which is the driver circuit portion, and one pixel of the pixel portion 602 are illustrated.

Note that as the source signal line driver circuit 601, a CMOS circuit in which an n-channel TFT 623 and a p-channel TFT 624 are combined with each other is formed. Further, the driver circuit may be formed of various circuits such as a CMOS circuit, a PMOS circuit, and an NMOS circuit. Further, although a driver integration type in which the driver circuit is formed over a substrate is described in this embodiment mode, such a type is not necessarily employed and the driver circuit can be formed outside the substrate, not over the substrate.

Further, the pixel portion 602 is formed of a plurality of pixels each having a switching TFT 611, a current controlling TFT 612, and a first electrode 613 which is electrically connected to a drain of the current controlling TFT. Note that an insulator 614 is formed to cover an end portion of the first electrode 613. Here, a positive photosensitive acrylic resin film is used to form the insulator 614.

Further, in order to improve the coverage, the insulator 614 is provided such that either an upper end portion or a lower end portion of the insulator 614 has a curved surface with curvature. For example, when positive photosensitive acrylic is used as a material for the insulator 614, only the upper end portion of the insulator 614 is preferably made to have a curved surface with a radius of curvature of 0.2 µm to 3 µm. Further, for the insulator 614, either negative photosensitive acrylic that becomes insoluble in an etchant due to light irradiation, or positive photosensitive acrylic that becomes dissoluble in an etchant due to light irradiation can be used.

Over the first electrode 613, an EL layer 616 and a second electrode 617 are formed. Here, as a material used for the first electrode 613 functioning as an anode, a material having a high work function is preferably used. For example, a single film such as an ITO film, an indium tin oxide film containing silicon, an indium oxide film containing 2 wt % to 20 wt % zinc oxide, a titanium nitride film, a chromium film, a tungsten film, a Zn film, and a Pt film; a stack of a titanium nitride film and a film containing aluminum as the main component; a three-layer structure of a titanium nitride film, a film containing aluminum as the main component, and a titanium nitride film; and the like can be employed. Note that when a stack structure is employed, the resistance as a wiring is low, a good ohmic contact can be obtained, and further the first electrode 613 can be made to function as an anode.

Further, the EL layer 616 is formed by any of a variety of methods such as an evaporation method using an evaporation mask, an inkjet method, a spin coating method, or the like. The EL layer 616 contains the quinoxaline derivative of the present invention, which is described in Embodiment Mode 1. Further, as another material contained in the EL layer 616, a low molecular compound or a high molecular compound (including an oligomer or a dendrimer in its category) may be used.

Furthermode, as a material used for the second electrode 617 formed over the EL layer 616, which serves as a cathode, a material having a low work function (Al, Mg, Li, Ca, or an alloy or a compound thereof such as MgAg, MgIn, AlLi, LiF, or $CaF_2$) is preferably used. Note that when light generated in the EL layer 616 is transmitted through the second electrode 617, for the second electrode 617, a stack of a metal thin film with a reduced thickness and a transparent conductive film (e.g., ITO, indium oxide containing 2 wt % to 20 wt % zinc oxide, indium tin oxide containing silicon, or zinc oxide (ZnO)) may be used.

Furthermore, by attaching the sealing substrate 604 to the element substrate 610 using the sealing material 605, the light-emitting element 618 is provided in the space 607 surrounded by the element substrate 610, the sealing substrate 604, and the sealing material 605. Note that the space 607 is filled with a filler and there are cases where the space 607 may be filled with an inert gas (nitrogen, argon, or the like) or where the space 607 may be filled with the sealing material 605.

Note that as the sealing material 605, an epoxy resin is preferably used. Further, such a material is desirably a material which does not transmit moisture or oxygen as much as possible. Further, as the sealing substrate 604, a glass substrate, a quartz substrate, or a plastic substrate made of fiberglass-reinforced plastics (FRP), polyvinyl fluoride (PVF), polyester, or acrylic, or the like can be used.

As described above, a light-emitting device manufactured using the quinoxaline derivative of the present invention can be obtained.

Since the quinoxaline derivative described in Embodiment Mode 1 is used for the light-emitting device of the present invention, a light-emitting device having favorable characteristics can be obtained. Specifically, a light-emitting device with low power consumption can be obtained.

The quinoxaline derivative of the present invention is bipolar and has an excellent carrier transporting property (an electron-transporting property and a hole-transporting property); therefore, by using the quinoxaline derivative of the present invention, driving voltage of the light-emitting element can be reduced, resulting in a reduction in the power consumption of a light-emitting device. In particular, in the case of using a phosphorescent substance as a light-emitting substance, a light-emitting device having high emission efficiency and lower power consumption can be obtained.

Figure 6A:
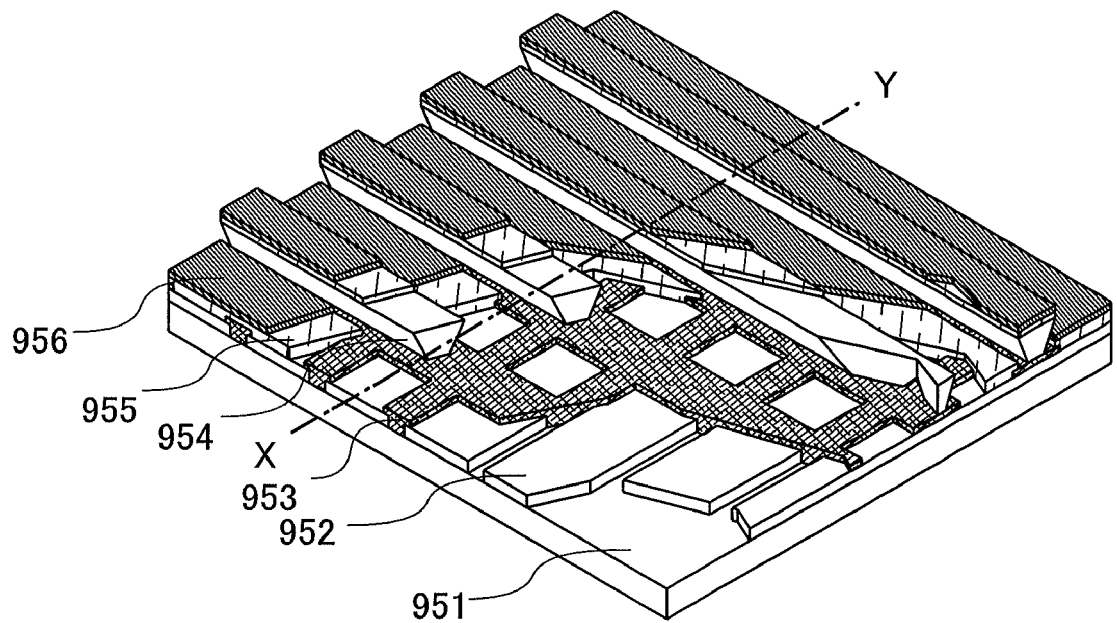
FIGS. 6A and 6B illustrate a light-emitting device according to an aspect of the present invention.
Figure 6B:
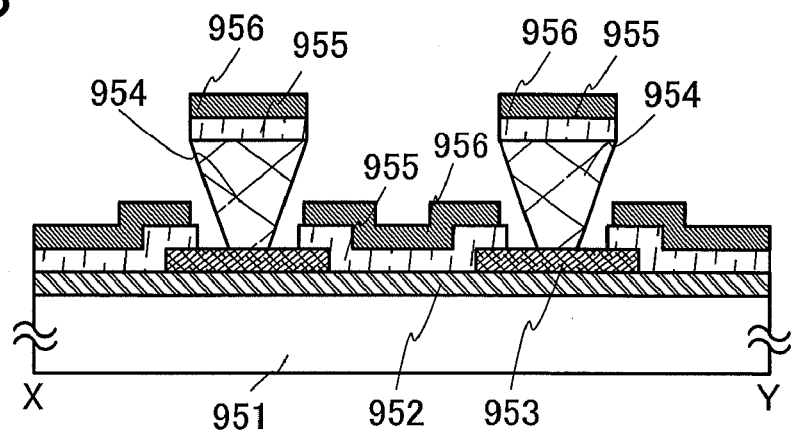

Although an active matrix light-emitting device is described in this embodiment mode as described above, a passive matrix light-emitting device may be alternatively manufactured. FIGS. 6A and 6B are a perspective view and a cross-sectional view of a passive matrix light-emitting device manufactured by applying the present invention. Note that FIG. 6A is a perspective view illustrating the light-emitting device and FIG. 6B is a cross-sectional view taken along a line X-Y in FIG. 6A. In FIGS. 6A and 6B, over a substrate 951, an EL layer 955 is provided between an electrode 952 and an electrode 956. The end portion of the electrode 952 is covered with an insulating layer 953. Then, a partition layer 954 is provided over the insulating layer 953. Sidewalls of the partition layer 954 are slope so that the distance between both sidewalls is gradually narrowed toward the surface of the substrate. That is, a cross section taken in the direction of a shorter side of the partition layer 954 has a trapezoidal shape, and the base of the trapezoid (a side of the trapezoid which is parallel to the surface of the insulating layer 953 and is in contact with the insulating layer 953) is shorter than the upper side of the trapezoid (a side of the trapezoid which is parallel to the surface of the insulating layer 953 and is not in contact with the insulating layer 953). By providing the partition layer 954 in this manner, defects of the light-emitting element due to static charge or the like can be prevented. Further, by including a light-emitting element of the present invention, which can operate at a low driving voltage, a passive matrix light-emitting device can also be driven with low power consumption.

Embodiment Mode 8

In this embodiment mode, electronic devices of the present invention including the light-emitting device described in Embodiment Mode 6 are described. The electronic devices of the present invention each include the quinoxaline derivative described in Embodiment Mode 1 and thus have a display portion with reduced power consumption. Further, the electronic devices of the present invention each have a display portion having long life. Further, the electronic devices of the present invention each have a display portion which can provide high quality images.

As examples of the electronic devices including a light-emitting element manufactured using the quinoxaline derivative of the present invention, there are televisions, cameras such as video cameras and digital cameras, goggle type displays (head-mounted displays), navigation systems, audio replay devices (e.g., car audio systems and audio systems), computers, game machines, portable information terminals (e.g., mobile computers, cellular phones, portable game machines, and electronic book readers), image replay devices in which a recording medium is provided (devices that are capable of replaying recording media such as digital versatile discs (DVDs) and equipped with a display device that can display an image), and the like. Specific examples of these electronic devices are illustrated in FIGS. 7A to 7D.

Figure 7A:
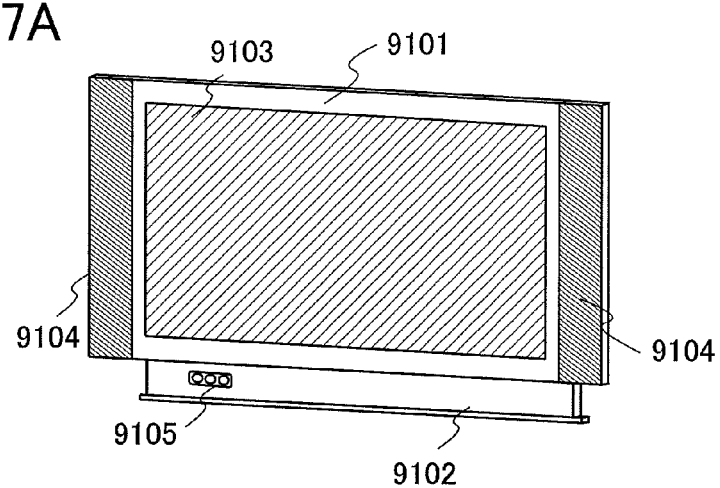
FIGS. 7A to 7D illustrate electronic devices according to an aspect of the present invention.

FIG. 7A illustrates a television set according to the present invention, which includes a housing 9101, a supporting base 9102, a display portion 9103, speaker portions 9104, a video input terminal 9105, and the like. In this television set, the display portion 9103 has light-emitting elements similar to those described in Embodiment Modes 2 to 5, and the light-emitting elements are arranged in matrix. The features of the light-emitting element are represented by high emission efficiency and low power consumption. Since the display portion 9103 including such light-emitting elements has similar features, low power consumption is achieved for this television set. Since such features contribute to a significant reduction and downsizing of a power source circuit etc. in the television set, small sized and lightweight housing 9101 and supporting base 9102 can be achieved. In the television set according to the present invention, low power consumption, high image quality, and small size and lightweight are achieved; thus, products suitable for living environment can be provided.

Figure 7B:
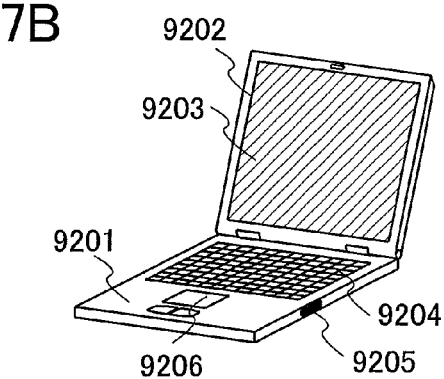

FIG. 7B illustrates a computer according to the present invention, which includes a main body 9201, a housing 9202, a display portion 9203, a keyboard 9204, an external connection port 9205, a pointing device 9206, and the like. In this computer, the display portion 9203 has light-emitting elements similar to those described in Embodiment Modes 2 to 5, and the light-emitting elements are arranged in matrix. The features of the light-emitting element are represented by high emission efficiency and low power consumption. Since the display portion 9203 including such light-emitting elements has similar features, low power consumption is achieved for this computer. Since such features contribute to a significant reduction and downsizing of a power source circuit etc. in the computer, small sized and lightweight main body 9201 and housing 9202 can be achieved. In the computer according to the present invention, low power consumption, high image quality, and small size and lightweight are achieved; thus, products suitable for the environment can be supplied.

Figure 7C:
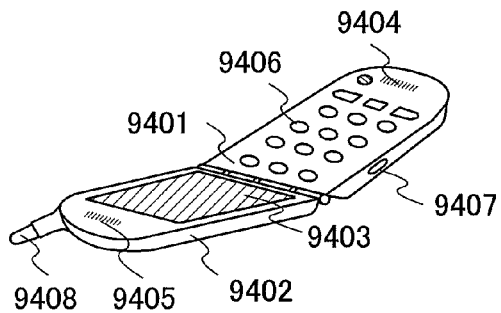

FIG. 7C illustrates a cellular phone according to the present invention, which includes a main body 9401, a housing 9402, a display portion 9403, an audio input portion 9404, an audio output portion 9405, an operation key 9406, an external connection port 9407, an antenna 9408, and the like. In this cellular phone, the display portion 9403 has light-emitting elements similar to those described in Embodiment Modes 2 to 5, and the light-emitting elements are arranged in matrix. The features of the light-emitting element are represented by high emission efficiency and low power consumption. Since the display portion 9403 including such light-emitting elements has similar features, low power consumption is achieved for this cellular phone. Since such features contribute to a significant reduction and downsizing of a power source circuit etc. in the cellular phone, small sized and lightweight main body 9401 and housing 9402 can be supplied. In the cellular phone according to the present invention, low power consumption, high image quality, and a small size and lightweight are achieved; thus, products suitable for portability can be provided.

Figure 7D:
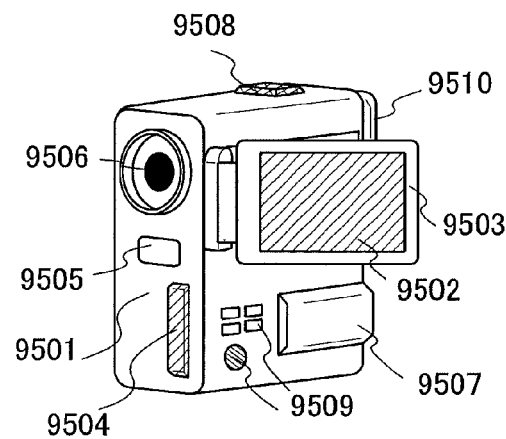

FIG. 7D illustrates a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In this camera, the display portion 9502 has light-emitting elements similar to those described in Embodiment Modes 2 to 5, and the light-emitting elements are arranged in matrix. The features of the light-emitting element are represented by high emission efficiency and low power consumption. Since the display portion 9502 including such light-emitting elements has similar features, low power consumption is achieved for this camera. Since such features contribute to a significant reduction and downsizing of a power source circuit etc. in the camera, a small sized and lightweight main body 9501 can be supplied. In the camera according to the present invention, low power consumption, high image quality, and small size and lightweight are achieved; thus, products suitable for portability can be provided.

As described above, the applicable range of the light-emitting devices of the present invention is wide so that these light-emitting devices can be applied to electronic devices of a variety of fields. By using the quinoxaline derivative of the present invention, an electronic device which has a display portion having low power consumption and excellent color reproducibility can be provided.

Further, such light-emitting devices of the present invention can also be used for a lighting apparatus. One mode using a light-emitting element of the present invention for the lighting apparatus is described using FIG. 8.

Figure 8:
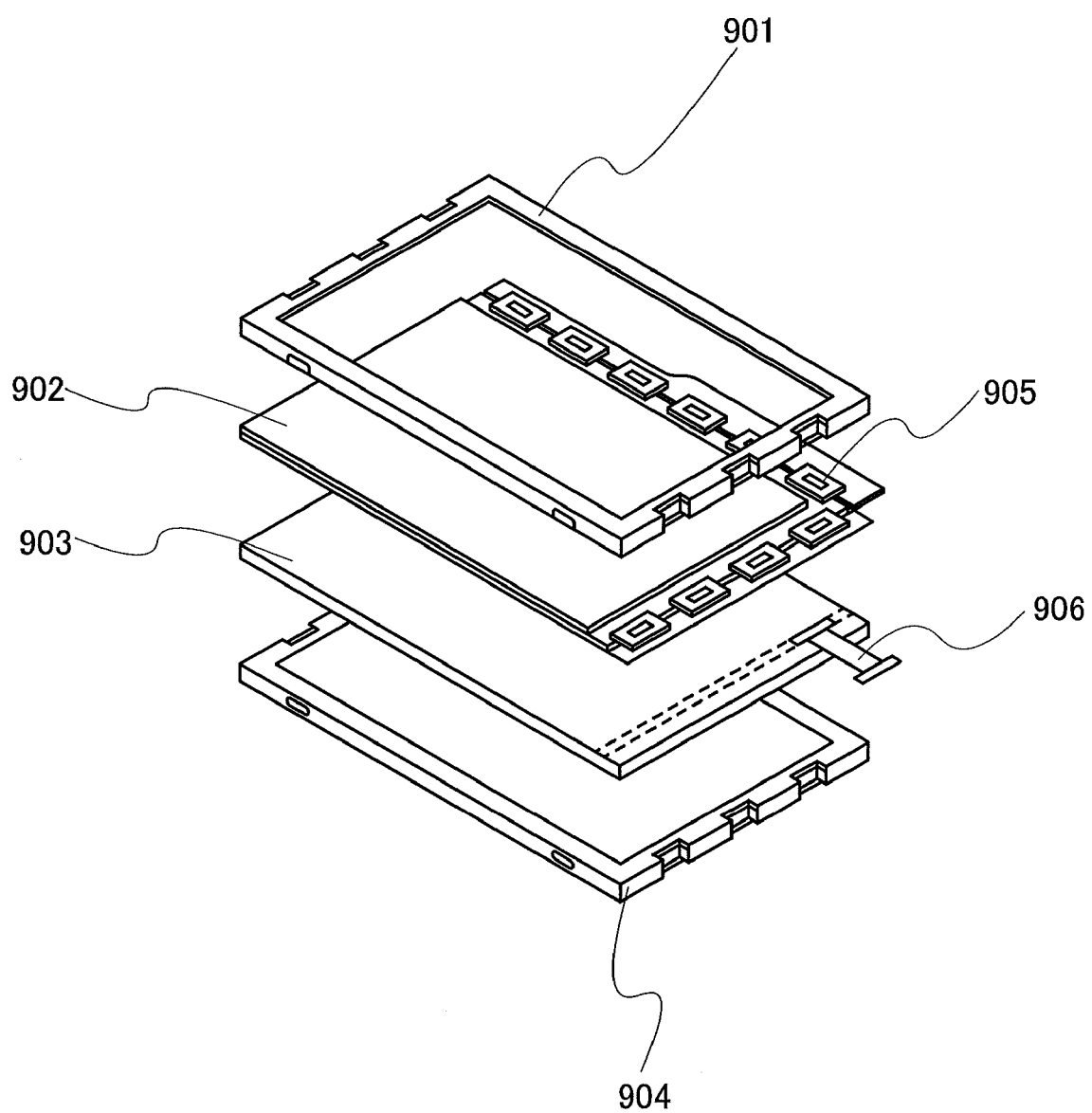
FIG. 8 illustrates an electronic device according to an aspect of the present invention.

FIG. 8 illustrates an example of a liquid crystal display device using the light-emitting device of the present invention as a backlight. The liquid crystal display device illustrated in FIG. 8 includes a housing 901, a liquid crystal layer 902, a backlight 903, and a housing 904, and the liquid crystal layer 902 is connected to a driver IC 905. Further, the light-emitting device of the present invention is used as the backlight 903, and a current is supplied through a terminal 906.

By using the light-emitting device of the present invention as the backlight of the liquid crystal display device, a backlight with reduced power consumption can be obtained. Further, since the light-emitting device of the present invention is a lighting apparatus with plane light emission and can have a larger area, the area of the backlight can be increased, and thus the area of the liquid crystal display device can be increased. Furthermore, since the light-emitting device of the present invention is thin and consumes low power, a thin shape and low power consumption of a display device can also be achieved.

Figure 9:
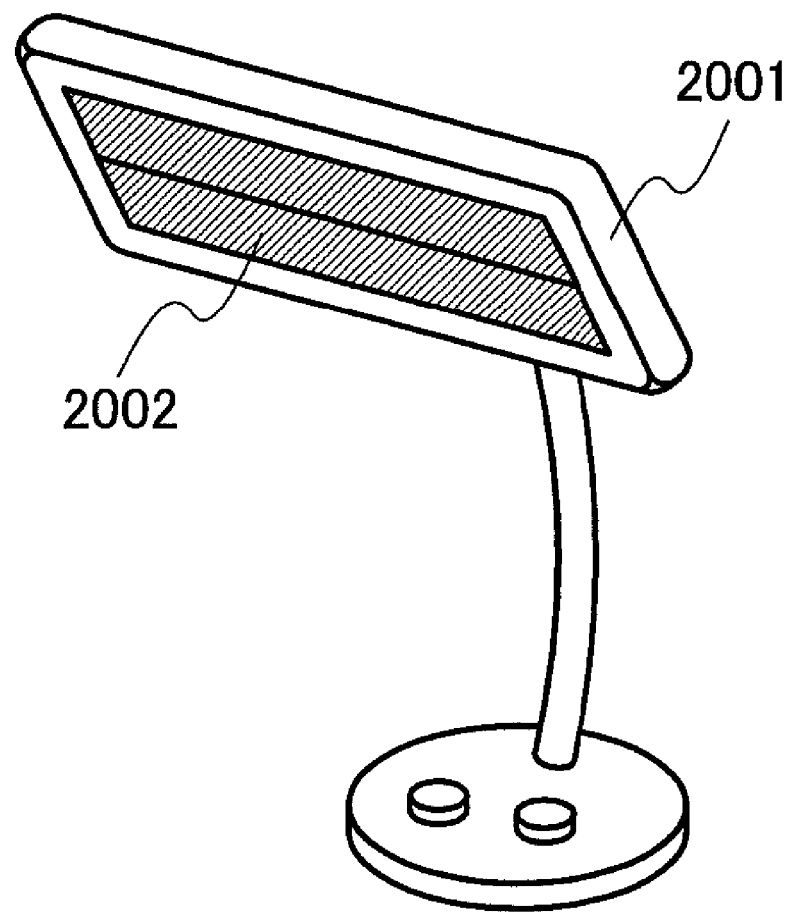
FIG. 9 illustrates a lighting apparatus according to an aspect of the present invention.

FIG. 9 illustrates an example of using the light-emitting device to which the present invention is applied, as a desk lamp which is an example of a lighting apparatus. The desk lamp illustrated in FIG. 9 has a housing 2001 and a light source 2002, and the light-emitting device of the present invention is used as the light source 2002. Since the light-emitting device of the present invention can emit light with high luminance, it can brightly illuminate the area where detail work or the like is being done.

Figure 10:
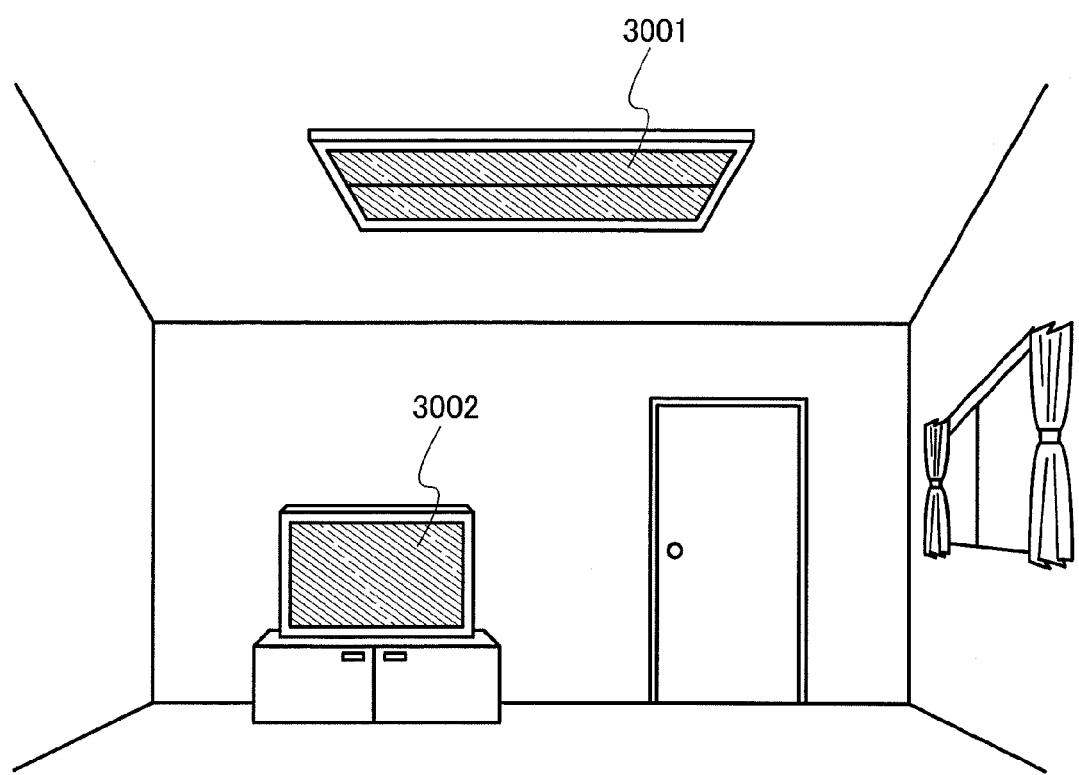
FIG. 10 illustrates a lighting apparatus according to an aspect of the present invention.

FIG. 10 illustrates an example of using a light-emitting device to which the present invention is applied, as an indoor lighting apparatus 3001. Since the light-emitting device of the present invention can have a larger area, the light-emitting device of the present invention can be used as a lighting apparatus having a large emission area. Further, since the light-emitting device of the present invention is thin and consumes low power, the light-emitting device of the present invention can be used as a lighting apparatus which is thin and consumes low power. In a room where the light-emitting device to which the present invention is applied is used as the indoor lighting apparatus 3001 in this manner, a television set 3002 according to the present invention, as illustrated in FIG. 7A, is placed so that public broadcasting and movies can be watched.

EXAMPLE 1

Synthesis Example 1

In Synthesis Example 1, a synthesis example of 4,4'-bis(3-phenylquinoxalin-2-yl)triphenylamine (abbreviation: PQ2A), which is the quinoxaline derivative of the present invention and represented by the structural formula (1) in Embodiment Mode 1, is described in specific terms.

[Step 1]

A synthesis method of 2-(4-bromophenyl)-3-phenylquinoxaline, which is an intermediate in the synthesis of PQ2A, is described.

(i) Synthesis of (4-bromophenyl)phenylacetylene

A synthesis scheme of (4-bromophenyl)phenylacetylene is shown in (B-1).

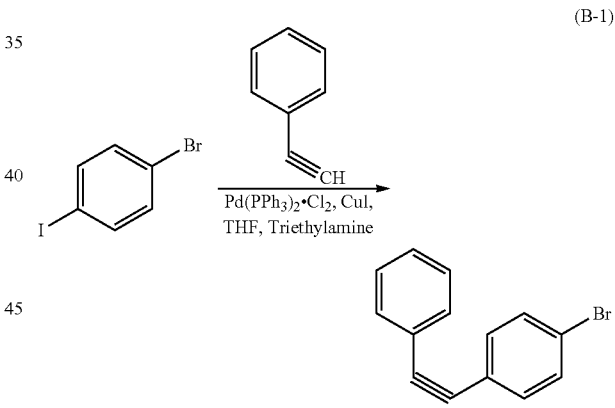

(B-1)

Into a 1000-mL three-neck flask were added 28.3 g (0.10 mol) of p-bromoiodobenzene, 10.2 g (0.10 mol) of phenylacetylene, 701 mg (1 mmol) of bis(triphenylphosphine)palladium(II)dichloride, and 190 mg (1 mmol) of copper(I) iodide, and nitrogen substitution was carried out. Then, 350 mL of tetrahydrofuran and 18 mL of triethylamine were added thereto, and the mixture was stirred at room temperature for 12 hours. After the reaction, the reaction mixture was washed with a 3% hydrochloric acid aqueous solution, and an aqueous phase was extracted with ethyl acetate. The extract combined with an organic phase was washed with a saturated saline solution and then dried with magnesium sulfate. The mixture was filtered through Celite (produced by Wako Pure Chemical Industries, Ltd., Catalog No. 531-16855, the same product was used hereinafter), Florisil (produced by Wako Pure Chemical Industries, Ltd., Catalog No. 540-00135, the same product was used hereinafter), and alumina, and a solid obtained by the concentration of the filtrate was recrystallized with hexane to give 15 g of the target product as a solid at a yield of 58%.

(ii) Synthesis of 1-(4-bromophenyl)-2-phenylethanedione

A synthesis scheme of 1-(4-bromophenyl)-2-phenylethanedione is shown in (B-2).

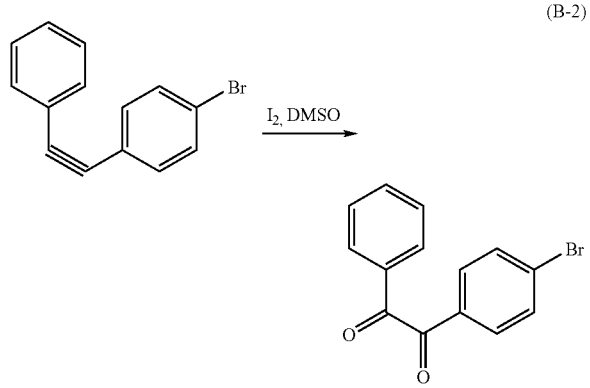

(B-2)

Into a 300-mL three-neck flask were added 10.0 g (38.9 mmol) of (4-bromophenyl)phenylacetylene synthesized by (i), 4.7 g (18.5 mmol) of iodine, and 100 mL of dimethyl sulfoxide, and the mixture was stirred at 155° C. for 4 hours. After the reaction, the reaction solution was cooled and then put into a 1 wt % sodium sulfate aqueous solution to precipitate a solid. The precipitated solid was collected by suction filtration. The collected residue was dissolved in ethanol, and then the solution was filtered through Celite. The filtrate was concentrated, and the obtained solid was dissolved in ethyl acetate. The solution was filtered again through Celite. The filtrate was concentrated to precipitate a solid. The obtained solid was recrystallized with ethyl acetate and hexane, giving 1.5 g of the target product as a solid. The filtrate from which the solid of the target product has been obtained was again recrystallized with acetone and hexane, giving 6.7 g of the target product as a solid. The total weight of the solid of the target product obtained by the two-time recrystallization was 8.2 g and the yield of the product was 72 %.

(iii) Synthesis of 2-(4-bromophenyl)-3-phenylquinoxaline

A synthesis scheme of 2-(4-bromophenyl)-3-phenylquinoxaline is shown in (B-3).

(B-3)

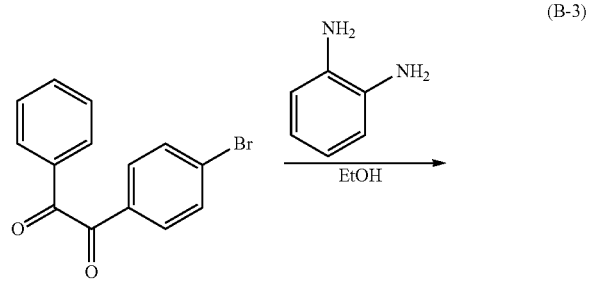

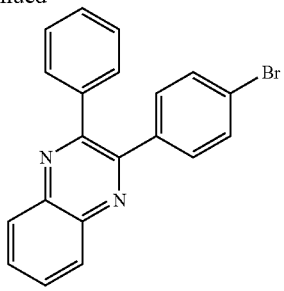

Into a 300-mL flask were added 8.2 g (29 mmol) of 1-(4-bromophenyl)-2-phenylethanedione obtained by (ii), 3.1 g (31 mmol) of o-phenylenediamine, and 100 mL of ethanol, and the mixture was refluxed for 2 hours. After the reaction, the precipitated solid was collected by suction filtration. The collected solid was washed with ethanol and dried, giving 7.3 g of the target product as a light-yellow solid at a yield of 69%.

[Step 2]

A synthesis method of 4,4'-bis(3-phenylquinoxalin-2-yl)triphenylamine, which is the quinoxaline derivative of the present invention, is described.

(i) Synthesis Method of 4-(3-phenylquinoxalin-2-yl)diphenylamine

A synthesis scheme of 4-(2-phenyl-quinoxalin-3-yl)diphenylamine is shown in (B-4).

(B-4)

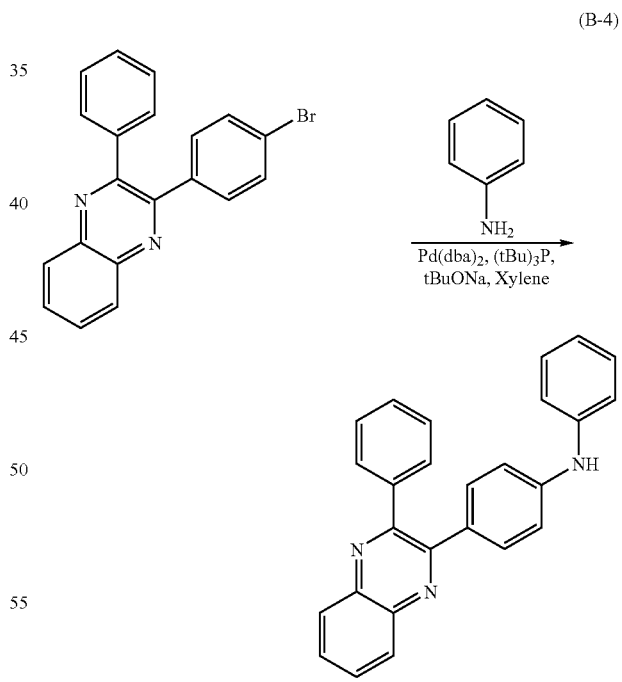

Into a 100-mL three-neck flask were added 3.6 g (10 mmol) of 2-(4-bromophenyl)-3-phenylquinoxaline synthesized by (iii) of Step 1, 1.5 g (15 mmol) of aniline, 290 mg (0.5 mmol) of bis(dibenzylideneacetone)palladium(0), 3.0 mL (15 mmol) of tri(tert-butyl)phosphine (a 10 wt % hexane solution), and 1.5 g (15 mmol) of sodium-tert-butoxide; 20 mL of dehydrated xylene was added to this mixture; and the mixture was heated and stirred under a nitrogen atmosphere at 130° C.

for 2.5 hours. After the termination of the reaction, about 300 mL of toluene was added to the suspension which was the reaction solution, and this suspension was filtered through Florisil and Celite. The obtained filtrate was washed with water, and then moisture was removed with magnesium sulfate. This suspension was filtered through Florisil, alumina, and Celite, and the obtained filtrate was concentrated, whereby 2.2 g of a brown powder was obtained. Note that the Rf values (hexane:ethyl acetate=2:1) of 4-(3-phenylquinoxalin-2-yl)diphenylamine which was the target product and 2-(4-bromophenyl)-3-phenylquinoxaline were 0.63 and 0.78, respectively, by a silicagel thin layer chromatography (TLC).

(ii) Synthesis Method of 4,4'-bis(3-phenylquinoxalin-2-yl)triphenylamine

A synthesis scheme of 4,4'-bis(3-phenylquinoxalin-2-yl) triphenylamine is shown in (B-5).

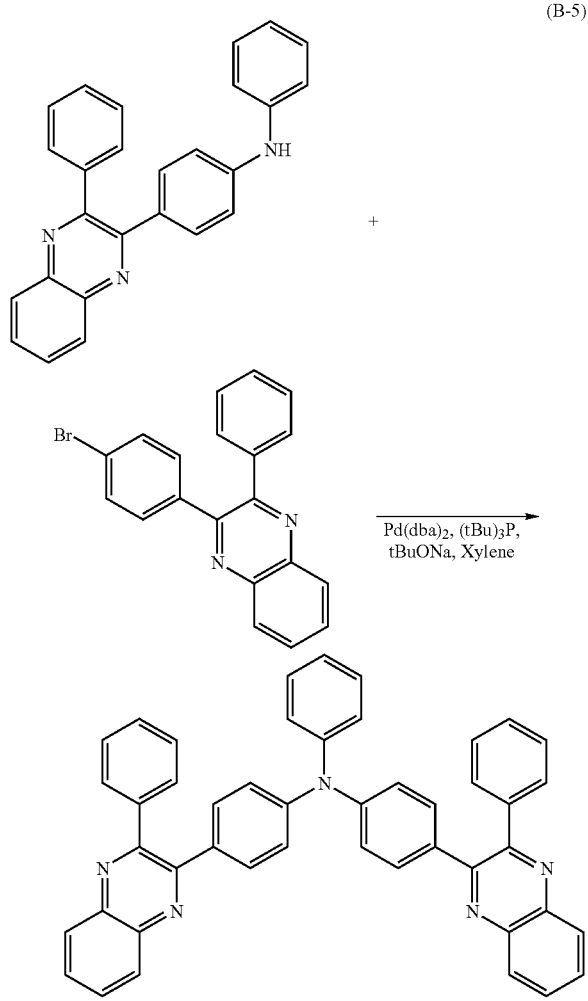

(B-5)

After the above Step 2 (i), 2.2 g of 4-(2-phenyl-quinoxalin-3-yl)diphenylamine, 3.6 g (10 mmol) of 2-(4-bromophenyl)-3-phenylquinoxaline, 212 mg (0.5 mmol) of bis(dibenzylideneacetone)palladium(0), 1.2 mL (0.6 mmol) of tri (tert-butyl) phosphine (a 10 wt % hexane solution), and 1.2 g (12 mmol) of sodium-tert-butoxide were mixed with each other in an 500 mL eggplant-type flask, and 50 mL of dehydrated xylene was added thereto. The mixture was heated and stirred under a nitrogen atmosphere at 120° C. for 6 hours. After the termination of the reaction, about 1 L of a mixed solution (toluene:ethyl acetate=1:1) was added to the suspension which was the reaction solution and this suspension was filtered through Florisil and Celite. The obtained filtrate was washed with water, and then moisture was removed with magnesium sulfate. This suspension was filtered through alumina and Celite, and the obtained filtrate was concentrated. Acetone and hexane were added to the concentrated filtrate, and the mixture was irradiated with ultrasonic waves and then recrsytallized, whereby a yield of 4.5 g of a brown powder was obtained (the total yield from Step 2(i) to this step is 69%). The melting point of this target product was found to be 245° C. by measuring with a differential scanning calorimeter (DSC)

Figure 12A:
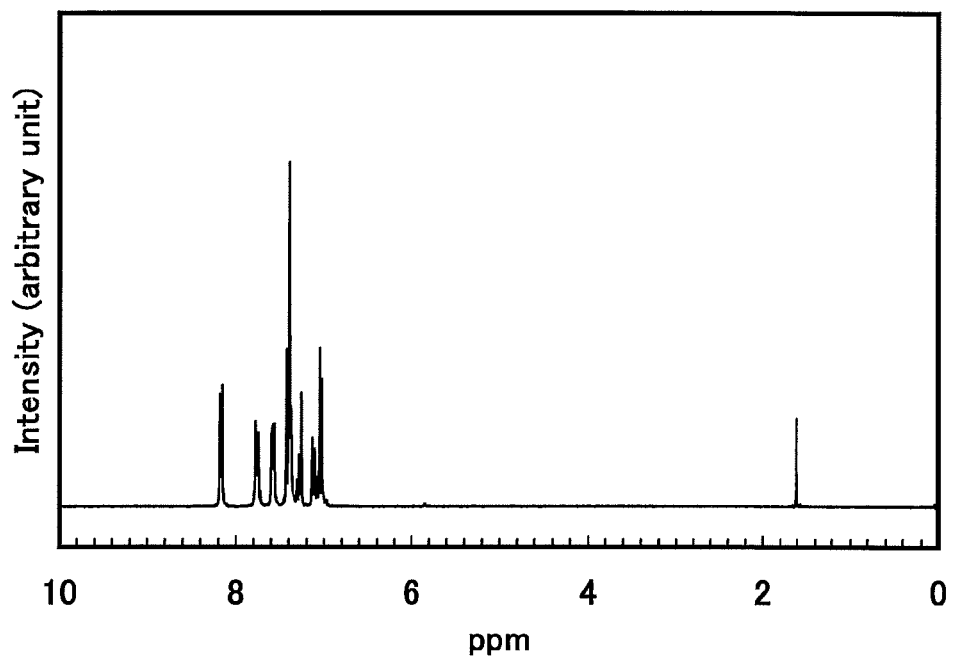
FIGS. 12A and 12B illustrate $^1$H-NMR charts of 4,4'-bis (3-phenylquinoxalin-2-yl)triphenylamine (abbreviation: PQ2A) which is a quinoxaline derivative according to an aspect of the present invention.
Figure 12B:
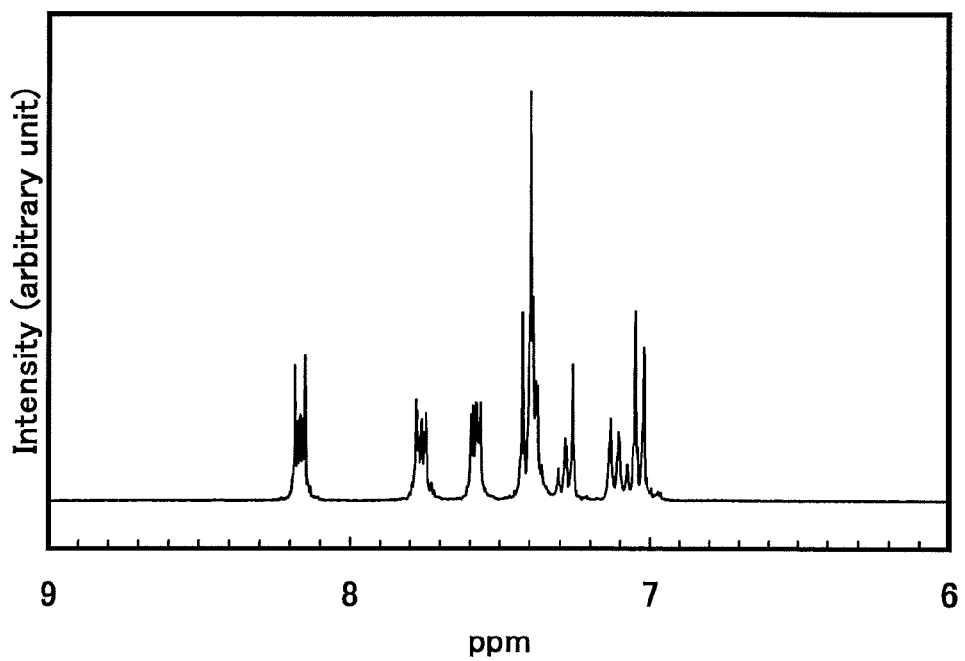
Figure 13A:
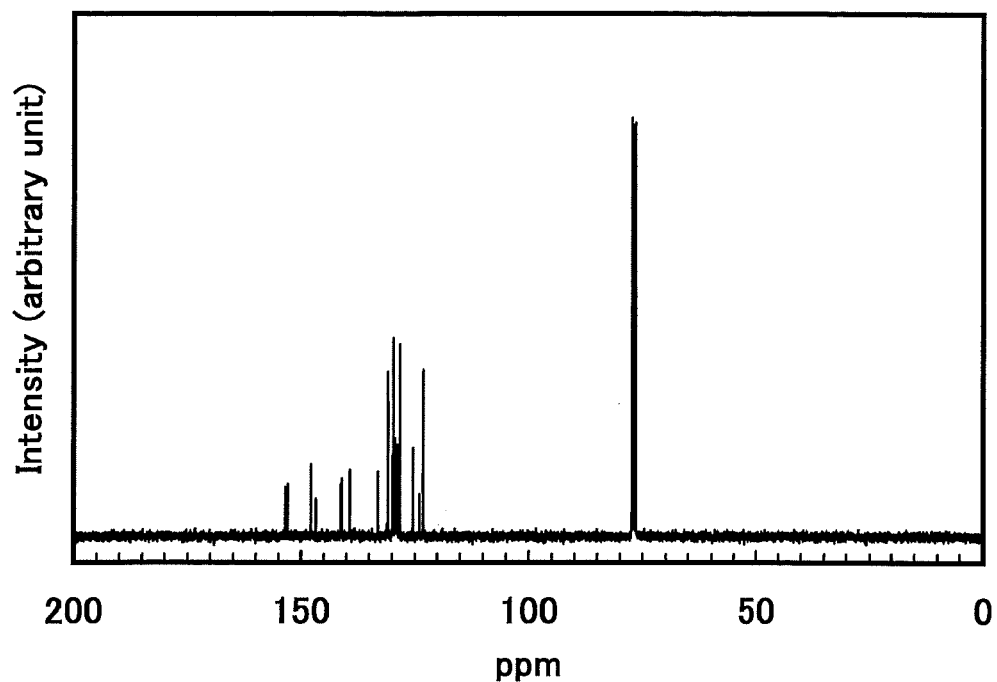
FIGS. 13A and 13B illustrate $^{13}$C-NMR charts of PQ2A which is a quinoxaline derivative according to an aspect of the present invention.
Figure 13B:
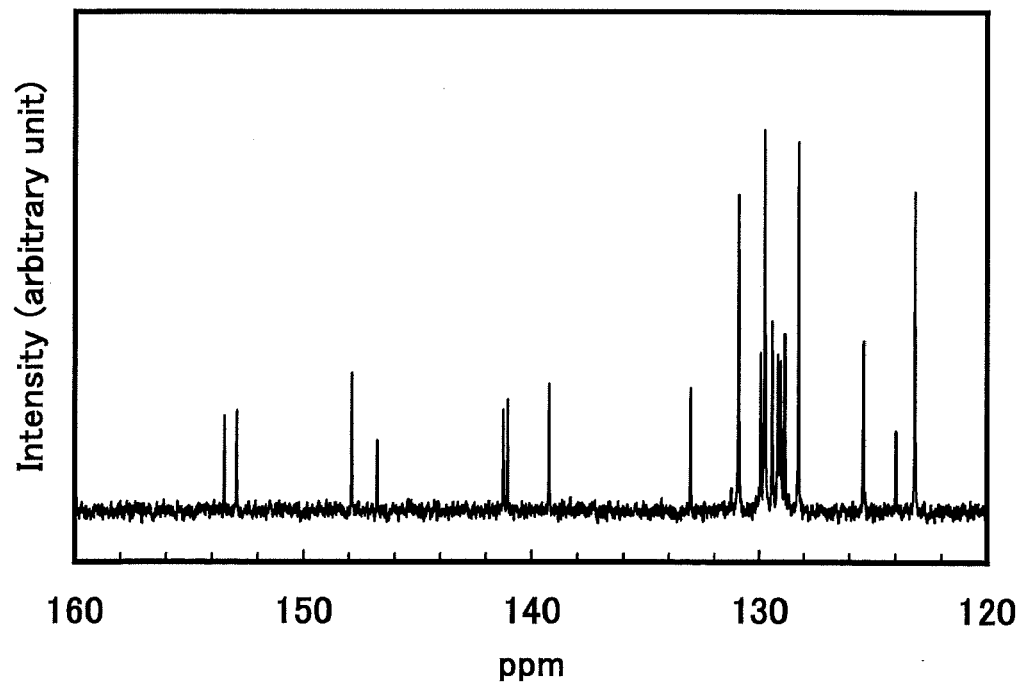

Analysis results of the brown powder obtained by above Step 2, which are obtained by nuclear magnetic resonance spectroscoopy ($^1$H-NMR, $^{13}$C-NMR), are described below. Further, FIGS. 12A and 12B illustrate $^1$H-NMR charts, and FIGS. 13A and 13B illustrate $^{13}$C-NMR charts. From these results, it is confirmed that PQ2A which is the quinoxaline derivative of the present invention and represented by the above structural formula (1) can be obtained in Synthesis Example 1.

$^1$H NMR (300 MHz, CDCl$_3$): δ (ppm)=7.02-7.13 (m, 7H), 7.26-7.43 (m, 12H), 7.56-7.60 (m, 4H), 7.75-7.78 (m, 4H), 8.15-8.18 (m, 4H)

$^{13}$C NMR (75.5 MHz, CDCl$_3$): δ (ppm)=123.1, 124.0, 125.4, 128.2, 128.9, 129.0, 129.2, 129.4, 129.7, 129.7, 129.9, 130.9, 133.0, 139.3, 141.1, 141.2, 146.7, 147.9, 152.9, 153.5

Figure 14:
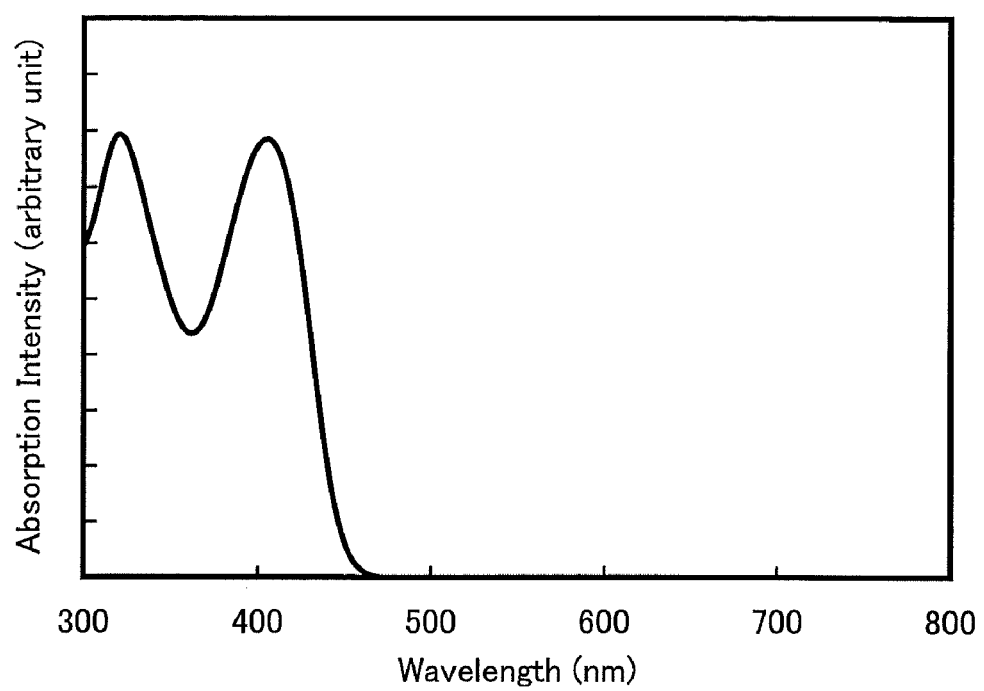
FIG. 14 illustrates an absorption spectrum of a solution of PQ2A which is a quinoxaline derivative according to an aspect of the present invention.
Figure 15:
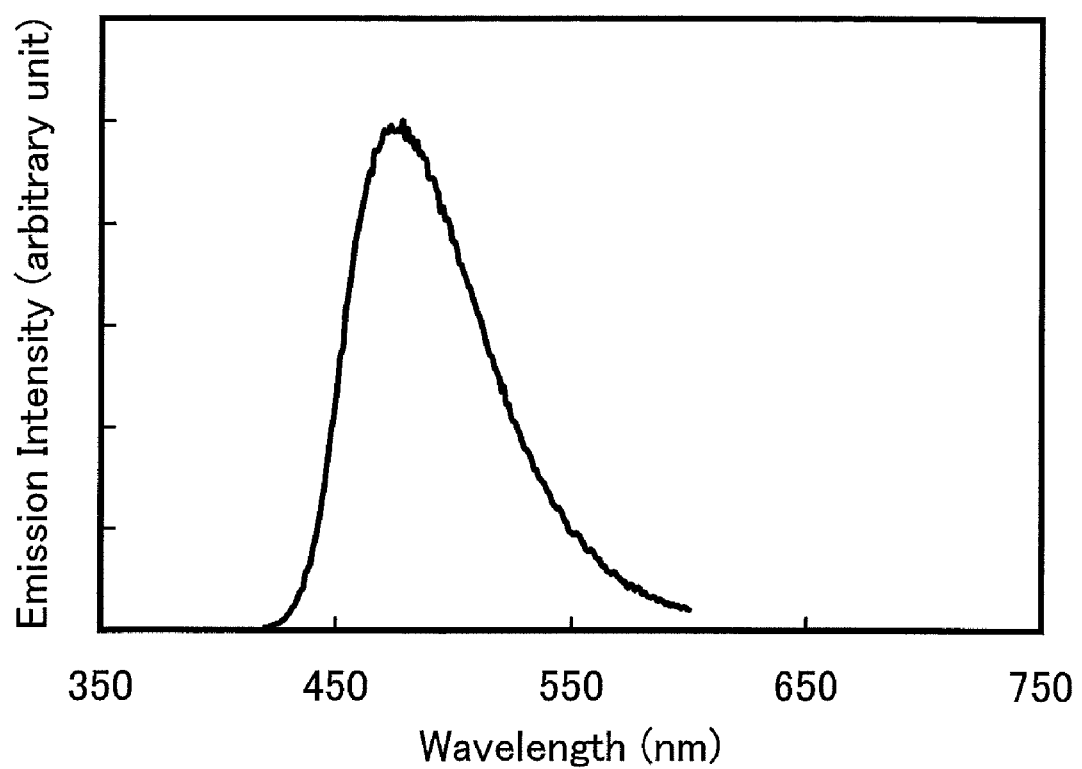
FIG. 15 illustrates an emission spectrum of the solution of PQ2A which is a quinoxaline derivative according to an aspect of the present invention.

Further, FIG. 14 illustrates an absorption spectrum of a toluene solution of PQ2A. In FIG. 14, the horizontal axis indicates the wavelength (nm) and the vertical axis indicates the absorption intensity (arbitrary unit). The solution was put in a quartz cell to be measured. The spectrum in FIG. 14 is an absorption spectrum obtained by subtracting the absorption spectrum of quartz. For the measurements, an ultraviolet-visible spectrophotometer (V-550, manufactured by JASCO Corporation) was used. From these measurements, absorption of the toluene solution of PQ2A was observed at around 406 nm. Further, FIG. 15 illustrates an emission spectrum of the toluene solution of PQ2A (an excitation wavelength of 400 nm). In FIG. 15, the horizontal axis indicates the wavelength (nm) and the vertical axis indicates the emission intensity (arbitrary unit). The maximam emission wavelength was 475 nm (an excitation wavelength of 400 nm).

Figure 16:
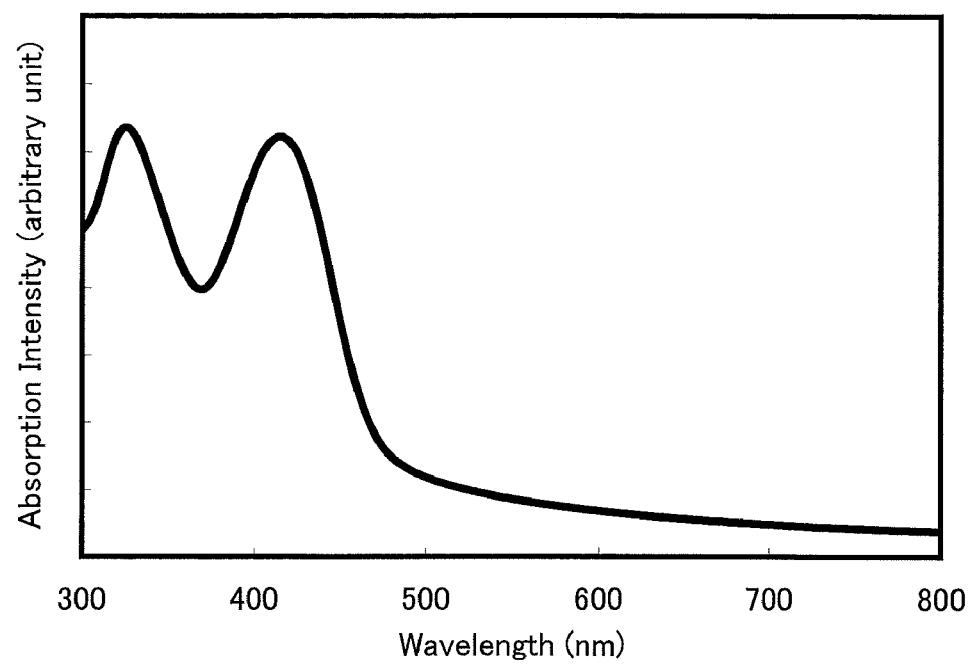
FIG. 16 illustrates an absorption spectrum of a thin film of PQ2A which is a quinoxaline derivative according to an aspect of the present invention.
Figure 17:
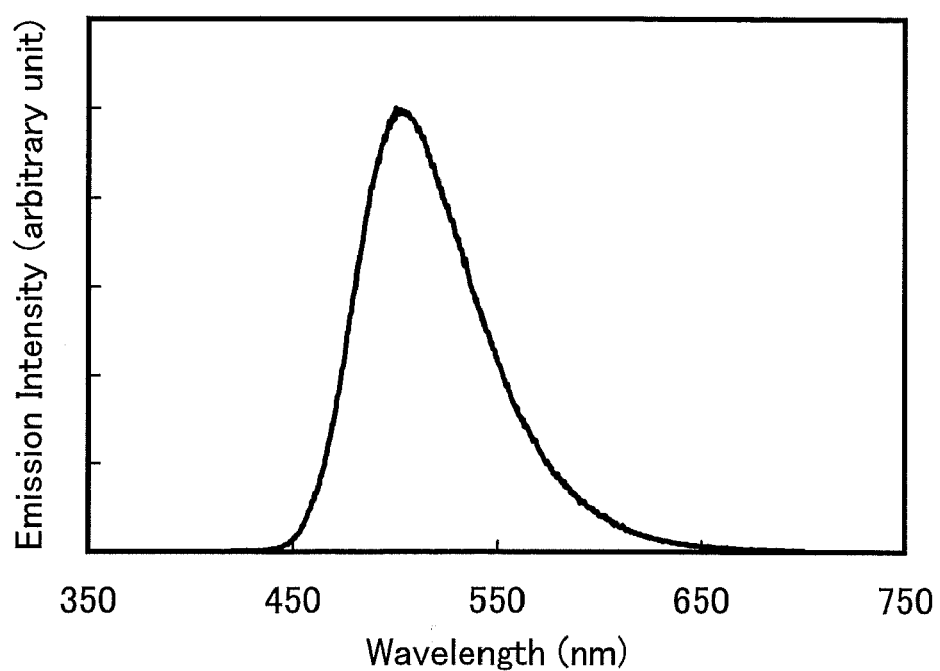
FIG. 17 illustrates an emission spectrum of the thin film of PQ2A which is a quinoxaline derivative according to an aspect of the present invention.

Further, FIG. 16 illustrates an absorption spectrum of a thin film of PQ2A. In FIG. 16, the horizontal axis indicates the wavelength (nm) and the vertical axis indicates the absorption intensity (arbitrary unit). A sample of the thin film- for measurements was prepared by evaporating PQ2A onto a qartz substrate. The spectrum in FIG. 16 is an absorption spectrum obtained by subtracting the absorption spectrum of quartz. For the measurements, an ultraviolet-visible spectrophotometer (V-550, manufactured by JASCO Corporation) was used. As a result, the absorption of the thin film of PQ2A was observed at around 416 nm. Further, FIG. 17 illustrates an emission spectrum of the thin film of PQ2A (an excitation wavelength of 416 nm). In FIG. 17, the horizontal axis indicates the wavelength (nm) and the vertical axis indicates the emission intensity (arbitrary unit). The maximam emission wavelength was 501 nm (an excitation wavelength of 416 nm).

Further, by measurements of this thin film in an atmosphere using a photoelectron spectrometer (AC-2, manufactured by Riken Keiki Co., Ltd.), the HOMO level of this thin film was −5.53 eV. From the Tauc plot of the absorption spectrum in FIG. 16, the absorption edge was 2.69 eV. Therefore, the energy gap of PQ2A in the solid state is estimated to be 2.69 eV, which means that the LUMO level of PQ2A is −2.84 eV.

Further, the oxidation reaction characteristics and reduction reaction characteristics of PQ2A were measured. The oxidation reaction characteristics and reduction reaction characteristics were measured by cyclic voltammetry (CV). Note that for the measurements, an electrochemical analyzer (ALS model 600A, manufactured by BAS Inc.) was used.

As a solution used for the CV measurements, dehydrated N,N-dimethylformamide (DMF, produced by Sigma-Aldrich Inc., 99.8%, Catalog No. 22705-6) was used as a solvent. Tetra-n-butylammonium perchlorate (n-Bu$_4$NClO$_4$, produced by Tokyo Chemical Industry Co., Ltd., Catalog No. T0836), which was a supporting electrolyte, was dissolved in the solvent so that the concentration of tetra-n-butylammonium perchlorate was 100 mmol/L. Furthermore, the measurement object was also dissolved in the solvent so that the concentration thereof was 1 mmol/L. Further, as a working electrode, a platinum electrode (a PTE platinum electrode, produced by BAS Inc.) was used. As an auxiliary electrode, a platinum electrode (a VC-3 Pt counter electrode (5 cm), produced by BAS Inc.) was used. As a reference electrode, an Ag/Ag$^+$ electrode (an RE5 nonaqueous solvent reference electrode, produced by BAS Inc.) was used. Note that that the measurements were performed at room temperature.

The reduction reaction characteristics of PQ2A were measured as follows. One cycle was a scan in which the potential of the working electrode with respect to the reference electrode was changed from −0.2 V to −2.3 V and then changed from −2.3 V to −0.2 V, and 100 cycles were performed. Further, the scanning speed of the CV measurements was set to be 0.1 V/s.

Figure 18:
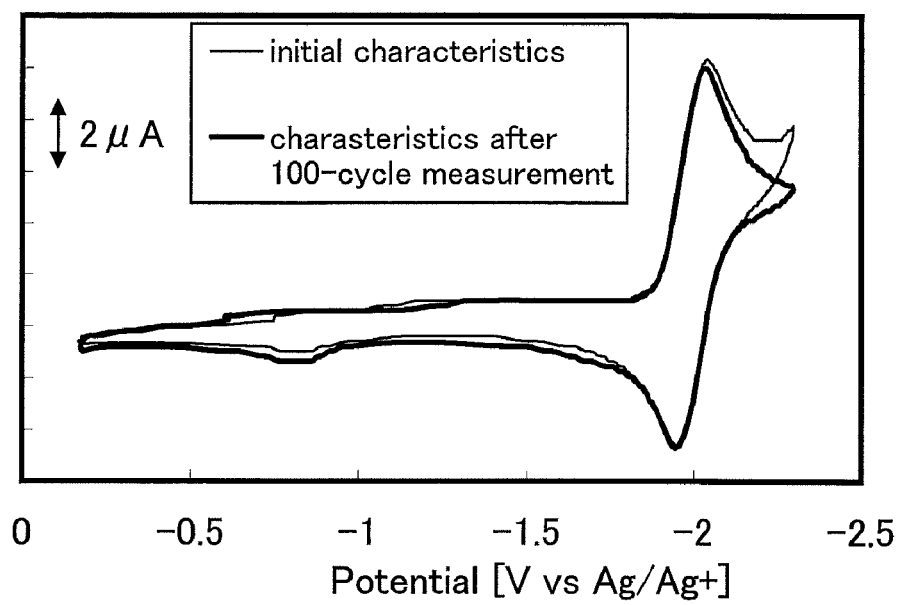
FIG. 18 illustrates results of CV measurements of PQ2A which is a quinoxaline derivative according to an aspect of the present invention.

FIG. 18 illustrates results of the CV measurement of the reduction characteristics of PQ2A. In FIG. 18, the horizontal axis indicates the potential (V) of the working electrode with respect to the reference electrode, and the vertical axis indicates the current value (μA) flowing between the working electrode and the auxiliary electrode. From FIG. 18, a current which represents reduction was observed at around −2.03 V (vs. Ag/Ag$^+$).

Although the scanning was repeated for as many as 100 cycles, PQ2A shows no significant change in the peak position and peak intensity of the CV curve representing a reduction reaction. Thus, it is understood that PQ2A is highly stable even when a reduction reaction from a neutral state to a reduction state and an oxidation reaction from a reduction state to a neutral state are repeated.

EXAMPLE 2

Figure 11:
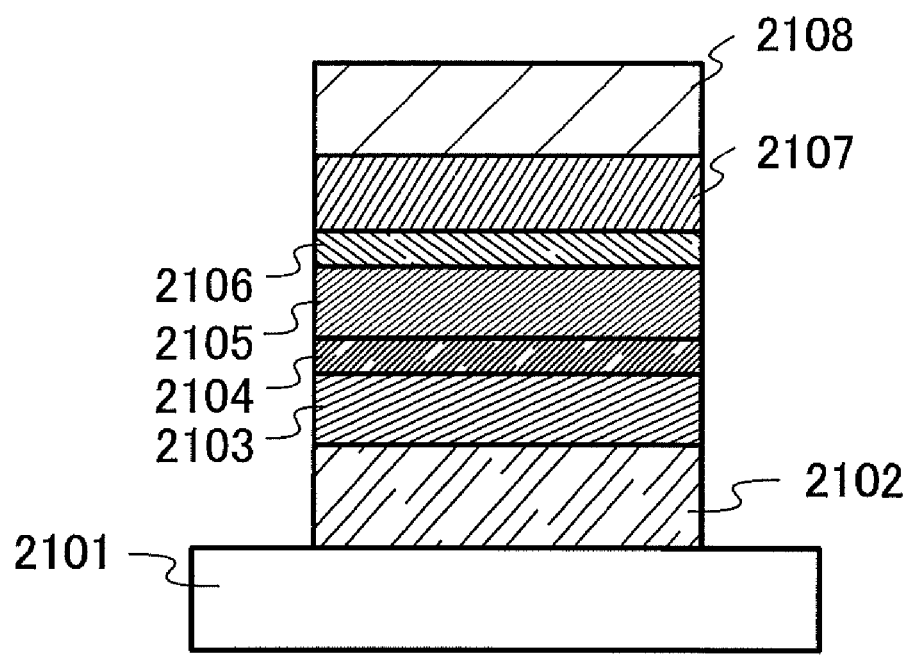
FIG. 11 illustrates a light-emitting element of Examples.

In this example, light-emitting elements of the present invention are described using FIG. 11. Chemical formulae of materials used in this embodiment are shown below.

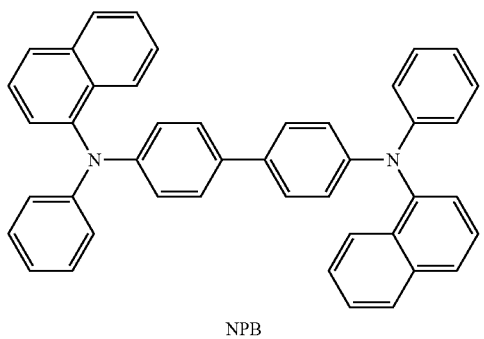

NPB

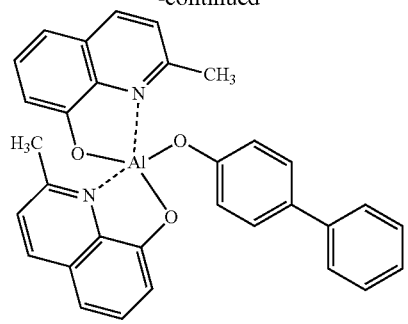

BAlq

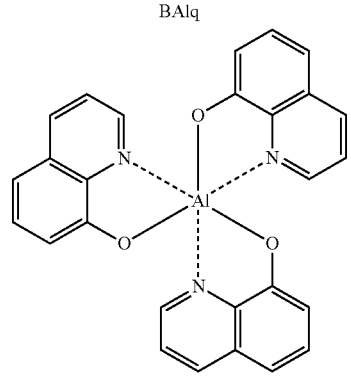

Alq

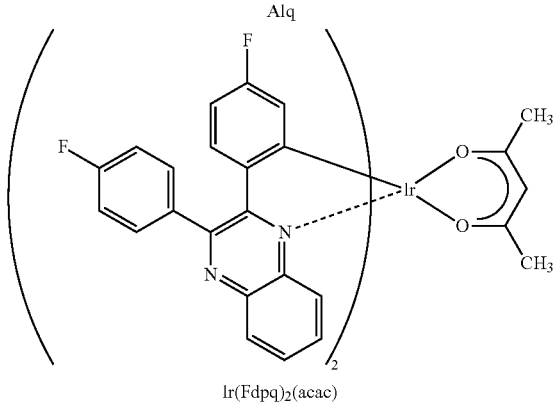

Ir(Fdpq)$_2$(acac)

Hereinafter, a method of manufacturing a light-emitting element of this example is described.

(Light-Emitting Element 1)

First, indium oxide-tin oxide containing silicon oxide was deposited over a glass substrate 2101 by a sputtering method to form a first electrode 2102. Note that the thickness of the first electrode 2102 was set to be 110 nm and that the electrode area was set to be 2 mm by 2 mm.

Next, the substrate over which the first electrode was provided was fixed to a substrate holder provided in a vacuum evaporation apparatus so that the surface provided with the first electrode faced downward. After that, the vacuum evaporation apparatus was evacuated, and the pressure in the vacuum evaporation apparatus was reduced to approximately 10$^{-4}$ Pa. Then, over the first electrode 2102, 4,4'-bis[N-(1-naphthyl)-N-phenylamino]biphenyl (abbreviation: NPB) and molybdenum(VI) oxide were co-evaporated to form a layer 2103 containing a composite material. The thickness of the layer 2103 containing the composite material was set to be 50 nm, and the weight ratio of NPB to molybdenum(VI) oxide was adjusted so as to be 4:1 (=NPB:molybdenum oxide).

Next, NPB was deposited over the layer 2103 containing the composite material to a thickness of 10 nm by an evaporation method using resistive heating to form a hole-transporting layer 2104.

Furthermore, 4,4'-bis(3-phenylquinoxalin-2-yl)triphenylamine (abbreviation: PQ2A) of the present invention, which is represented by the structural formula (1) in Embodiment Mode 1, and (acetylacetonato)bis[2,3-bis(4-fluorophenyl)quinoxalinato]iridium(III) (abbreviation: Ir(Fdpq)$_2$(acac)) were co-evaporated over the hole-transporting layer 2104 to form a light-emitting layer 2105 with a thickness of 30 nm. Here, the weight ratio of PQ2A to Ir(Fdpq)$_2$(acac)) was adjusted so as to be 1:0.06 (=PQ2A:Ir(Fdpq)$_2$(acac)).

Then, tris(8-quinolinolato)aluminum (abbreviation: Alq) was deposited over the light-emitting layer 2105 to a thickness of 10 nm by an evaporation method using resistive heating to form an electron-transporting layer 2106.

Furthermore, over the electron-transporting layer 2106, Alq and lithium were co-evaporated to form an electron-injecting layer 2107 with a thickness of 50 nm. Here, the weight ratio of Alq to lithium was adjusted so as to be 1:0.01 (=Alq:lithium).

Lastly, aluminum was deposited over the electron-injecting layer 2107 to a thickness of 200 nm by an evaporation method using resistive heating to form a second electrode 2108. Accordingly, a light-emitting element 1 was manufactured.

(Light-Emitting Element 2)

A light-emitting element 2 was manufactured in a similar manner to the light-emitting element 1 except that bis(2-methyl-8-quinolinolato)(4-phenylphenolato)aluminum (abbreviation: BAlq) was used instead of Alq used for forming the electron-transporting layer of the light-emitting element 1.

Figure 19:
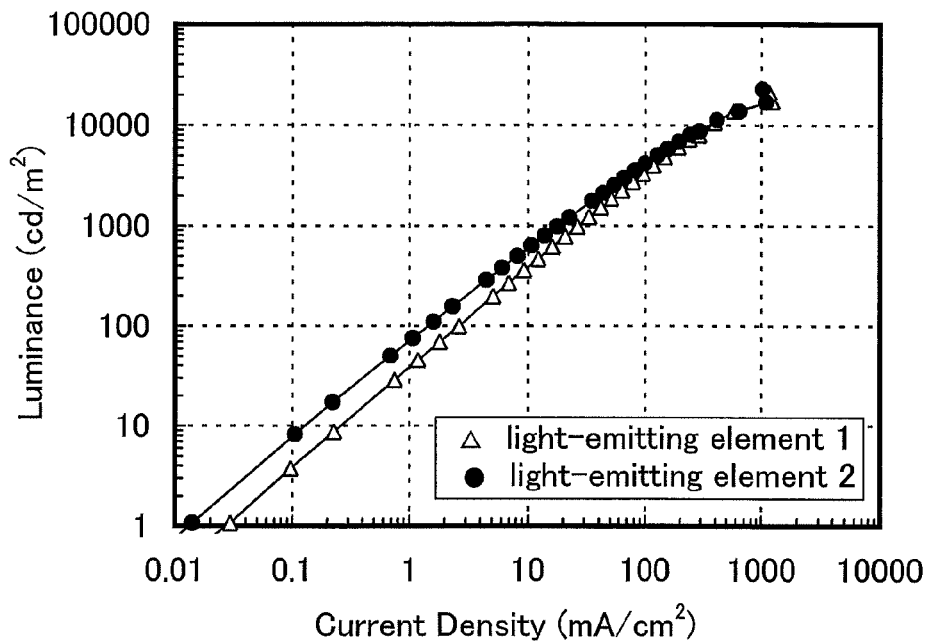
FIG. 19 illustrates the current density vs. luminance characteristics of a light-emitting element 1 and a light-emitting element 2 manufactured in Example 2.
Figure 20:
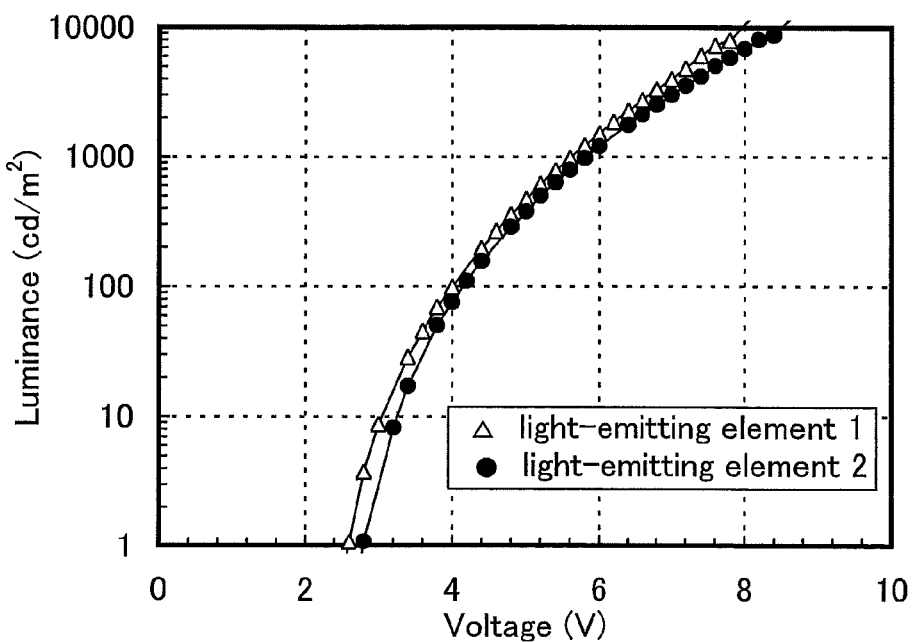
FIG. 20 illustrates the voltage vs. luminance characteristics of the light-emitting element 1 and the light-emitting element 2 manufactured in Example 2.
Figure 21:
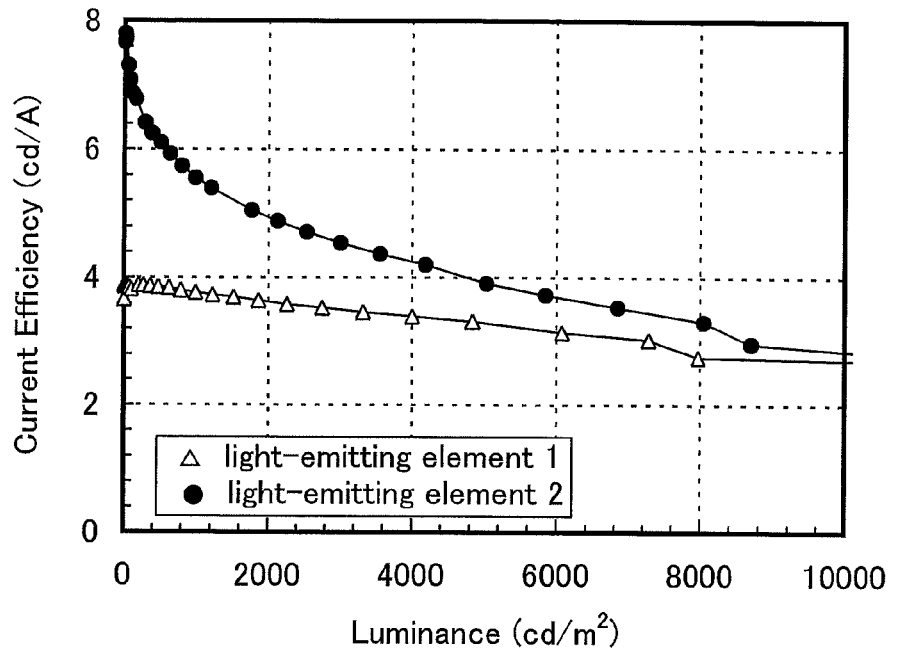
FIG. 21 illustrates the current efficiency vs. luminance characteristics of the light-emitting element 1 and the light-emitting element 2 manufactured in Example 2.
Figure 22:
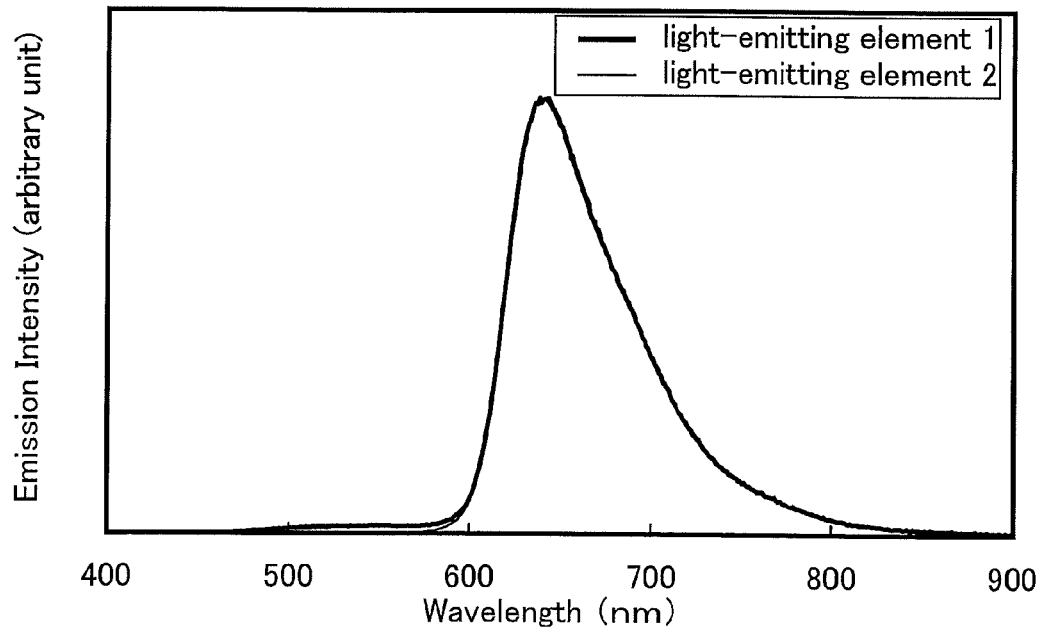
FIG. 22 illustrates the emission spectra of the light-emitting element 1 and the light-emitting element 2 manufactured in Example 2.

FIG. 19 illustrates the current density vs. luminance characteristics of the light-emitting element 1 and the light-emitting element 2; FIG. 20 illustrates the voltage vs. luminance characteristics of the light-emitting elements; and FIG. 21 illustrates the luminance vs. current efficiency characteristics of the light-emitting elements. Also, FIG. 22 illustrates the emission spectra at a current of 1 mA.

At a luminance of 1000 cd/m$^2$, the CIE chromaticity coordinate of the light-emitting element 1 was (x=0.68, y=0.31), and light emission was red. Further, at a luminance of 1000 cd/m$^2$, the current efficiency was 3.8 cd/A, and the external quantum efficiency was 6.3%. In addition, at a luminance of 1000 cd/m$^2$, the voltage was 5.6 V, the current density was 26.2 mA/cm$^2$, and the power efficiency was 2.1 lm/W.

At a luminance of 1000 cd/m$^2$, the CIE chromaticity coordinate of the light-emitting element 2 was (x=0.71, y=0.29), and light emission was red. Further, at a luminance of 1000 cd/m$^2$, the current efficiency was 5.5 cd/A, and the external quantum efficiency was 10%. In addition, at a luminance of 1000 cd/m$^2$, the voltage was 5.8 V, the current density was 17.7 mA/cm$^2$, and the power efficiency was 3.00 lm/W.

Thus, by using the quinoxaline derivative of the present invention, a light-emitting element with low driving power can be obtained.

Further, as can be seen from FIG. 22, both the light-emitting element 1 and the light-emitting element 2 exhibit approximately the same spectrum and can provide light emission from Ir(Fdpq)$_2$(acac). Here, despite the fact that it has been found that Ir(Fdpq)$_2$(acac) used as a light-emitting substance has a low hole-transporting property and a high electron-trapping property, light emission can be obtained efficiently in the light-emitting element 2. Therefore, it is understood that the quinoxaline derivative of the present invention has a hole-transporting property. Further, in the light-emitting element 1, Alq for the electron-transporting layer provided adjacent to the light-emitting layer has a low hole-blocking property, and light is emitted when holes which have not contributed to emission in the light-emitting layer pass through the light-emitting layer. However, light emission is hardly seen in the light-emitting element 1. This results from the fact that almost all the holes contribute to recombination because of the excellent carrier balance in the light-emitting layer. That is, the quinoxaline derivative of the present invention is found to have both an appropriate hole-transporting property and an electron-transporting property, and thus has a bipolar property. Further, according to Examples 1 and 2, it is found that PQ2A used in this example allows Ir(Fdpq)$_2$(acac) which is a material emitting red phosphorescence to be excited to emit light.

This application is based on Japanese Patent Application serial no. 2007-312190 filed with Japan Patent Office on Dec. 3, 2007, the entire contents of which are hereby incorporated by reference.

What is claimed is:

1. A quinoxaline derivative represented by a general formula (G1),

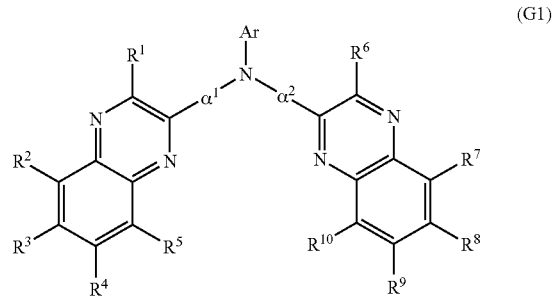

wherein:
$\alpha^1$ and $\alpha^2$ each independently represent an arylene group having 6 to 13 carbon atoms which form an aromatic ring, Ar represents an aryl group having 6 to 13 carbon atoms which form an aromatic ring, $R^1$ and $R^6$ each independently represent any of a hydrogen atom, an alkyl group having 1 to 6 carbon atoms, or an aryl group having 6 to 13 carbon atoms which form an aromatic ring, and $R^2$ to $R^5$ and $R^7$ to $R^{10}$ each independently represent any of a hydrogen atom, an alkyl group having 1 to 6 carbon atoms, a substituted or unsubstituted phenyl group, or a substituted or unsubstituted biphenyl group.

2. The quinoxaline derivative according to claim 1, wherein $\alpha^1$ and $\alpha^2$ in the general formula (G1) each independently represent any of general formulae (2-1) to (2-7) below, and

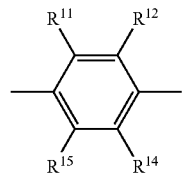

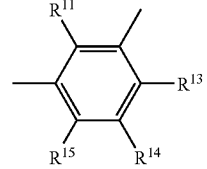

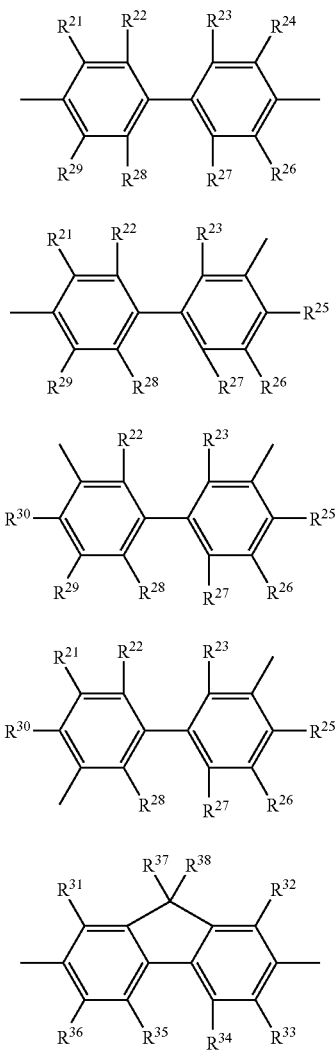

wherein:
R[11] to R[15] and R[21] to R[36] each independently represent any of a hydrogen atom, an alkyl group having 1 to 6 carbon atoms, or a phenyl group, and R[37] and R[38] each independently represent a hydrogen atom or an alkyl group having 1 to 6 carbon atoms.

3. The quinoxaline derivative according to claim 1, wherein Ar in the general formula (G1) is any of general formulae (3-1) to (3-7) below, and

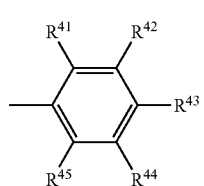

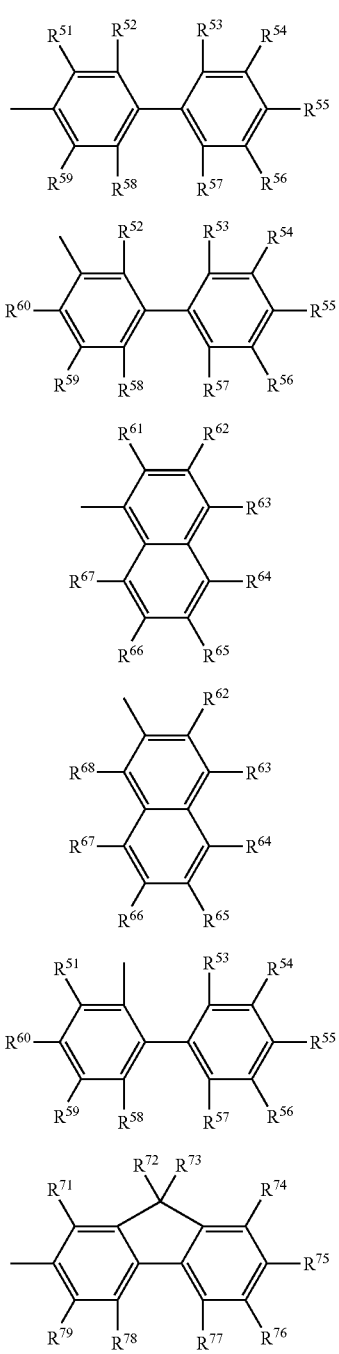

wherein:
R[41] to R[45], Rl to R[68], and R[71] to R[79] each independently represent any of a hydrogen atom, an alkyl group having 1 to 6 carbon atoms, a phenyl group, or a biphenyl group.

4. The quinoxaline derivative according to claim 1, wherein R[1] and R[6] in the general formula (G1) each independently represent any of structural formulae (4-1) to (4-6) or general formulae (4-7) to (4-12), and

—H   (4-1)

—CH$_3$   (4-2)

-continued (4-3) —CH₂CH₃

(4-4) 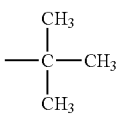

(4-5) —C₆H₁₃

(4-6) 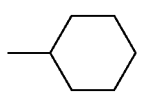

(4-7) 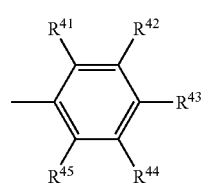

(4-8) 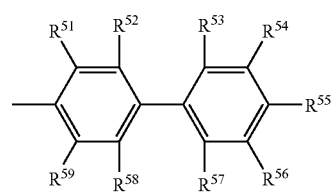

(4-9) 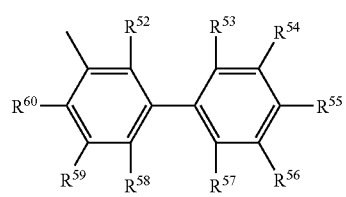

(4-10) 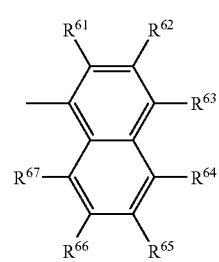

(4-11) 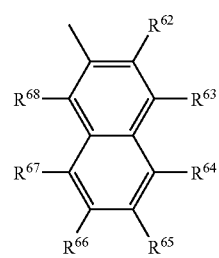

(4-12) 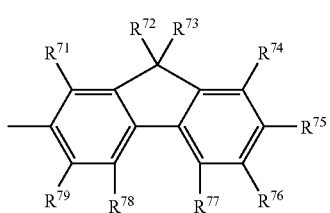

wherein:
$R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

5. The quinoxaline derivative according to claim 1, wherein $R^2$ to $R^5$ and $R^7$ to $R^{10}$ in the general formula (G1) each independently represent any of structural formulae (5-1) to (5-6) or general formulae (5-7) to (5-10), and (5-1) —H (5-2) —CH₃

(5-3) —CH₂CH₃

(5-4)

$$\begin{array}{c} CH_3 \\ | \\ -C-CH_3 \\ | \\ CH_3 \end{array}$$

(5-5) —C₆H₁₃

(5-6)

(5-7)

(5-8)

(5-9)

(5-10)

wherein $R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

6. The quinoxaline derivative according to claim 1, wherein Ar, $R^1$, and $R^6$ each represent an unsubstituted phenyl group,
wherein $\alpha^1$ and $\alpha^2$ each represent a phenylene group, and
wherein $R^2$ to $R^5$ and $R^7$ to $R^{10}$ each represent a hydrogen atom.

7. A light-emitting element comprising:

a first electrode;

an EL layer over the first electrode; and a second electrode over the EL layer, wherein the EL layer comprises a quinoxaline derivative represented by a general formula (G1), and

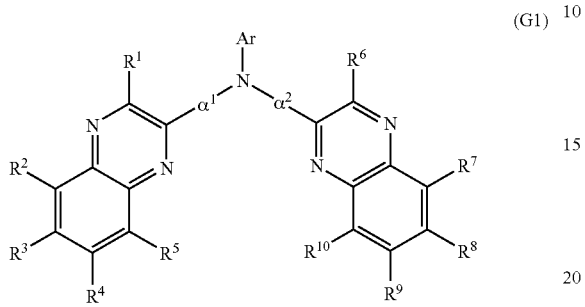

(G1)

wherein:

α¹ and α² each independently represent an arylene group having 6 to 13 carbon atoms which form an aromatic ring, Ar represents an aryl group having 6 to 13 carbon atoms which Balla an aromatic ring, R¹ and R⁶ each independently represent any of a hydrogen atom, an alkyl group having 1 to 6 carbon atoms, or an aryl group having 6 to 13 carbon atoms which form an aromatic ring, and R² to R⁵ and R⁷ to R¹⁰ each independently represent any of a hydrogen atom, an alkyl group having 1 to 6 carbon atoms, a substituted or unsubstituted phenyl group, or a substituted or unsubstituted biphenyl group.

8. The light-emitting element according to claim 7, wherein the EL layer further comprises a fluorescent substance.

9. The light-emitting element according to claim 7, wherein the EL layer further comprises a phosphorescent substance.

10. The light-emitting element according to claim 7, wherein α¹ and α² in the general formula (G1) each independently represent any of general formulae (2-1) to (2-7) below, and wherein:

R to R¹⁵ and R²¹ to R³⁶ each independently represent any of a hydrogen atom, an alkyl group having 1 to 6 carbon atoms, or a phenyl group, and R³⁷ and R³⁸ each independently represent a hydrogen atom or an alkyl group having 1 to 6 carbon atoms.

11. The light-emitting element according to claim 7, wherein Ar in the general formula (G1) is any of general formulae (3-1) to (3-7) below, and

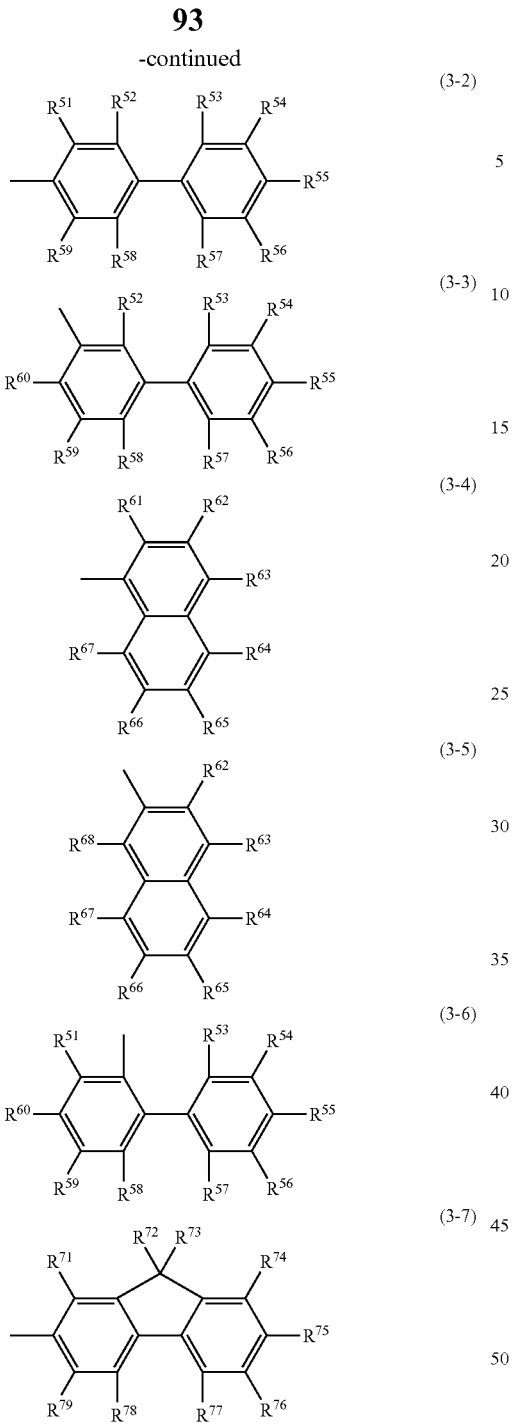

(3-2)
(3-3)
(3-4)
(3-5)
(3-6)
(3-7)

wherein:
$R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

12. The light-emitting element according to claim 7, wherein $R^1$ and $R^6$ in the general formula (G1) each independently represent any of structural formulae (4-1) to (4-6) or general formulae (4-7) to (4-12), and

—H  (4-1)

—CH$_3$  (4-2)

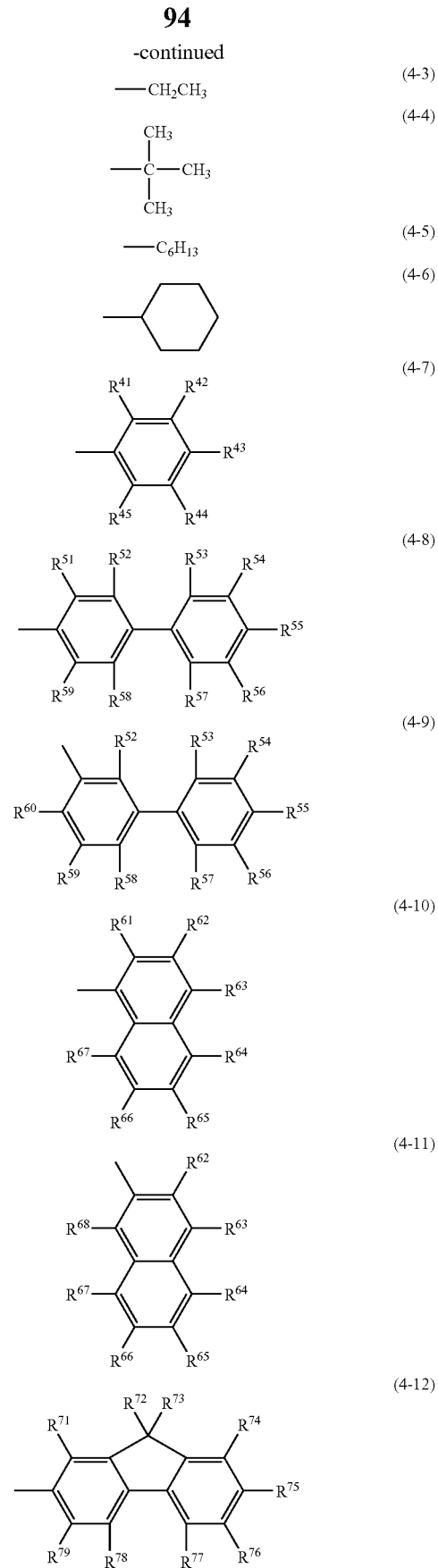

—CH$_2$CH$_3$  (4-3)

(4-4)

—C$_6$H$_{13}$  (4-5)

(4-6)

(4-7)
(4-8)
(4-9)
(4-10)
(4-11)
(4-12)

wherein:
R$^{41}$ to R$^{45}$, R$^{51}$ to R$^{68}$, and R$^{71}$ to R$^{79}$ each independently represent any of a hydrogen atom, an alkyl group having 1 to 6 carbon atoms, a phenyl group, or a biphenyl group.

13. The light-emitting element according to claim 7, wherein R$^2$ to R$^5$ and R$^7$ to R$^{10}$ in the general formula (G1) each independently represent any of structural formulae (5-1) to (5-6) or general formulae (5-7) to (5-10), and

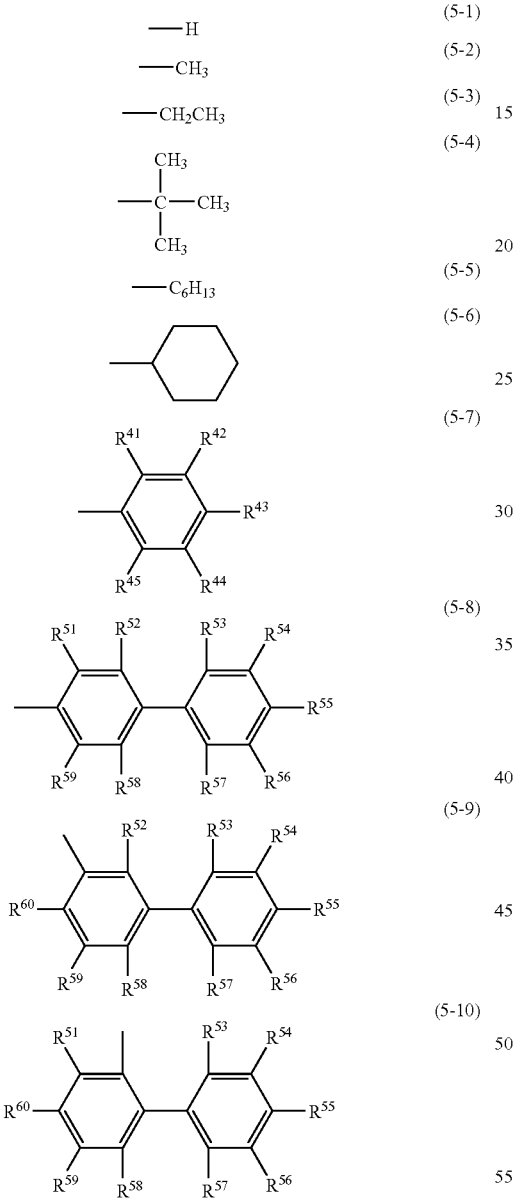

wherein R$^{41}$ to R$^{45}$, R$^{51}$ to R$^{68}$, and R$^{71}$ to R$^{79}$ each independently represent any of a hydrogen atom, an alkyl group having 1 to 6 carbon atoms, a phenyl group, or a biphenyl group.

14. The light-emitting element according to claim 7,
wherein Ar, R$^1$, and R$^6$ each represent an unsubstituted phenyl group,
wherein α$^1$ and α$^2$ each represent a phenylene group, and
wherein R$^2$ to R$^5$ and R$^7$ to R$^{10}$ each represent a hydrogen atom.

15. An electronic device comprising:
a light emitting element,
wherein the light emitting element comprises:
a first electrode;
an EL layer over the first electrode; and
a second electrode over the EL layer,
wherein the EL layer comprises a quinoxaline derivative represented by a general formula (G1), and

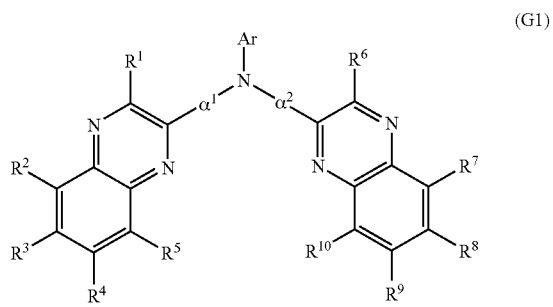

wherein:
α$^1$ and α$^2$ each independently represent an arylene group having 6 to 13 carbon atoms which form an aromatic ring,
Ar represents an aryl group having 6 to 13 carbon atoms which form an aromatic ring,
R$^1$ and R$^6$ each independently represent any of a hydrogen atom, an alkyl group having 1 to 6 carbon atoms, or an aryl group having 6 to 13 carbon atoms which form an aromatic ring, and
R$^2$ to R$^5$ and R$^7$ to R$^{10}$ each independently represent any of a hydrogen atom, an alkyl group having 1 to 6 carbon atoms, a substituted or unsubstituted phenyl group, or a substituted or unsubstituted biphenyl group.

16. The electronic device according to claim 15, wherein the EL layer further comprises a fluorescent substance.

17. The electronic device according to claim 15, wherein the EL layer further comprises a phosphorescent substance.

18. The electronic device according to claim 15,
wherein α$^1$ and α$^2$ in the general formula (G1) each independently represent any of general formulae (2-1) to (2-7) below, and

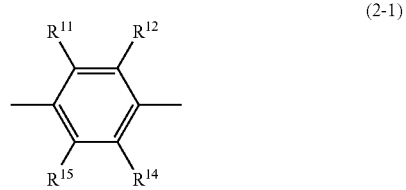

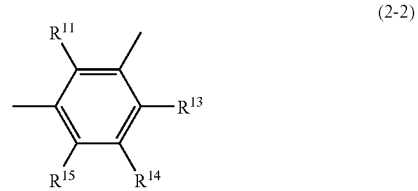

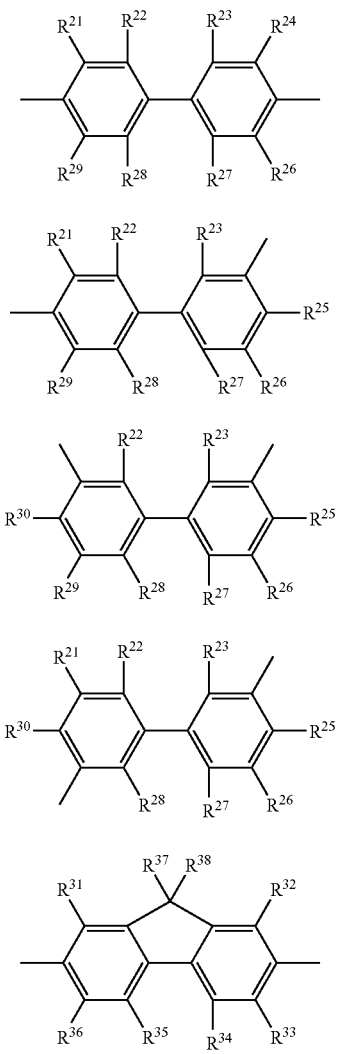

(2-3)

(2-4)

(2-5)

(2-6)

(2-7)

wherein:

$R^{11}$ to $R^{15}$ and $R^{21}$ to $R^{36}$ each independently represent any of a hydrogen atom, an alkyl group having 1 to 6 carbon atoms, or a phenyl group, and $R^{37}$ and $R^{38}$ each independently represent a hydrogen atom or an alkyl group having 1 to 6 carbon atoms.

19. The electronic device according to claim 15, wherein Ar in the general formula (G1) is any of general formulae (3-1) to (3-7) below, and

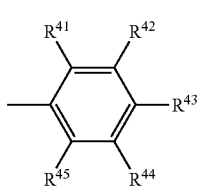

(3-1)

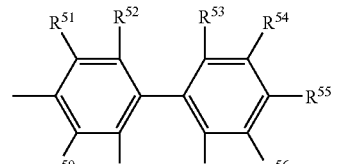

(3-2)

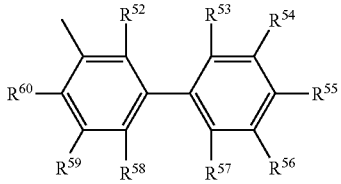

(3-3)

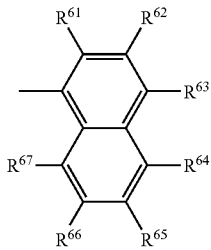

(3-4)

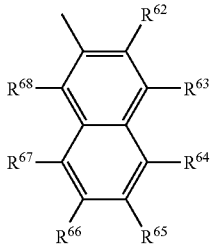

(3-5)

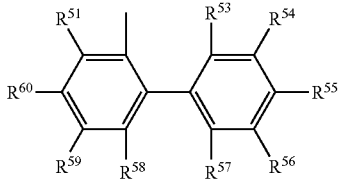

(3-6)

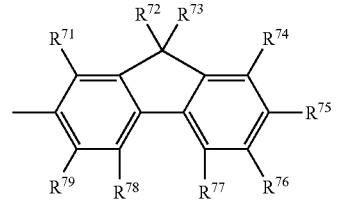

(3-7)

wherein:

$R^{41}$ to $R^{45}$, $R^1$ to $R^{68}$, and $R^{71}$ to $R^{79}$ each independently represent any of a hydrogen atom, an alkyl group having 1 to 6 carbon atoms, a phenyl group, or a biphenyl group.

20. The electronic device according to claim 15, wherein $R^1$ and $R^6$ in the general formula (G1) each independently represent any of structural formulae (4-1) to (4-6) or general formulae (4-7) to (4-12), and

—H    (4-1)

—CH₃   (4-2)

-continued

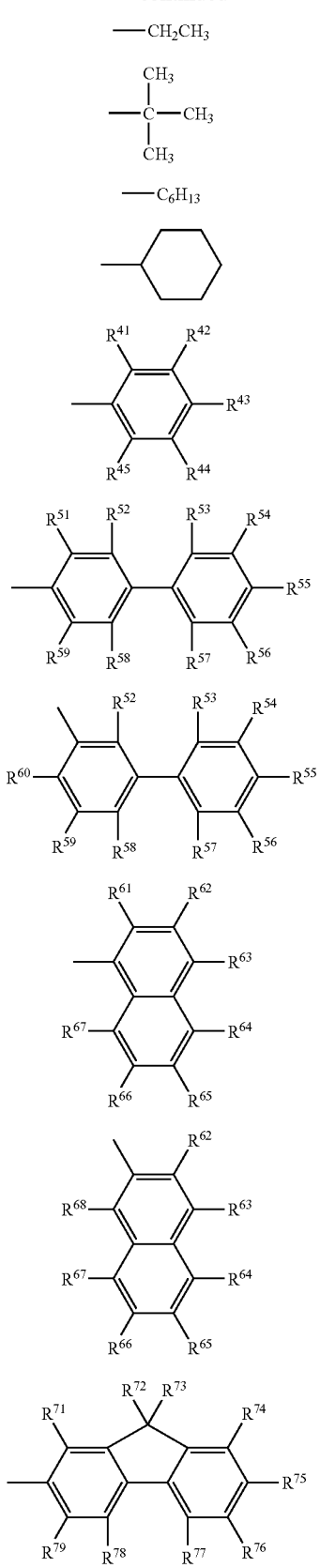

(4-3)
(4-4)
(4-5)
(4-6)
(4-7)
(4-8)
(4-9)
(4-10)
(4-11)
(4-12)

wherein:
R″ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

21. The electronic device according to claim 15, wherein $R^2$ to $R^5$ and $R^7$ to $R^{10}$ in the general formula (G1) each independently represent any of structural formulae (5-1) to (5-6) or general formulae (5-7) to (5-10), and

 (5-1)
 (5-2)
 (5-3)
 (5-4)

 (5-5)
 (5-6)

 (5-7)

 (5-8)

 (5-9)

 (5-10)

wherein $R^{41}$ to $R^{45}$, $R^{51}$ to $R^{68}$, and $R^{71}$ to $R^{79}$ each independently represent any of a hydrogen atom, an alkyl group having 1 to 6 carbon atoms, a phenyl group, or a biphenyl group.

22. The electronic device according to claim 15, wherein Ar, $R^1$, and $R^6$ each represent an unsubstituted phenyl group,
wherein $\alpha^1$ and $\alpha^2$ each represent a phenylene group, and
wherein $R^2$ to $R^5$ and $R^7$ to $R^{10}$ each represent a hydrogen atom.

23. A lighting device comprising the light-emitting element according to claim 7.

* * * * *

UNITED STATES PATENT AND TRADEMARK OFFICE
CERTIFICATE OF CORRECTION

| | | |
|---|---|---|
| PATENT NO. | : 7,993,761 B2 | Page 1 of 1 |
| APPLICATION NO. | : 12/326342 | |
| DATED | : August 9, 2011 | |
| INVENTOR(S) | : Harue Osaka et al. | |

It is certified that error appears in the above-identified patent and that said Letters Patent is hereby corrected as shown below:

In the Specification:

Column 1, Line 26; Change "Alight" to --A light--.

Column 2, Line 66; Change "ring; and R to" to --ring; and $R^2$ to--.

Column 16, Line 11; Change "$R^5$ to $R^{68}$" to --$R^{51}$ to $R^{68}$--.

In the Claims:

Claim 3, Column 88, Line 55; Change "R|" to --$R^{51}$--.

Claim 7, Column 91, Line 29; Change "Balla" to --form--.

Claim 10, Column 92, Line 48; Change "R to $R^{15}$" to --$R^{11}$ to $R^{15}$--.

Claim 19, Column 98, Line 55; Change "R|" to --$R^{51}$--.

Claim 20, Column 100, Line 2; Change "R"" to --$R^{41}$--.

Signed and Sealed this

Seventh Day of February, 2012

David J. Kappos
*Director of the United States Patent and Trademark Office*